US012649755B2

(12) United States Patent
Yang et al.

(10) Patent No.: US 12,649,755 B2
(45) Date of Patent: Jun. 9, 2026

(54) PLASMIN INHIBITOR, PREPARATION METHOD THEREFOR AND APPLICATION THEREOF

(71) Applicant: SCINNOHUB PHARMACEUTICAL CO., LTD, Chengdu (CN)

(72) Inventors: Anle Yang, Chengdu (CN); Sen Ji, Chengdu (CN); Zhi Wang, Chengdu (CN); Hao Wang, Chengdu (CN); Dewei Zhang, Chengdu (CN); Xiao Wang, Chengdu (CN); Huan Shen, Chengdu (CN); Jie Xiang, Chengdu (CN); Jialing Xian, Chengdu (CN); Yan Wang, Chengdu (CN); Xiao Hu, Chengdu (CN); Xiaodong Zhang, Chengdu (CN); Jun Tang, Chengdu (CN)

(73) Assignee: SCINNOHUB PHARMACEUTICAL CO., LTD, Chengdu (CN)

( * ) Notice: Subject to any disclaimer, the term of this patent is extended or adjusted under 35 U.S.C. 154(b) by 356 days.

(21) Appl. No.: 18/260,072

(22) PCT Filed: Dec. 30, 2021

(86) PCT No.: PCT/CN2021/143140

§ 371 (c)(1),
(2) Date: Jun. 30, 2023

(87) PCT Pub. No.: WO2022/143911

PCT Pub. Date: Jul. 7, 2022

(65) Prior Publication Data

US 2024/0300986 A1 Sep. 12, 2024

(30) Foreign Application Priority Data

Dec. 31, 2020 (CN) ........................ 202011623062.X

(51) Int. Cl.
*C07F 9/6561* (2006.01)
*A61K 31/675* (2006.01)
*A61P 7/04* (2006.01)
*C07F 9/6558* (2006.01)

(52) U.S. Cl.
CPC .......... *C07F 9/6561* (2013.01); *A61K 31/675* (2013.01); *A61P 7/04* (2018.01); *C07F 9/65583* (2013.01)

(58) Field of Classification Search
CPC ........................... C07F 9/6561; C07F 9/65583
See application file for complete search history.

(56) References Cited

U.S. PATENT DOCUMENTS

2024/0124443 A1 4/2024 Yang et al.

FOREIGN PATENT DOCUMENTS

| | | | | |
|---|---|---|---|---|
| CN | 101115760 A | | 1/2008 | |
| CN | 102459246 A | | 5/2012 | |
| CN | 106458991 A | | 2/2017 | |
| CN | 107108638 A | | 8/2017 | |
| CN | 110684048 A | | 1/2020 | |
| EP | 421436 A2 | * | 10/1991 | ................ C07F 9/62 |
| WO | WO 2007/002013 A2 | | 1/2007 | |
| WO | WO 2008/149163 A2 | | 12/2008 | |
| WO | WO 2012/047156 A1 | | 4/2012 | |
| WO | 2013142328 A1 | | 9/2013 | |
| WO | WO 2015/067549 A1 | | 5/2015 | |
| WO | WO 2019/063015 A1 | | 4/2019 | |
| WO | WO 2020/108538 A1 | | 6/2020 | |

OTHER PUBLICATIONS

Ng et al., "Tranexamic acid: a clinical review", *Anaesthesiol Intensive Ther.*, 47(4), pp. 339-350, (2015).
Tengborn et al., "Tranexamic acid—an old drug still going strong and making a revival", *Thromb Res.*, 135(2), pp. 231-242, (2015).
Healy et al., "Pharmaceutical Solvates, Hydrates and Amorphous Forms: A Special Emphasis on Cocrystals," Advanced Drug Delivery Reviews, vol. 117, p. 25-46, (2017).
Kumar et al., "Prodrugs: Harnessing Chemical Modifications for Improved Therapeutics," Journal of Drug Delivery Science and Technology, vol. 90, 25 pages, (2023).
Rumthao et al., "Design, Synthesis, and Evaluation of Oxyanion-hole Selective Inhibitor Substituents for the S1 Subsite of Factor Xa," Bioorg MEd Chem Lett., vol. 14, No. 20, p. 5165-5170, (2004); Abstract Only.

* cited by examiner

*Primary Examiner* — Laura L Stockton
(74) *Attorney, Agent, or Firm* — Hoxie & Associates LLC

(57) ABSTRACT

A compound of formula (I) capable of inhibiting plasmin activity, delaying fibrinolysis, and having coagulation and hemostatic activity, pharmaceutically acceptable salts, hydrates, isomers, prodrugs and mixtures thereof, wherein X, and $R_1$ to $R_5$ are as defined in the description.

(I)

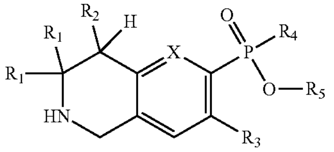

28 Claims, No Drawings

PLASMIN INHIBITOR, PREPARATION METHOD THEREFOR AND APPLICATION THEREOF

CROSS-REFERENCE TO RELATED APPLICATIONS

The present application is a U.S. National Stage application under 35 U.S.C. § 371 of International Application No. PCT/CN2021/143140, filed on Dec. 30, 2021, which claims priority to Chinese patent application No. 202011623062.X, filed on Dec. 31, 2020.

TECHNICAL FIELD

The invention relates to the field of medicinal chemistry, in particular to a plasmin inhibitors, process of their preparation, and their use in medicine.

BACKGROUND

Plasmin is a proteolytic enzyme that degrades fibrin. When tissue damage causes vascular rupture, a hemostatic mechanism is triggered involving vasoconstriction, platelet plug formation, initiation of the coagulation process, and the final formation of stable fibrin. At the same time, due to fibrin deposition, the fibrinolytic system is activated, which maintains a balance between fibrin formation and lysis, and plays a role in maintaining vessel patency and remodeling damaged tissue during repair of damaged vessel walls (Tengborn L, Blombäck M, Berntorp E. Thromb Res. 2015 Feb; 135(2): 231-42).

The fibrinolytic system includes plasminogen, tissue plasminogen activator (IPA) and urokinase plasminogen activator (uPA). Plasminogen binds to lysine residues on the surface of fibrin and is converted to plasmin by an activator (i.e., tPA) released from endothelial cells. Fibrinolysis inhibition can be used to treat bleeding. The use of antifibrinolytic drugs can reduce blood loss in cardiac surgery, trauma, orthopedic surgery, solid organ transplantation, obstetrics and gynecology, neurosurgery and non-surgical conditions (Ng W, Jerath A, Wąsowicz M. Anaesthesiol Intensive Ther. 2015; 47(4):339-50). In the early 1950s, the amino acid lysine was found to inhibit the activation of plasminogen, but the effect was too weak to be useful in the treatment of fibrinolytic hemorrhagic diseases. In 1953, Shosuke Okamoto and others showed that several sulfhydryl-and amino-carboxylic acids had anti-plasma protein effects, and found that ε-aminocaproic acid (EACA), a synthetic derivative of lysine, had a strong inhibitory effect on plasminogen. EACA has been widely used clinically, but requires a large dose and is accompanied by mild gastrointestinal side effects such as nausea. In 1962, 4-aminomethyl-cyclohexane-carboxylic acid (AMCHA) was discovered. This compound contains two stereoisomers, and further studies showed that its trans form (trans-4-aminomethyl-cyclohexane-carboxylic acid, i.e., tranexamic acid, TXA) has anti-fibrinolytic activity about 10 times that of EACA, and has been shown to be more tolerated (Tengborn L, Blombäck M, Berntorp E. Thromb Res. 2015 Feb; 135(2):231-42).

Tranexamic acid is a synthetic lysine derivative and antifibrinolytic agent that forms a reversible complex with plasminogen. By binding to plasminogen, interaction of plasminogen and plasmin heavy chain with fibrin lysine residue is blocked, thereby preventing binding of plasminogen to fibrin surface and delaying fibrinolysis. Tranexamic acid has been approved for the treatment of severe menstrual bleeding and various surgical bleeding disorders, and is currently the most commonly used hemostatic drug in clinical practice. However, a large number of literature reports show that tranexamic acid is prone to gastrointestinal adverse reactions after oral administration, such as nausea, vomiting, diarrhea and dyspepsia, and its dosage is relatively high, which may cause complications such as epilepsy in patients.

Other similar hemostatic drugs, such as aminocaproic acid, have the problems of rapid excretion in human body, weak hemostatic effect, short duration of action, many toxic reactions and the like, and can form thrombus when the dosage is too high, thereby limiting the application to patients with thrombosis tendency or thrombotic vascular diseases and renal insufficiency. The mechanism of aminomethylbenzoic acid is the same as that of aminocaproic acid, and its effect is 4 to 5 times stronger than that of aminocaproic acid. It has a significant effect on common chronic bleeding, but has no hemostatic effect on traumatic bleeding and cancer bleeding. In addition, excessive dosage can also promote thrombosis. Aprotinin, a commonly used hemostatic drug in bypass surgery, was also withdrawn from the market by the FDA in 2008 because it can induce renal failure, myocardial infarction, heart failure, and the like.

Hemostatic drugs with other mechanisms, such as carbacola, which acts on blood vessels, can induce epilepsy after repeated use; the thrombin, a hemostatic drug which promotes the blood coagulation process, can be applied to gastrointestinal bleeding or local bleeding only.

In view of the fact that the choice of clinically available hemostatic drugs is very limited. certain defects exist in the aspects of dosage, clinical indications and the like, and the existing drugs of the same type have the problems of large dosages, many adverse reactions, and are prone to complications such as epilepsy, it is necessary to develop a new hemostatic drug to better meet the clinical needs.

DISCLOSURE OF INVENTION

In a first aspect, the invention aims to provide a novel compound which can inhibit the activity of fibrinolytic enzyme, delay fibrinolysis and has the activities of blood coagulation and hemostasis.

In particular, the invention provides compounds represented by the structure of the following formula (I), and pharmaceutically acceptable salts, hydrates, isomers, prodrugs and mixtures thereof, (I)

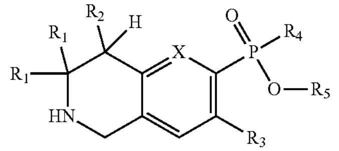

wherein X is selected from N or CR, R=H or halogen:

each of $R_1$ is independently selected from the group consisting of hydrogen, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, substituted or unsubstituted aromatic heterocyclic group, or two $R_1$ together with the carbon atom to which they are attached form a carbocyclic ring containing from 3 to 8 carbon atoms;

$R_2$ is selected from the group consisting of hydrogen, hydroxyl, halogen, substituted or unsubstituted amino, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, substituted or unsubstituted aromatic heterocyclic group;

$R_1$ is selected from the group consisting of hydrogen, halogen, substituted or unsubstituted alkyl;

$R_4$ is selected from the group consisting of hydrogen, substituted or unsubstituted amino, hydroxyl, substituted or unsubstituted aryl, substituted or unsubstituted alkyl, substituted or unsubstituted aromatic heterocyclic group;

$R_5$ is selected from the group consisting of hydrogen, substituted or unsubstituted alkyl, haloalkyl, substituted or unsubstituted cycloalkyl, substituted or unsubstituted aliphatic heterocyclic group, substituted or unsubstituted aryl, substituted or unsubstituted aromatic heterocyclic group, alkyl-carbonyl-oxy-alkyl, alkoxy-carbonyl-oxy-alkyl.

In one embodiment, the present invention is directed to compounds represented by the structure of the following formula (I'), pharmaceutically acceptable salts, hydrates, isomers, prodrugs and mixtures thereof, Formula I'

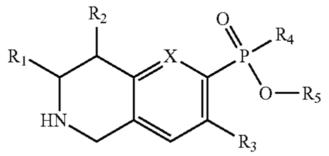

wherein X is selected from N or CR, R=H or halogen:

$R_1$ is selected from the group consisting of hydrogen, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, substituted or unsubstituted aromatic heterocyclic group;

$R_2$ is selected from the group consisting of hydrogen, hydroxyl, substituted or unsubstituted amino, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, substituted or unsubstituted aromatic heterocyclic group;

$R_3$ is selected from the group consisting of hydrogen, halogen, substituted or unsubstituted alkyl;

$R_4$ is selected from the group consisting of hydrogen, substituted or unsubstituted amino, hydroxyl, substituted or unsubstituted aryl, substituted or unsubstituted alkyl, substituted or unsubstituted aromatic heterocyclic group;

$R_5$ is selected from the group consisting of hydrogen, substituted or unsubstituted alkyl, haloalkyl, substituted or unsubstituted cycloalkyl, substituted or unsubstituted aliphatic heterocyclic group, substituted or unsubstituted aryl, and substituted or unsubstituted aromatic heterocyclic group.

In some embodiments, X is N.

In some embodiments, each of $R_1$ is independently selected from the group consisting of hydrogen, substituted or unsubstituted $C_1$-$C_6$ alkyl, substituted or unsubstituted $C_1$-$C_6$ alkoxy, $C_1$-$C_4$ haloalkyl, substituted or unsubstituted $C_3$-$C_6$ cycloalkyl, substituted or unsubstituted 4-8 membered aliphatic heterocyclic group, substituted or unsubstituted 6-10 membered aryl, substituted or unsubstituted 6-10 membered aromatic heterocyclic group, or two $R_1$ together with the carbon atom to which they are attached form a carbocyclic ring comprising 3 to 8 carbon atoms.

In some embodiments, $R_2$ is selected from the group consisting of hydrogen, halogen, hydroxyl, substituted or unsubstituted amino, substituted or unsubstituted $C_1$-$C_6$ alkyl, substituted or unsubstituted $C_1$-$C_6$ alkoxy, $C_1$-$C_4$ haloalkyl, substituted or unsubstituted $C_3$-$C_6$ cycloalkyl, substituted or unsubstituted 4-8 membered aliphatic heterocyclic group, substituted or unsubstituted 6-10 membered aryl, substituted or unsubstituted 6-10 membered aromatic heterocyclic group.

In some embodiments, $R_3$ is selected from the group consisting of hydrogen, fluoro, chloro, bromo, substituted or unsubstituted $C_1$-$C_4$ alkyl.

In some embodiments, $R_4$ is selected from the group consisting of hydrogen, substituted or unsubstituted amino, hydroxyl, substituted or unsubstituted 6-10 membered aryl, substituted or unsubstituted $C_1$-$C_6$ alkyl, substituted or unsubstituted 6-10 membered aromatic heterocyclic group.

In some embodiments, $R_5$ is selected from the group consisting of hydrogen, substituted or unsubstituted $C_1$-$C_4$ alkyl, substituted or unsubstituted $C_1$-$C_4$ haloalkyl, substituted or unsubstituted $C_3$-$C_6$ cycloalkyl, substituted or unsubstituted 4-8 membered aliphatic heterocyclic group, substituted or unsubstituted 6-10 membered aryl, substituted or unsubstituted 6-10 membered aromatic heterocyclic group, ($C_1$-$C_4$) alkyl-carbonyl-oxy-($C_1$-$C_4$) alkyl, ($C_1$-$C_4$) alkoxy-carbonyl-oxy-($C_1$-$C_4$)alkyl.

In some embodiments, each of $R_1$ is independently selected from the group consisting of hydrogen, substituted or unsubstituted $C_1$-$C_6$ alkyl, substituted or unsubstituted $C_3$-$C_6$ alkoxy; wherein the substituted $C_1$-$C_6$ alkyl or substituted $C_1$-$C_6$ alkoxy is substituted with one or more groups selected from hydroxyl, alkyl, cycloalkyl, alkoxy, aryl, or substituted aryl; in some embodiments, the substituted $C_1$-$C_6$ alkyl or substituted $C_1$-$C_6$ alkoxy is substituted with one or more groups selected from hydroxyl, phenyl, $C_3$-$C_4$ alkoxy, phenyl substituted with $C_1$-$C_4$ alkoxy, cyclohexyl.

In some embodiments, each of $R_1$ is independently selected from the group consisting of hydrogen, $-CH_2H$, isobutyl, tert-butyl, $-O(CH_2)_2OH$, $-O(CH_2)_3OH$, $-(CH_2)_4OH$, $-CH_2-O(CH_2)_3OH$, phenylethyl, propyl, isopentyl, 3,3-dimethylbutyl, cyclohexylmethyl, cyclohexylethyl, phenylpropyl, 4-methoxyphenylethyl.

In some embodiments, one of $R_1$ is hydrogen.

In some embodiments, two $R_1$ together with the carbon atom to which they are attached form a cyclobutyl, cyclopentyl, or cyclohexyl ring.

In some embodiments, $R_2$ is selected from the group consisting of hydrogen, halogen, hydroxyl, hydroxy-substituted $C_1$-$C_6$ alkoxy, 6 membered aliphatic heterocyclic group containing 1 to 3 heteroatoms selected from N, O and S, wherein the S heteroatom is optionally oxidized.

In some embodiments, $R_2$ is selected from the group consisting of hydrogen, hydroxyl, $-OCH_2CH_2OH$,

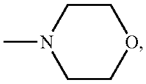, 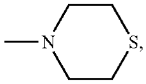, 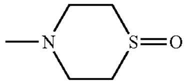 and

-continued

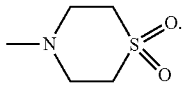

In some embodiments, $R_2$ is hydrogen.

In some embodiments, $R_3$ is selected from hydrogen or fluoro.

In some embodiments, $R_4$ is selected from the group consisting of hydroxyl, phenyl, $C_3$-$C_6$ alkyl or phenyl substituted $C_1$-$C_6$ alkyl.

In some embodiments, $R_4$ is selected from the group consisting of hydroxyl, phenyl, ethyl, or phenylethyl.

In some embodiments, $R_4$ is selected from the group consisting of hydroxyl, phenyl or phenylethyl.

In some embodiments, $R_5$ is selected from the group consisting of hydrogen, substituted or unsubstituted $C_1$-$C_4$ alkyl, ($C_1$-$C_4$) alkyl-carbonyl-oxy-($C_1$-$C_4$) alkyl, or ($C_1$-$C_4$) alkoxy-carbonyl-oxy-($C_1$-$C_4$) alkyl.

In some embodiments, $R_5$ is selected from the group consisting of hydrogen, ethyl, methylcarbonyloxymethyl, isopropylcarbonyloxymethyl or methoxycarbonyloxymethyl.

In some embodiments, the compounds of formula I of the present invention have the following structure:

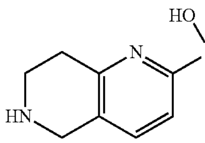

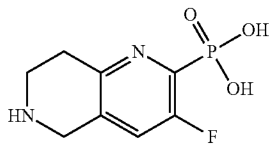

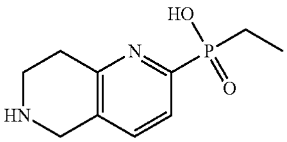

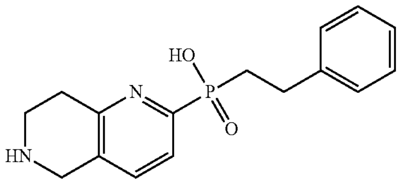

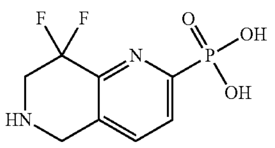

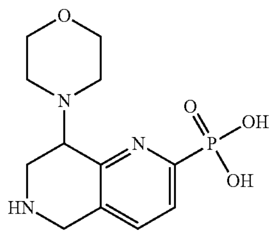

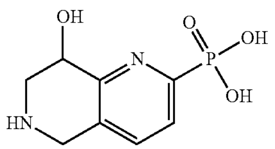

-continued

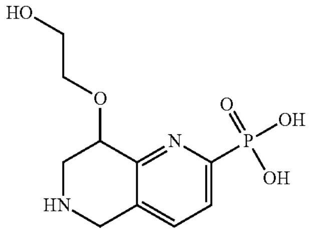

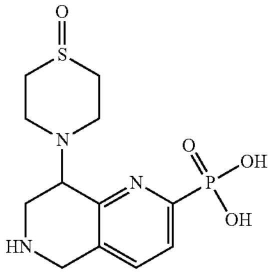

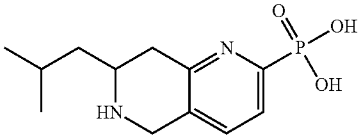

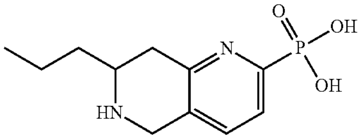

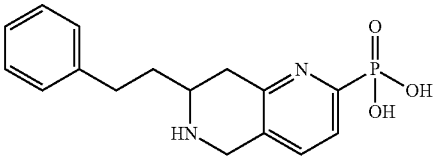

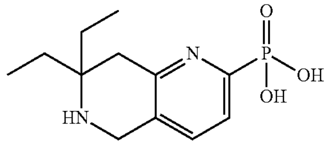

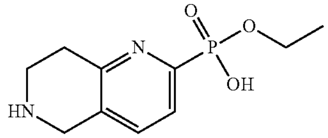

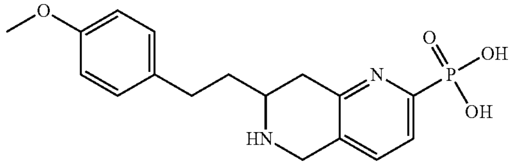

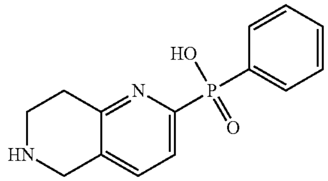

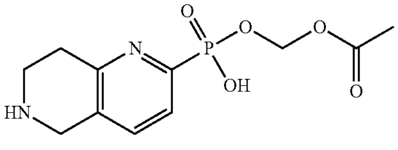

-continued

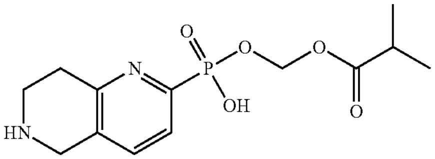

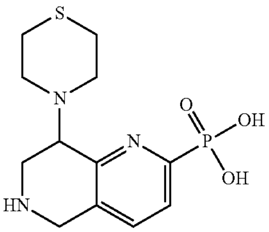

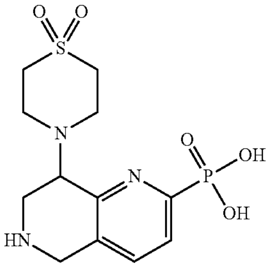

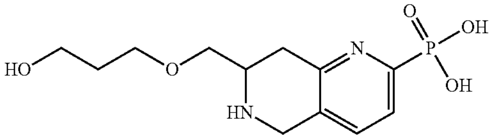

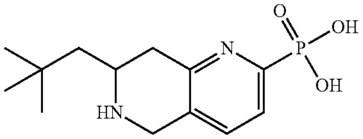

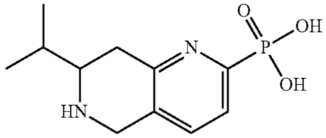

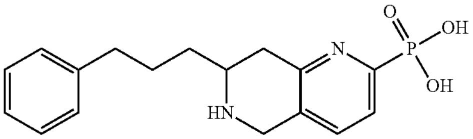

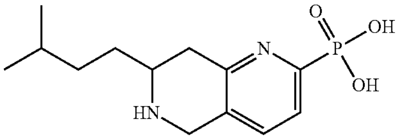

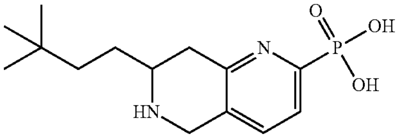

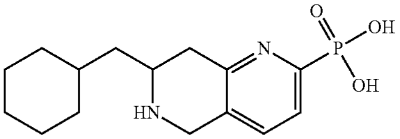

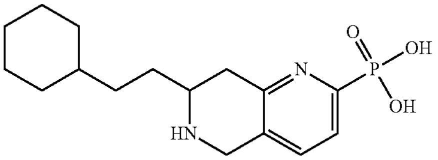

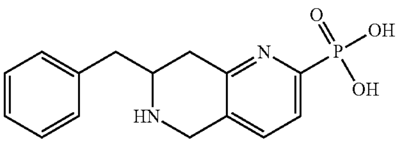

-continued

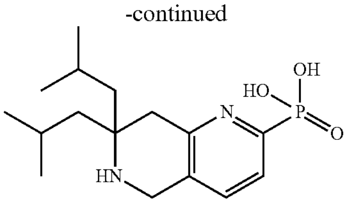

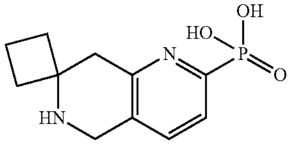

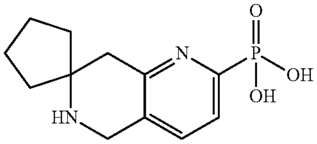

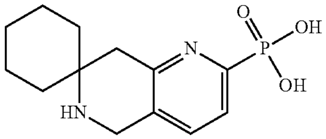

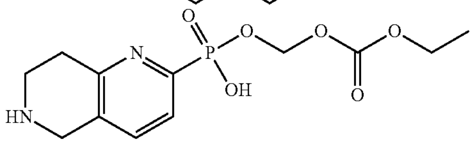

.

Another object of the present invention is to provide a pharmaceutical composition, comprising at least one of the aforementioned compounds, or pharmaceutically acceptable salts, hydrates, isomers, prodrugs and mixtures thereof, and at least one pharmaceutically acceptable excipient.

Another object of the present invention is to provide a use of the aforementioned compounds, or pharmaceutically acceptable salts, hydrates, isomers, prodrugs and mixtures thereof, or pharmaceutical composition for the manufacture of a medicament. The medicament can effectively inhibit fibrinolytic enzyme activity, delay fibrinolysis, exert excellent blood coagulation and hemostasis therapeutic activity, and can be used for abnormal bleeding caused by hyperfibrinolysis, surgical and postoperative bleeding and the like.

Another object of the present invention is to provide a method for treating and/or alleviating bleeding diseases or conditions, comprising administering to a subject in need thereof one or more of the aforementioned pharmaceutical compositions or compounds of formula I or pharmaceutically acceptable salts, hydrates, isomers, prodrugs or mixtures thereof.

Definitions

Unless otherwise stated, the following terms and phrases used herein are intended to have the following meanings. A particular term or phrase should not be considered indeterminate or unclear if it is not specifically defined, but should be understood according to its ordinary meaning. When a trade name appears herein, it is intended to refer to its corresponding commercial product or its active ingredient.

The term "pharmaceutically acceptable" as used herein means suitable for use in contact with tissues of humans and animals without undue toxicity, irritation, allergic reaction or other problems or complications, having a reasonable benefit/risk ratio.

The term "pharmaceutically acceptable salts" refers to salts of the compound of the present invention prepared from a compound of the present invention having a particular substituent with relatively nontoxic acids or bases. When a compound of the present invention contains relatively acidic functional groups, base addition salts can be obtained by contacting the neutral form of such compound with a sufficient amount of base, either neat or in a suitable inert solvent. When a compound of the present invention contains relatively basic functional groups, acid addition salts can be obtained by contacting the neutral form of such compound with a sufficient amount of acid, either neat or in a suitable inert solvent.

The compounds of the present invention may exist in specific geometric or stereoisomeric forms. The present invention contemplates all such compounds. The term "isomer" as used herein includes the cis and trans isomers, (−)- and (+)-enantiomers, (R)- and (S)-enantiomers, diastereomers, (D)-isomers, (L)-isomers, and racemic and other mixtures thereof, all of which are within the scope of the present invention.

"Alkyl" refers to a straight chain or branched saturated aliphatic hydrocarbon group, for example, $C_1$-$C_4$ alkyl and $C_1$-$C_6$ alkyl refer to saturated aliphatic hydrocarbon groups containing 1 to 4 carbon atoms and 1 to 6 carbon atoms, respectively. Examples of alkyl groups described herein include, but are not limited to, methyl, ethyl, propyl, isopropyl, n-butyl, t-butyl, isopentyl, 3,3-dimethylbutyl, and the like, and their various isomers.

"Alkoxy" means-O-alkyl; for example, $C_1$-$C_6$ alkoxy refers to a straight chain or branched alkoxy containing 1 to 6 carbon atoms, $C_1$-$C_5$ alkoxy refers to a straight chain or branched alkoxy containing 1 to 3 carbon atoms. Examples of alkoxy described herein include, but are not limited to, methoxy, ethoxy, n-propoxy, isopropoxy, and the like.

"Cycloalkyl" refers to a saturated or partially unsaturated monocyclic or polycyclic cyclic hydrocarbon substituent. For example, "$C_3$-$C_6$ cycloalkyl" refers to cycloalkyl groups containing 3 to 6 carbon atoms. Examples of cycloalkyl groups described herein include, but are not limited to, cyclopropyl, cyclobutyl, cyclopentyl, cyclopentenyl, cyclohexyl, cyclohexenyl, and the like.

"Aliphatic heterocyclic group" refers to a saturated, monocyclic hydrocarbon substituent in which one or more ring atoms are replaced with a heteroatom selected from N, O and S, the remaining ring atoms are carbon, and wherein the S heteroatom is optionally oxidized. For example, "3-8 membered aliphatic heterocyclic group" means a saturated cyclic hydrocarbon substituent containing 3 to 8 ring atoms, wherein one or more ring atoms are replaced with a heteroatom selected from N, O and S, the remaining ring atoms are carbon, and wherein the S heteroatom is optionally oxidized. Examples of said aliphatic heterocyclic group described herein include, but are not limited to, oxetanyl, pyrrolidinyl, tetrahydrofuryl, morpholinyl, thiomorpholinyl,

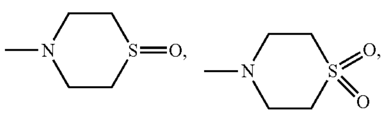

and the like.

"Aromatic heterocyclic group" refers to an aromatic cyclic substituent in which one or more ring atoms are replaced with a heteroatom selected from N, O and S, with the remaining ring atoms being carbon. For example, "5-6 membered aromatic heterocyclic ring" refers to an aromatic heterocyclic group containing 5 to 6 ring atoms. Examples of the aromatic heterocyclic group described herein include, but are not limited to, pyridyl, pyrimidinyl, imidazolyl, pyrazolyl, thiazolyl, oxazolyl, isoxazolyl, 1,2,4-oxadiazolyl.

"Aryl" refers to an aromatic cyclic group, e.g., "6-10 membered aryl" refers to an aromatic cyclic group containing 6 to 10 carbon ring atoms. Examples of aryl described herein include, but are not limited to, phenyl, naphthyl, and the like.

"Optionally" means that the subsequently described event or circumstance may, but need not, occur.

The abbreviations used in this disclosure are known to those skilled in the art and, unless otherwise indicated, are intended to have the meanings known in the art. For example, DMF represents N,N-dimethylformamide; THF represents tetrahydrofuran; Me represents methyl.

The activity of the compounds of the invention was determined by plasma clot lysis assay and thromboelastogram (TEG) assay. In the experiment, rtPA was added to human plasma or whole blood to activate plasminogen (Plasminogen), and the formed plasmin (Plasmin) can degrade fibrin, which is manifested as rapid degradation of plasma fibrin clots and whole blood clots. In the two experiments, the compound of the present invention can effectively inhibit the fibrinolysis process, prolong the plasma clot lysis time (CLT), and exert excellent blood coagulation and hemostasis activities. Both the pharmacological activity and safety of the compound of the present invention are obviously superior to tranexamic acid, the most widely used hemostatic drug currently in clinical practice; moreover, the compound of the present invention is convenient for preparation and large-scale industrial production, can effectively reduce the cost of medication, and has great clinical application value.

DETAILED DESCRIPTION

The following examples illustrate the synthesis of the compounds and intermediates of the present invention by way of example only and should not be construed as limiting the scope of the invention. Unless otherwise specified, the raw materials and reagents involved in the present invention can be obtained from commercial sources, and the specific sources do not influence the implementation of the technical solution of the present invention.

Example 1: Preparation of (5,6,7,8-tetrahydro-1,6-naphthyridin-2-yl)phosphonic Acid Hydrochloride

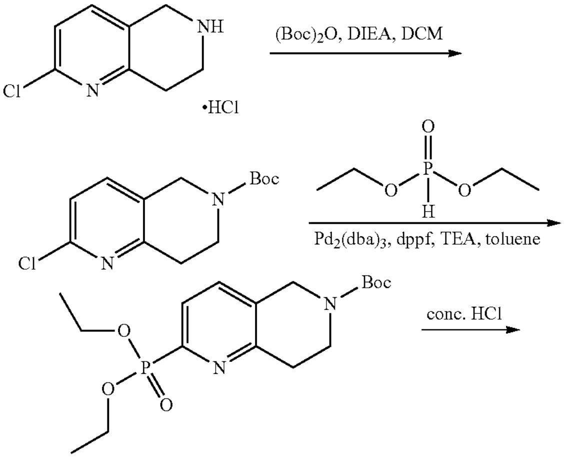

-continued

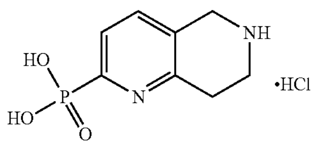

Step 1: Preparation of Tert-butyl 2-chloro-7,8-dihydro-1,6-naphthyridin-6-(5H)-carboxylate

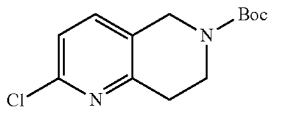 [SMILES: CC(C)(C)OC(=O)N1CCc2nc(Cl)ccc2C1]

2-Chloro-5,6,7,8-tetrahydro-1,6-naphthyridine hydrochloride (0.9 g) was suspended in dichloromethane (15 mL), N,N-diisopropylethylamine (1.4 g) was added, followed by di-tert-butyl dicarbonate (1.15 g), and the reaction was carried out at room temperature for 1 h. TLC showed the consumption of starting material was complete. The reaction solution was diluted with water, extracted with dichloromethane, and the organic phases were combined, dried over anhydrous sodium sulfate, filtered, and concentrated. The obtained crude product was purified by column chromatography to obtain the title compound (1.12 g).

MS (ESI) m/z $(M+H)^+$=269.0.

Step 2: Preparation of Tert-butyl 2-(diethoxyphosphoryl)-7,8-dihydro-1,6-naphthyridin-6(5H) -carboxylate

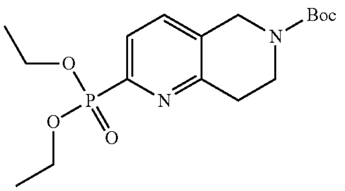 [SMILES: CCOP(=O)(OCC)c1ccc2c(n1)CCN(C(=O)OC(C)(C)C)C2]

Tert-butyl 2-chloro-7,8-dihydro-1,6-naphthyridin-6(5H)-carboxylate (100 mg) was dissolved in toluene (20 mL) under argon atmosphere, and diethyl phosphite (102 mg), tris(dibenzylideneacetone)dipalladium (34 mg), 1,1'-bis(diphenylphosphino)ferrocene (41 mg), and triethylamine (75 mg) were added to the solution, and the system was reacted overnight at 120° C. TLC showed the consumption of starting material was complete. The reaction solution was diluted with ethyl acetate, filtered through celite, and the filtrate was collected and concentrated. The obtained crude product was purified by preparative TLC to obtain the title compound (70 mg).

MS (ESI) m/z $(M+H)^+$=371.1.

Step 3: Preparation of (5,6,7,8-tetrahydro-1,6-naphthyridin-2-yl)phosphonic Acid Hydrochloride

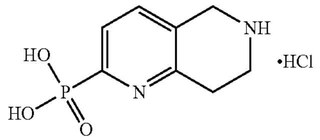 [SMILES: O=P(O)(O)c1ccc2c(n1)CCNC2 ; Cl]

Tert-butyl 2-(diethoxyphosphoryl)-7,8-dihydro-1,6-naphthyridin-6(5H)-carboxylate (70 mg) was dissolved in concentrated hydrochloric acid (5 mL) and reacted at 100° C. overnight. LCMS showed the consumption of the starting material was complete. The reaction was concentrated and the crude product was purified by pre-HPLC to obtain the title compound (30 mg).

MS (ESI) m/z $(M+H)^+$=215.0.

$^1$H NMR (400 MHZ, Deuterium Oxide) δ 8.35 (dd, J=8.0, 2.4 Hz, 1H), 8.06 (t, J=7.7 Hz, 1H), 4.59 (s, 2H), 3.67 (t, J=6.0 Hz, 2H), 3.49 (t, J=6.4 Hz, 2H).

Example 2: Preparation of (3-fluoro-5,6,7,8-tetrahydro-1,6-naphthyridin-2-yl)phosphonic Acid Hydrochloride

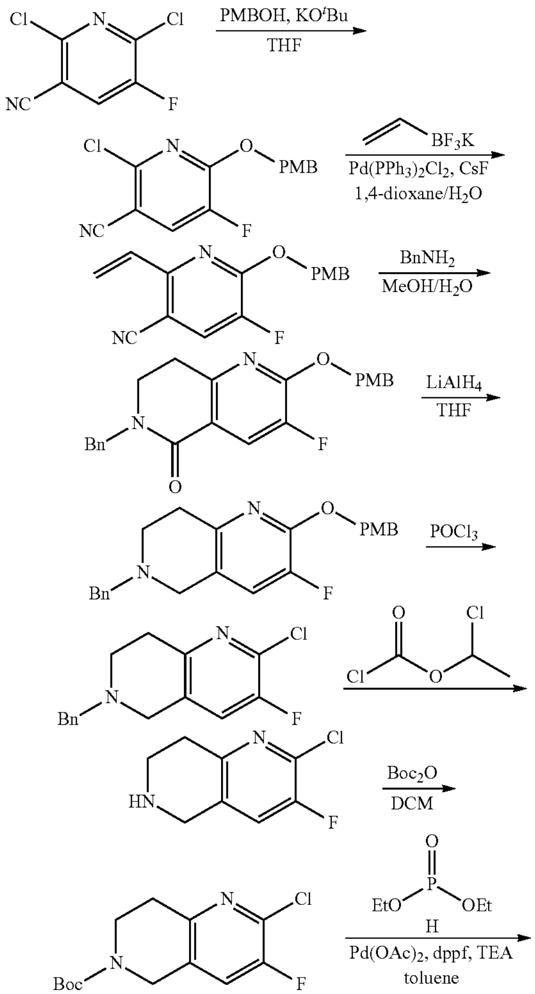

-continued

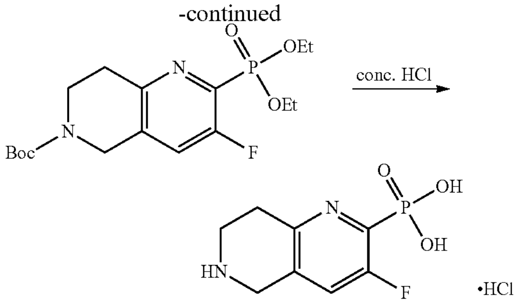

Step 1: Preparation of 2-chloro-5-fluoro-6-((4-methoxybenzyl)oxy)nicotinonitrile

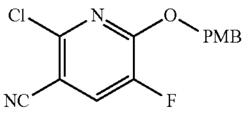

4-Methoxybenzyl alcohol (3.95 g) was dissolved in tetrahydrofuran (50 mL), cooled to −78° C. and stirred. Potassium tert-butoxide (3.5 g) was added under nitrogen, and the reaction was carried out at 0° C. for 0.5 hours. Cool to −78° C. again, a solution of 2,6-dichloro-5-fluoronicotinonitrile (5.0 g) in tetrahydrofuran (50 mL) was added dropwise. After the addition was complete, the cooling bath was removed, and the reaction was carried out overnight at room temperature. TLC showed the reaction was complete. Concentrating under reduced pressure, water was added and extracted with ethyl acetate, the layers were separated, the organic phases were combined, dried over anhydrous sodium sulfate, filtered and concentrated. The resulting crude product was purified by column chromatography to obtain the title compound (6.2 g).

MS (ESI) m/z $(M+H)^+$=293.1

Step 2: Preparation of 5-fluoro-6-((4-methoxybenzyl)oxy)-2-vinyl-nicotinonitrile

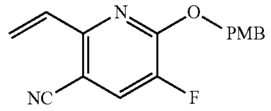

2-Chloro-5-fluoro-6-((4-methoxybenzyl)oxy)nicotinonitrile (6.0 g), potassium vinyltrifluoroborate (5.5 g), [1,1'-bis(diphenylphosphino)ferrocene]palladium dichloride (0.29 g) and cesium fluoride (6.23 g) were dissolved in 1,4-dioxane (60 mL) and water (6 mL) under nitrogen atmosphere and reacted overnight at 90° C., and TLC showed substantial completion of the reaction. Concentrating under reduced pressure, water was added and extracted with ethyl acetate, the layers were separated, the organic phases were combined, dried over anhydrous sodium sulfate, filtered and concentrated. The resulting crude product was purified by column chromatography to obtain the title compound (2.68 g).

MS (ESI) m/z $(M+H)^+$=285.1.

Step 3: Preparation of 6-benzyl-3-fluoro-2-((4-methoxybenzyl)oxy)-7,8-dihydro-1,6-naphthyridin-5(6H)-one

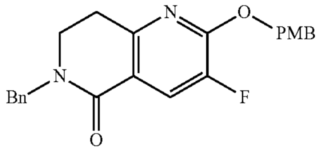

5-Fluoro-6-((4-methoxybenzyl)oxy)-2-vinyl-nicotinonitrile (2.68 g) was dissolved in methanol (20 mL) and water (4 mL), and benzylamine (12.44 g) was added. The reaction was allowed to react overnight at 100° C., and TLC showed substantial completion of the reaction. Concentrating under reduced pressure, water was added extracted with dichloromethane, the layers were separated, the organic phase was washed with 1M hydrochloric acid, combined, dried over anhydrous sodium sulfate, filtered and concentrated. The resulting crude product was purified by column chromatography to obtain the title compound (2.37 g).

MS (ESI) m/z $(M+H)^+$=393.1.

Step 4: Preparation of 6-benzyl-3-fluoro-2-((4-methoxybenzyl)oxy)-5,6,7,8-tetrahydro-1,6-naphthyridine

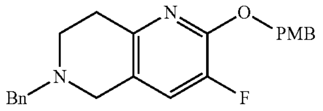

6-Benzyl-3-fluoro-2-((4-methoxybenzyl)oxy)-7,8-dihydro-1,6-naphthyridin-5(6H)-one (1.19 g) was dissolved in tetrahydrofuran (20 mL) under ice-water bath cooling, lithium aluminium hydride (0.29 g) was added in portions, the system was moved to 70° C. and heated for 4 hours, and TLC showed that the reaction was substantially complete. Under ice-water bath cooling, 0.5 mL of water, 0.5 mL of a 15% aqueous sodium hydroxide solution and 1.5 mL of water were sequentially added dropwise, and after stirring at room temperature for 15 minutes, anhydrous magnesium sulfate was added thereto and the mixture was stirred for 15 minutes. Filtered by addition of celite and anhydrous sodium sulfate, the filter cake was washed with ethyl acetate, and the filtrate was concentrated to obtain the title compound (1.15 g).

MS (ESI) m/z $(M+H)^+$=379.1.

Step 5: Preparation of 6-benzyl-2-chloro-3-fluoro-5,6,7,8-tetrahydro-1,6-naphthyridine

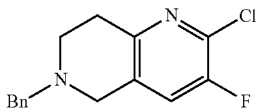 [SMILES: Fc1cc2c(nc1Cl)CCN(Cc1ccccc1)C2]

6-Benzyl-3-fluoro-2-((4-methoxybenzyl)oxy)-5,6,7,8-tetrahydro-1,6-naphthyridine (1.14 g) was dissolved in phosphorus oxychloride (10 mL) under ice-water bath cooling, reacted overnight at 100° C., and TLC showed substantial completion of the reaction. The mixture was concentrated under reduced pressure, diluted with ethyl acetate, and the reaction solution was added dropwise to crushed ice, and the pH was adjusted to about 10 with saturated sodium carbonate solution. Extracted with ethyl acetate and washed with saturated sodium chloride solution, the organic phases were combined, dried over anhydrous sodium sulfate, filtered, and concentrated to obtain a crude product (0.82 g).

MS (ESI) m/z $(M+H)^+$=277.1

Step 6: Preparation of 2-chloro-3-fluoro-5,6,7,8-tetrahydro-1,6-naphthyridine

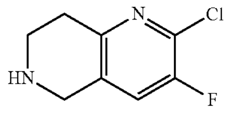 [SMILES: Fc1cc2c(nc1Cl)CCNC2]

6-Benzyl-2-chloro-3-fluoro-5,6,7,8-tetrahydro-1,6-naphthyridine (0.82 g) was dissolved in 1,2-dichloroethane (8 mL) under ice-water bath cooling, N,N-diisopropylethylamine (1.93 g) and 1-chloroethyl chloroformate (2.57 g) were added successively, reacted at 80° C. for 1.5 hours, and TLC showed substantial completion of the reaction. The mixture was concentrated, dissolved by addition of methanol and reacted at 60° C. for 1.5 hours, TLC showed substantial completion of the reaction. The mixture was concentrated under reduced pressure to give crude product, which was used directly in the next step.

MS (ESI) m/z $(M+H)^+$=187.1.

Step Preparation of Tert-butyl 2-chloro-3-fluoro-7,8-dihydro-1,6-naphthyridin-6(5H)-carboxylate

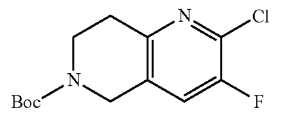 [SMILES: CC(C)(C)OC(=O)N1CCc2nc(Cl)c(F)cc2C1]

2-Chloro-3-fluoro-5,6,7,8-tetrahydro-1,6-naphthyridine (crude product described above) was dissolved in dichloromethane (10 mL) under ice-water bath cooling, triethylamine (0.91 g) and di-tert-butyl dicarbonate (0.98 g) were added, the reaction was carried out at room temperature for 2 hours, and TLC showed substantial completion of the reaction. Water was added and extracted with dichloromethane, the layers were separated, the organic phases were combined, dried over anhydrous sodium sulfate, filtered and concentrated. The resulting crude product was purified by column chromatography to obtain the title compound (0.28 g).

MS (ESI) m/z $(M+H)^+$=287.1.

Step 8: preparation of tert-butyl 2-(diethoxyphosphoryl)-3-fluoro-7,8-dihydro-1,6-naphthyridin-6(5H)-carboxylate

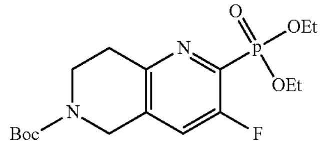

Tert-butyl 2-chloro-3-fluoro-7,8-dihydro-1,6-naphthyridin-6(5H)-carboxylate (100 mg) was dissolved in toluene (8 mL) under nitrogen atmosphere, diethyl phosphite (97 mg), palladium acetate (16 mg), 1,1'-bis(diphenylphosphino)ferrocene (78 mg), and triethylamine (71 mg) were added successively and reacted ovemight at 110° C. TLC showed substantial completion of the reaction. The mixture was concentrated under reduced pressure and the resulting crude product was purified by column chromatography to obtain the title compound (130 mg).

MS (ESI) m/z $(M+H)^+$=389.1.

Step 9: Preparation of (3-fluoro-5,6,7,8-tetrahydro-1,6-naphthyridin-2-yl)-phosphonic Acid Hydrochloride

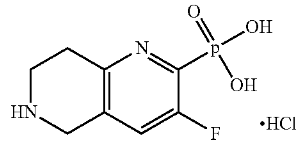

Tert-Butyl 2-(diethoxyphosphoryl)-3-fluoro-7,8-dihydro-1,6-naphthyridin-6(5H)-carboxylate (60 mg) was dissolved in concentrated hydrochloric acid (3 mL), heated to 100° C. and reacted in a sealed tube for 2 hours, TLC showed substantial completion of the reaction. The mixture was concentrated and the crude product was purified by pre-HPLC to obtain the title compound (30 mg).

MS (ESI) m/z $(M+H)^+$=233.0.

$^1H$ NMR (400 MHZ, Deuterium Oxide) δ 7.77 (d, J=7.1 Hz, 1H), 4.48 (s, 2H), 3.58 (s, 2H), 3.24 (s, 2H).

Example 3: Preparation of Ethyl (5,6,7,8-tetrahydro-1,6-naphthyridin-2-yl)-phosphinic Acid Hydrochloride

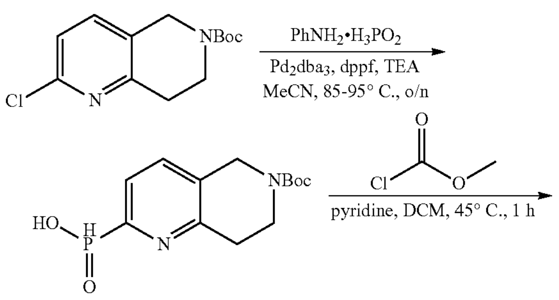

-continued

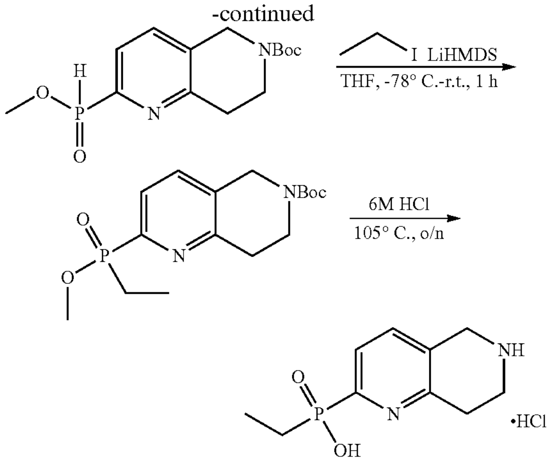

Step 1: Preparation of (6-(tert-butoxycarbonyl)-5,6,7,8-tetrahydro-1,6-naphthyridin-2-yl)-phosphinic Acid Tert-butyl 2-Chloro-7,8-dihydro-1,6-naphthyridin-6(5H)-carboxylate (2 g) and aniline phosphite (4.8 g) were weighed and dissolved in acetonitrile (40 mL), tris(dibenzylideneacetone)dipalladium (680 mg), diphenylphosphinoferrocene (830 mg) and triethylamine (5.2 mL) were added. After nitrogen purging, the reaction was carried out at 85° C. overnight, and then reacted at 95° C. for 4 h, and LC-MS monitoring showed that no raw material remained. The mixture was cooled to room temperature, adjusted to pH 3 with 2M dilute hydrochloric acid, evaporated to dryness by rotary evaporation, and the residue was purified by reverse phase column to obtain the title compound (1.6 g).

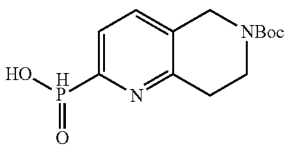

MS (ESI) m/z $(M+H)^+$=299.1.

Step 2: Preparation of Methyl (6-(tert-butoxycarbonyl)-5,6,7,8-tetrahydro-1,6-naphthyridin-2-yl)-phosphinate Under nitrogen atmosphere, (6-(tert-butoxycarbonyl)-5,6,7,8-tetrahydro-1,6-naphthyridin-2-yl)-phosphinic acid (400 mg) was weighed and dissolved in dichloromethane (10 mL), methyl chloroformate (0.2 mL) was added at room temperature, pyridine (0.2 mL) was added dropwise later, reacted at 45° C. for 1 h, and TLC monitoring showed that the reaction was complete. The reaction mixture was cooled to room temperature, quenched with water, and extracted three times with dichloromethane. The organic phases were combined, dried over anhydrous sodium sulfate, evaporated the solvent under reduced pressure, and the residue was purified by column chromatography to obtain the title compound (300 mg).

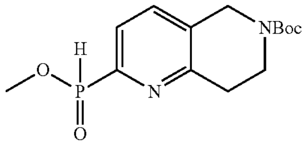 [SMILES: CO[PH](=O)c1ccc2c(n1)CCN(C(=O)OC(C)(C)C)C2]

MS (ESI) m/z $(M+H)^+$=313.1.

Step 3: Preparation of Tert-butyl 2-(etbyl(methoxy)phosphoryl)-7,8-dihydro-1,6-naphthyridin-6(5H)-carboxylate Methyl (6-(tert-butoxycarbonyl)-5,6,7,8-tetrahydro-1,6-naphtbyridin-2-yl)-phosphinate (50 mg) was weighed and dissolved in dry tetrahydrofuran (2 mL), lithium hexamethyldisilazide (0.19 mL, 1M in THF) was added at −78° C. under nitrogen protection. The reaction was carried out at −78° C. for 20 min, iodoethane (17 μL) was added dropwise, and then reacted at room temperature for 1 h, LC-MS monitoring showed that the reaction was complete. The reaction was quenched by the addition of saturated ammonium chloride solution, extracted three times with ethyl acetate, the organic phases were combined, dried over anhydrous sodium sulfate, and after evaporation of the solvent under reduced pressure, the residue was purified by column chromatography to obtain the title compound (20 mg).

MS (ESI) m/z $(M+H)^+$=341.1.

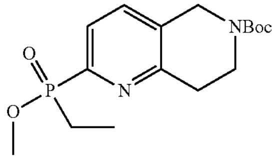 [SMILES: CCP(=O)(OC)c1ccc2c(n1)CCN(C(=O)OC(C)(C)C)C2]

Step 4: Preparation of Ethyl (5,6,7,8-tetrahydro-1,6-naphthyridin-2-yl)-phosphinic Acid Hydrochloride Tert-butyl 2-(ethyl(methoxy)phosphoryl)-7,8-dihydro-1,6-naphthyridin-6(5H)-carboxylate (20 mg) was weighed, 6M hydrochloric acid was added, the reaction was carried out overnight at 105° C., LC-MS monitoring showed that the reaction was complete. After cooling to room temperature and evaporation of the solvent under reduced pressure, the residue was purified by preparative HPLC to obtain the title compound (10 mg).

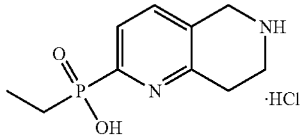

MS (ESI) m/z $(M+H)^+$=227.1.

$^1H$ NMR (400 MHZ, Deuterium Oxide) δ 7.63-7.62 (m, 2H), 4.36 (s, 2H), 3.57-3.53 (t, J=6.5 Hz, 2H), 3.18-3.15 (t, J=6.4 Hz, 2H), 1.74-1.65 (dq, J=15.3, 7.7 Hz, 2H), 0.85-0.76 (dt, J=18.6, 7.9 Hz, 3H).

Example 4: Preparation of Phenylethyl (5,6,7,8-tetrahydro-1,6-naphthyridin-2-yl) Phosphinic Acid Hydrochloride

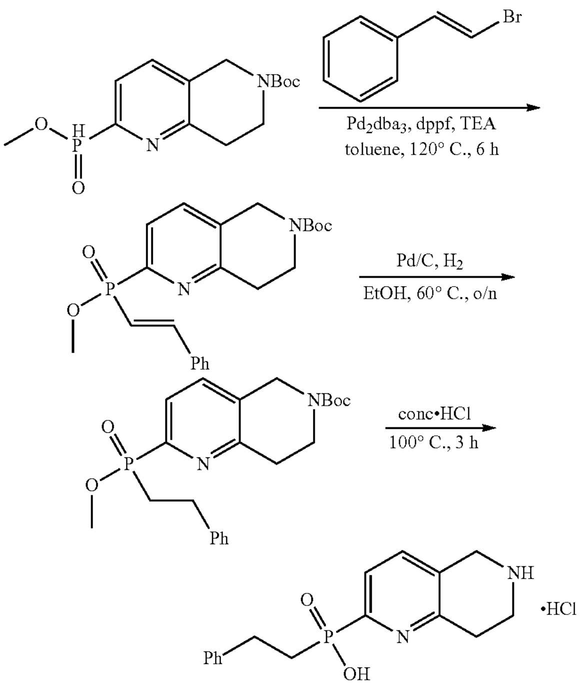

Step 1: Preparation of Tert-butyl 2-(methoxy(styryl) phosphoryl)-7,8-dihydro-1,6-naphthyridin-6(5H)-carboxylate Tert-butyl 2-(ethyl(methoxy)phosphoryl)-7,8-dihydro-1,6-naphthyridin-6(5H)-carboxylate (50 mg), (2-bromovinyl) benzene (31 μL) were weighed and dissolved in toluene (3 mL), tris(dibenzylideneacetone)dipalladium (15 mg), diphenylphosphinoferrocene (18 mg) and triethylamine (5.2 mL) were added. After nitrogen purging, the reaction was carried out at 120° C. for 6 hrs, and LC-MS monitoring showed that no starting material remained. After cooling to room temperature and evaporation of the solvent under reduced pressure, the residue was purified by column chromatography to obtain the title compound (35 mg).

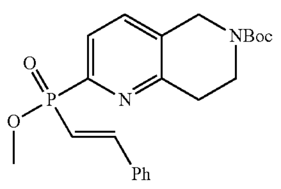 [SMILES: COP(=O)(/C=C/c1ccccc1)c1ccc2c(n1)CCN(C(=O)OC(C)(C)C)C2]

MS (ESI) m/z $(M+H)^+$=415.1.

Step 2: Preparation of Tert-butyl 2-(methoxy(phenylethyl)phosphoryl)-7,8-dihydro-1,6-naphthyridin-6 (5H)-carboxylate Tert-butyl 2-(methoxy(styryl)phosphoryl)-7,8-dihydro-1,6-naphthyridin-6(5H)-carboxylate (35 mg) was weighed, dissolved in ethanol (3 mL), 10% palladium on carbon (20 mg, 55% of moisture) was added, the reaction was allowed to react overnight at 60° C. under a hydrogen atmosphere, and LCMS monitoring showed that the reaction was complete. The reaction mixture was cooled to room temperature, filtered, and the filtrate was concentrated to obtain the title compound (40 mg crude).

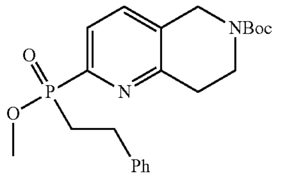 [SMILES: COP(=O)(CCc1ccccc1)c1ccc2c(n1)CCN(C(=O)OC(C)(C)C)C2]

MS (ESI) m/z $(M+H)^+$=417.1.

Step 3: Preparation of Phenylethyl (5,6,7,8-tetrahydro-1,6-naphthyridin-2-yl)phosphinic Acid Hydrochloride Tert-butyl 2-(methoxy(phenylethyl)phosphoryl)-7,8-dihydro-1,6-naphthyridin-6(5H)-carboxylate (40 mg crude) was weighed, 3 mL concentrated hydrochloric acid was added, the reaction was allowed to react at 100° C. for 3 hrs, and LC-MS monitoring showed that the reaction was complete. After cooling to room temperature and evaporation of the solvent under reduced pressure, the residue was purified by preparative HPLC to obtain the title compound (11.7 mg).

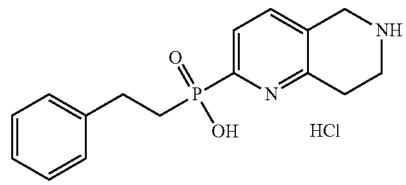 [SMILES: O=P(O)(CCc1ccccc1)c1ccc2c(n1)CCNC2 ; Cl]

MS (EST) m/z (M-H) =301.0.

$^1$H NMR (400 MHZ, Deuterium Oxide) δ 7.57-7.50 (m, 2H), 7.05-7.01 (m, 3H), 6.95-6.93(dd, J=7.5, 2.1 Hz, 2H), 4.30 (s, 2H), 3.49-3.46 (t, J=6.4 Hz, 2H), 2.98-2.95 (t, J=6.4 Hz, 2H), 2.67-2.59 (dt, J=15.1, 7.6 Hz, 2H), 2.14-2.07 (dt, J=15.2, 7.6 Hz, 2H).

Example 5: Preparation of (8,8-difluoro-5,6,7,8-tetrahydro-1,6-naphthyridin-2-yl) Phosphonic Acid Hydrochloride

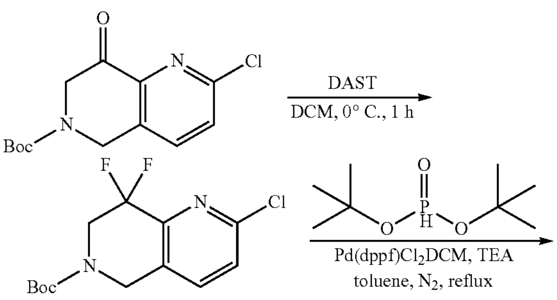

-continued

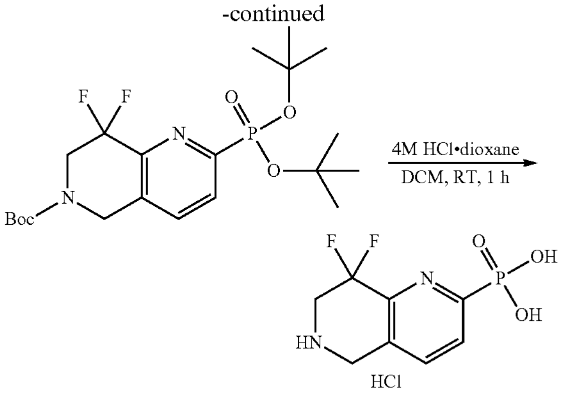

Step 1: Preparation of Tert-butyl 2-chloro-8,8-difluoro-7,8-dihydro-1,6-naphthyridin-6(5H)-carboxylate Tert-butyl 2-chloro-8-oxo-7,8-dihydro-1,6-naphthyridin-6(5H)-carboxylate (0.3 g) was weighed and dissolved in dichloromethane (4 mL), and diethylaminosulfur trifluoride (342 mg) was added dropwise under ice bath cooling. The reaction was carried out in ice bath for 1 hour, and LC-MS monitoring showed that the reaction was complete. Water was added to the reaction system, washed 3 times with dichloromethane, the organic phase was dried, concentrated to dryness, and the residue was purified by column chromatography to obtain the title compound (225 mg).

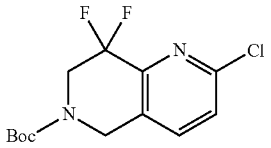 [SMILES: CC(C)(C)OC(=O)N1Cc2ccc(Cl)nc2C(F)(F)C1]

MS (ESI) m/z $(M+H)^+$=304.0.

Step 2: Preparation of Tert-butyl 2-(di-tert-butoxyphosphoryl)-8,8-difluoro-7,8-dihydro-1,6-naphthyridin-6(5H)-carboxylate Tert-butyl 2-chloro-8,8-difluoro-7,8-dihydro-1,6-naphthyridin-6(5H)-carboxylate (100 mg) was weighed into a dry reaction flask, dissolved in toluene (10 mL), added with 1,1'-ferrocenediyl-bis(diphenylphosphino)palladium dichloride dichloromethane adduct (54 mg), triethylamine (0.09 mL) and di-tert-butyl phosphonate (128 mg), purged with nitrogen 3 times, heated to 100° C. and reacted overnight. LC-MS monitoring showed that the reaction was complete, and the reaction mixture was concentrated to dryness. The residue was purified by column chromatography to obtain the title compound (100 mg).

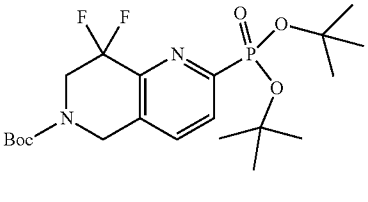 [SMILES: CC(C)(C)OC(=O)N1Cc2ccc(P(=O)(OC(C)(C)C)OC(C)(C)C)nc2C(F)(F)C1]

MS (ESI) m/z $(M+H)^+$=463.2.

Step 3: Preparation of (8,8-difluoro-5,6,7,8-tetrahydro-1,6-naphthyridin-2-yl)phosphonic Acid Hydrochloride Tert-butyl 2-(di-tert-butoxyphosphoryl)-8,8-difluoro-7,8-dihydro-1,6-naphthyridin-6(5H)-carboxylate (100 mg) was weighed and dissolved in dichloromethane (3 mL). 4M HCl in 1,4-dioxane (3 mL) was added dropwise, stirred at room temperature for 1 hour, and LCMS monitoring showed that the reaction was complete. The solvent was evaporated under reduced pressure. The residue was purified by preparative HPLC to obtain the title compound (20 mg).

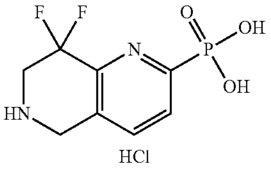 [SMILES: O=P(O)(O)c1ccc2c(n1)C(F)(F)CNC2 ; Cl]

MS (ESI) m/z $(M+H)^+$=250.9.

$^1$H NMR (400 MHz, Deuterium Oxide) δ 7.89 (ddd, J=23.5, 8.2, 4.8 Hz, 2H), 4.57 (s, 2H), 4.08 (t, J=11.6 Hz, 2H.

Example 6: Preparation of (5,6,7,8-tetrahydro-1,6-naphthyridin-2-yl) Phosphonic Acid Monohydrate

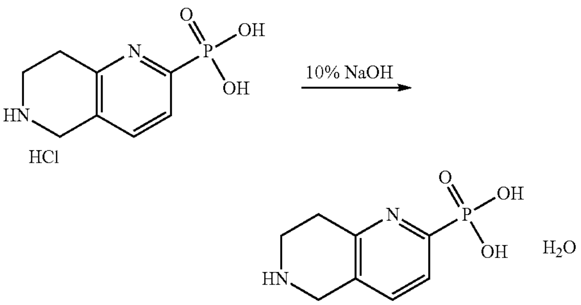

(5,6,7,8-Tetrahydro-1,6-naphthyridin-2-yl) phosphonic acid hydrochloride was dissolved in 5 times the volume of water, the pH value was adjusted to about 4.2 with 10% sodium hydroxide. A solid precipitated, which was filtered and dried to obtain the title compound.

MS (ESI) m/z $(M+H)^+$=215.0.

$^1$H NMR (400 MHz, Methanol-d4) δ 7.72 (dd, J=8.0, 5.6 Hz, 1H), 7.37 (dd J=8.0,3.6 Hz, 1H), 3.98 (s, 2H), 3.19 (t, J=6.0 Hz, 2H), 2.98 (t, J=6.0 Hz, 2H).

Example 7: Preparation of (8-morpholino-5,6,7,8-tetrahydro-1,6-naphthyridin-2-yl) Phosphonic Acid Hydrochloride

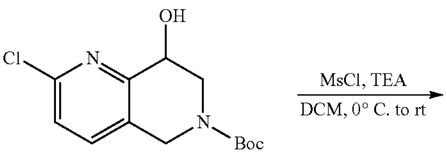

-continued

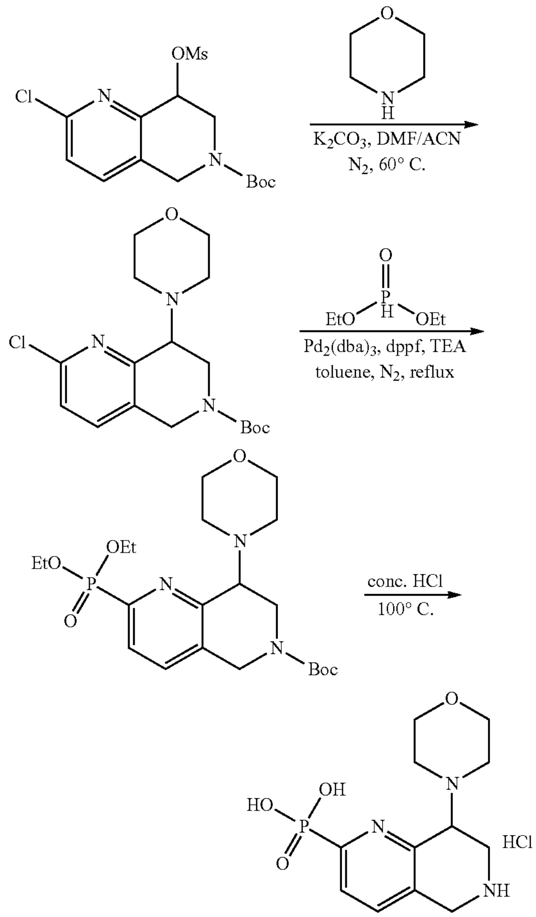

Step 1: Preparation of Tert-butyl 2-chloro-8-((methylsulfonyl)oxy)-7,8-dihydro-1,6-naphthyridin-6(5H)-carboxylate Tert-butyl 2-chloro-8-hydroxy-7,8-dihydro-1,6-naphthyridin-6(5H)-carboxylate (0.14 g) was weighed and dissolved in dichloromethane (10 mL), and triethylamine (0.15 g) and methanesulfonyl chloride (0.11 g) were added successively. The reaction was carried out at room temperature for 1 hour, and TLC showed substantial completion of the reaction. The reaction was quenched by addition of water (10 mL), the layers were separated, the organic phase was combined, dried over anhydrous sodium sulfate, concentrated to dryness under reduced pressure, and the residue was purified by column chromatography to obtain the title compound (0.16 g).

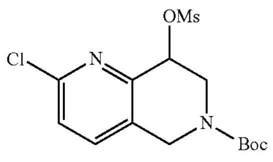 [SMILES: CC(C)(C)OC(=O)N1Cc2ccc(Cl)nc2C(OS(C)(=O)=O)C1]

MS (ESI) m/z $(M+H)^+$=363.1.

Step 2: Preparation of Tert-butyl 2-chloro-8-morpholino-7,8-dihydro-1,6-naphthyridin-6(5H)-carboxylate Tert-butyl 2-chloro-8-((methanesulfonyl)oxy)-7,8-dihydro-1,6-naphthyridin-6(5H)-carboxylate (0.16 g) was weighed and dissolved in acetonitrile (3 mL) and N,N-dimethylformamide (3 mL), potassium carbonate (0.12 g), morpholine (0.12 g) were added, purged with nitrogen three times, reacted overnight at 60° C., and LCMS monitoring showed that the reaction was complete. Acetonitrile was removed by concentration, water (10 mL) and ethyl acetate (10 mL) were added, the layers were separated, the organic phase was dried and concentrated, and the crude product was purified by column chromatography to obtain the title compound (0.11 g).

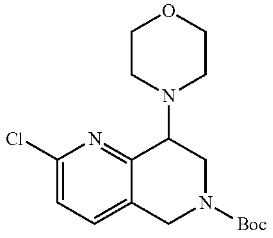 [SMILES: CC(C)(C)OC(=O)N1Cc2ccc(Cl)nc2C(N2CCOCC2)C1]

MS (ESI) m/z $(M+H)^+$=354.1.

Step 3: Preparation of Tert-butyl 2-(diethoxyphosphoryl)-8-morpholino-7,8-dihydro-1,6-naphthyridin-6(5H)-carboxylate Tert-butyl 2-chloro-8-morpholino-7,8-dihydro-1,6-naphthyridin-6(5H)-carboxylate (0.11 g) was weighed and dissolved in toluene (3 mL), and diethyl phosphite (86 mg), tris(dibenzylideneacetone)dipalladium (57 mg), 1,1'-bis(diphenylphosphino)ferrocene (69 mg), and triethylamine (62 mg) were added successively. Purged with nitrogen three times and reacted overnight at 120° C. under nitrogen atmosphere, LCMS showed substantial completion of the reaction. Concentrated to dryness under reduced pressure and purified by column chromatography to obtain the title compound (0.12 g).

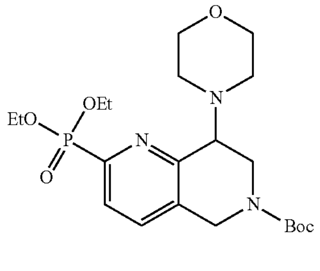 [SMILES: CCOP(=O)(OCC)c1ccc2c(n1)C(N1CCOCC1)CN(C(=O)OC(C)(C)C)C2]

MS (ESI) m/z $(M+H)^+$=456.2.

Step 4: Preparation of (8-morpholino-5,6,7,8-tetrahydro-1,6-naphthyridin-2-yl) Phosphonic Acid Hydrochloride Tert-butyl 2-(diethoxyphosphoryl)-8-morpholino-7,8-dihydro-1,6-naphthyridin-6(5H)-carboxylate (60 mg) was weighed, concentrated hydrochloric acid (4 mL) was added, the reaction was carried in a sealed tube at 100° C. for 2 hours, and TLC showed substantial completion of the reaction. The mixture was concentrated to dryness and the residue was purified by pre-HPLC to obtain the title compound (11.7 mg).

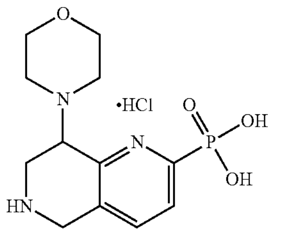 [SMILES: O=P(O)(O)c1ccc2c(n1)C(N1CCOCC1)CNC2 ; Cl]

MS (ESI) m/z $(M+H)^+$=300.1.

$^1$H NMR (400 MHZ, Deuterium Oxide) δ 7.70 (m, 2H), 5.14 (dd, J=10.5, 6.3 Hz, 1H), 4.56-4.43 (m, 2H), 4.19 (dd, J=12.7, 6.2 Hz, 1H), 3.98 (s, 4H), 3.90-3.81 (m, 1H), 3.40 (s, 2H), 3.27 (s, 2H).

Example 8: Preparation of (8-hydroxy-5,6,7,8-tetrahydro-1,6-naphthyridin-2-yl) Phosphonic Acid Hydrochloride

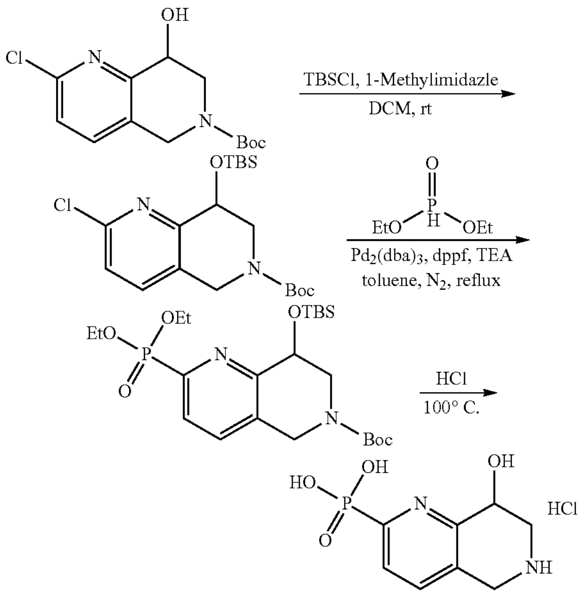

Step 1. Preparation of Tert-butyl 8-((tert-butyldimethylsilyl)oxy)-2-chloro-7,8-dihydro-1,6-naphthyridin-6(5H)-carboxylate Tert-butyl 2-chloro-8-hydroxy-7,8-dihydro-1,6-naphthyridin-6(5H)-carboxylate (0.16 g) was weighed and dissolved in dichloromethane (10 mL), and 1-methyl-1H-imidazole (92 mg) and tert-butyldimethylsilyl chloride (0.12 g) were added successively. The reaction was carried out at room temperature for 2 hours and TLC showed substantial completion of the reaction. Concentrated to dryness under reduced pressure and purified by column chromatography to obtain the title compound (0.20 g).

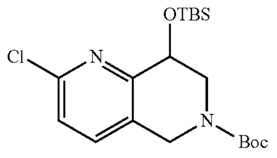 [SMILES: CC(C)(C)OC(=O)N1Cc2ccc(Cl)nc2C(O[Si](C)(C)C(C)(C)C)C1]

MS (ESI) m/z $(M+H)^+$=399.2.

Step 2: Preparation of Tert-butyl 8-((tert-butyldimethylsilyl)oxy)-2-(diethoxyphosphoryl)-7,8-dihydro-1,6-naphthyridin-6(5H)-car boxylate Tert-butyl 8-((tert-butyldimethylsilyl)oxy)-2-chloro-7,8-dihydro-1,6-naphthyridin-6(5H)-carboxylate (0.20 g) was weighed and dissolved in toluene (10 mL), and diethyl phosphite (138 mg), tris(dibenzylideneacetone)dipalladium (92 mg), 1,1'-bis(diphenylphosphino)ferrocene (110 mg), and triethylamine (101 mg) were added successively. Purged with nitrogen three times and reacted overnight at 110° C. under nitrogen atmosphere, LCMS showed substantial completion of the reaction. Concentrated to dryness under reduced pressure and purified by column chromatography to obtain the title compound (0.16 g).

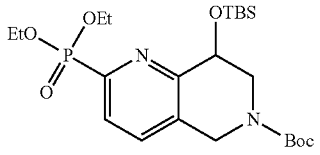 [SMILES: CCOP(=O)(OCC)c1ccc2c(n1)C(O[Si](C)(C)C(C)(C)C)CN(C(=O)OC(C)(C)C)C2]

MS (EST) m/z. $(M+H)^+$=501.3.

Step 3: Preparation of (8-hydroxy-5,6,7,8-tetrahydro-1,6-naphthyridin-2-yl) Phosphonic Acid Hydrochloride Tert-butyl 8-((tert-butyldimethylsilyl)oxy)-2-(diethoxyphosphoryl)-7,8-dihydro-1,6-naphthyridin-6(5H)-car boxylate (70 mg) was weighed, concentrated hydrochloric acid (4 mL) was added, the reaction was carried in a sealed tube at 100° C. for 2 hours, and TLC showed substantial completion of the reaction. The mixture was concentrated to dryness and the residue was purified by pre-HPLC to obtain the title compound (2.4 mg).

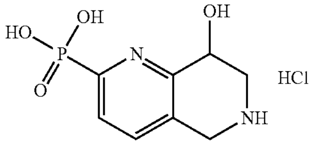 [SMILES: O=P(O)(O)c1ccc2c(n1)C(O)CNC2 ; Cl]

MS (ESI) m/z $(M+H)^+$=231.0.

$^1$H NMR (400 MHZ, Deuterium Oxide) δ 7.71 (s, 2H), 5.00 (s, 1H), 4.40 (s, 2H), 3.59 (s, 2H).

Example 9: Preparation of (8-(2-hydroxyethoxy)-5,6,7,8-tetrahydro-1,6-naphthyridin-2-yl) Phosphonic Acid Hydrochloride

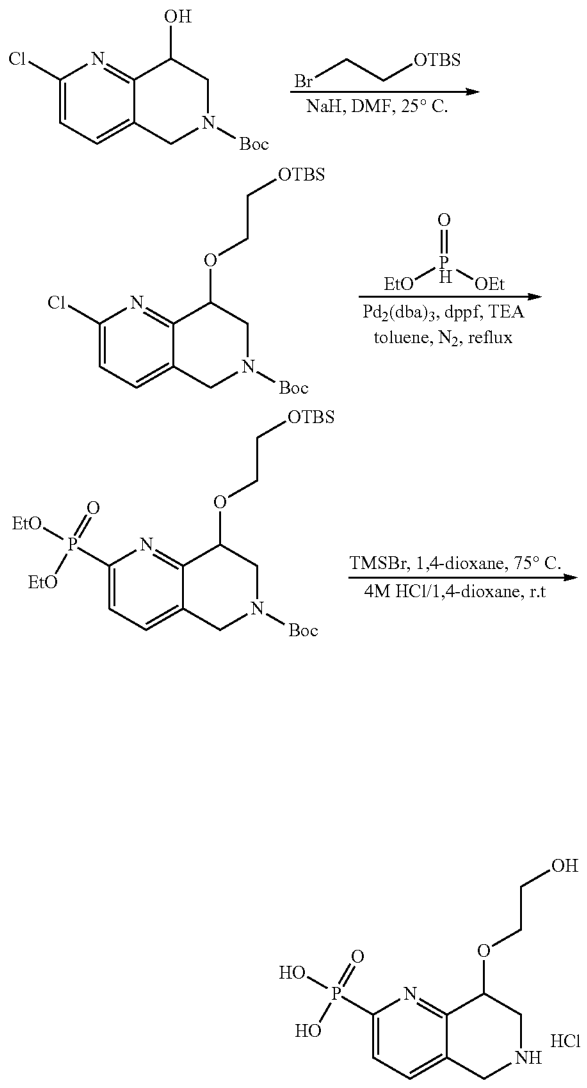

Step 1: Preparation of Tert-butyl 8-(2-((tert-butyldimethylsilyl)oxy)ethoxy)-2-chloro-7,8-dihydro-1,6-naphthyridin-6(5H)-carboxy late Tert-butyl 2-chloro-8-hydroxy-7,8-dihydro-1,6-naphthyridin-6(5H)-carboxylate (0.60 g) was weighed and dissolved in tetrahydrofuran (10 mL), and NaH (1.0 g) was added under ice bath cooling. After stirring for 5 minutes, (2-bromoethoxy)(tert-butyl)dimethylsilane was added and reacted at room temperature for 2 hours, and TLC showed that the reaction was substantially complete. The reaction was quenched by the addition of ice water, extracted with ethyl acetate and water, the layers were separated, the organic phase was combined, dried, concentrated to dryness under reduced pressure, and the residue was purified by column chromatography to obtain the title compound (0.40 g).

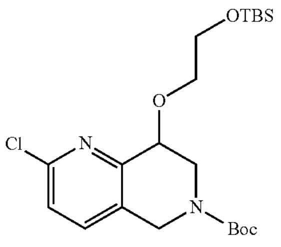 [SMILES: CC(C)(C)OC(=O)N1Cc2ccc(Cl)nc2C(OCCO[Si](C)(C)C(C)(C)C)C1]

MS (ESI) m/z $(M+H)^+$=443.2.

Step 2: Preparation of Tert-butyl 8-(2-((tert-butyldimethylsilyl)oxy)ethoxy)-2-(diethoxyphosphoryl)-7,8-dihydro-1,6-naphthyridin-6(5H)-carboxylate Tert-butyl 8-(2-((tert-butyldimethylsilyl)oxy)ethoxy)-2-chloro-7,8-dihydro-1,6-naphthyridin-6(5H)-carboxy late (0.40 g) was weighed and dissolved in toluene (10 mL), and diethyl phosphite (0.25 g), tris(dibenzylideneacetone)dipalladium (0.17 g), 1,1'-bis(diphenylphosphino)ferrocene (0.20 g), and triethylamine (0.18 g) were added successively. Purged with nitrogen three times and reacted overnight at 110° C. under nitrogen atmosphere, LCMS showed substantial completion of the reaction. Concentrated to dryness under reduced pressure and purified by column chromatography to obtain the title compound (0.44 g).

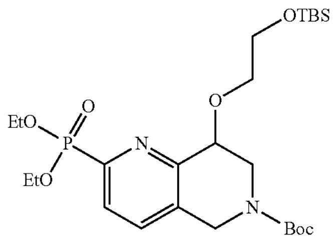 [SMILES: CCOP(=O)(OCC)c1ccc2c(n1)C(OCCO[Si](C)(C)C(C)(C)C)CN(C(=O)OC(C)(C)C)C2]

MS (ESI) m/z $(M+H)^+$=545.3.

Step 3: Preparation of (8-(2-hydroxyethoxy)-5,6,7,8-tetrahydro-1,6-naphthyridin-2-yl)phosphonic Acid Hydrochloride Tert-butyl 8-(2-((tert-butyldimethylsilyl)oxy)ethoxy)-2-(diethoxyphosphoryl)-7,8-dihydro-1,6-naphthyridin-6(5H)-carboxylate (70 mg) was weighed and dissolved in 1,4-dioxane (5 mL). 1 M trimethylsilyl bromide (0.2 mL) was added, refluxed overnight at 75° C., and LCMS monitoring showed substantial completion of the reaction. The mixture was concentrated to dryness, dissolved in 4M HCl in 1,4-dioxane, reacted at room temperature for 2 hours, and LCMS monitoring showed substantial completion of the reaction. Concentrated to dryness, and the crude product was purified by pre-HPLC to obtain the title compound (30.0 mg).

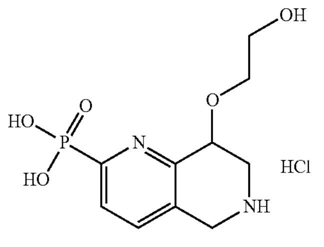 [SMILES: O=P(O)(O)c1ccc2c(n1)C(OCCO)CNC2 ; Cl]

MS (ESI) m/z $(M+H)^+$=275.0.

$^1H$ NMR (400 MHZ, Deuterium Oxide) δ 7.79 (d, J=5.0 Hz, 2H), 4.77 (s, 1H), 4.43 (q, J=16.5 Hz, 2H), 3.93 (d, J=13.5 Hz, 1H), 3.84-3.78 (m, 1H), 3.77-3.70 (m, 1H), 3.63 (t, J=4.4 Hz, 2H), 3.49 (d, J=13.6 Hz, 1H).

Example 10: Preparation of (8-oxidothiomorpholino-5,6,7,8-tetrahydro-1,6-naphthyridin-2-yl) Phosphonic Acid Hydrochloride

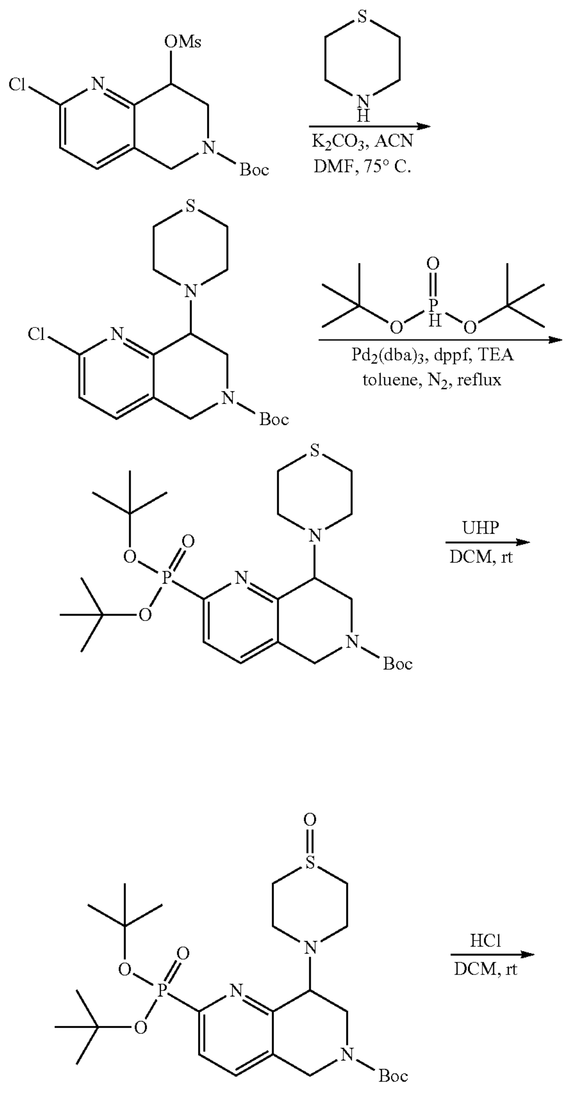

-continued

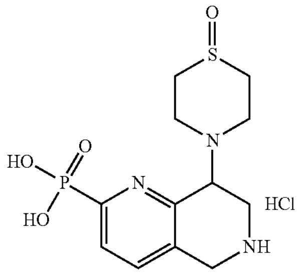

Step 1: Preparation of Tert-butyl 2-chloro-8-thiomorpholino-7,8-dihydro-1,6-naphthyridin-6(5H)-carboxylate Tert-butyl 2-chloro-8-((methanesulfonyl)oxy)-7,8-dihydro-1,6-naphthyridin-6(5H)-carboxylate (0.30 g) was weighed and dissolved in acetonitrile (5 mL), and N,N-dimethylformamide (5 mL), potassium carbonate (0.12 g), thiomorpholine (0.12 g) were added, purged with nitrogen three times, reacted overnight at 60° C., and LCMS monitoring showed that the reaction was complete. Acetonitrile was removed by concentration, water (10 mL) was added and extracted with ethyl acetate (10 mL), the layers were separated, the organic phase was dried and concentrated, and the crude product was purified by column chromatography to obtain the title compound (0.12 g).

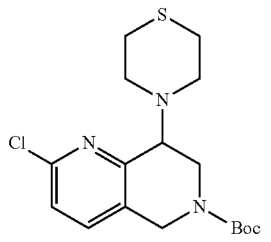 [SMILES: CC(C)(C)OC(=O)N1Cc2ccc(Cl)nc2C(N2CCSCC2)C1]

MS (ESI) m/z $(M+H)^+$=370.1.

Step 2: Preparation of Tert-butyl 2-(di-tert-butoxyphosphoryl)-8-thiomorpholino-7,8-dihydro-1,6-naphthyridin-6(5H)-carboxylate Tert-butyl 2-chloro-8-thiomorpholino-7,8-dihydro-1,6-naphthyridin-6(5H)-carboxylate (0.23 g) was weighed and dissolved in toluene (10 mL), and di-tert-butyl phosphite (242 mg), tris(dibenzylideneacetone)dipalladium (114 mg), 1,1'-bis(diphenylphosphino)ferrocene (138 mg), and triethylamine (130 mg) were added successively. Purged with nitrogen three times and reacted overnight at 120° C. under nitrogen atmosphere, LCMS showed substantial completion of the reaction. Concentrated to dryness under reduced pressure and purified by column chromatography to obtain the title compound (0.24 g).

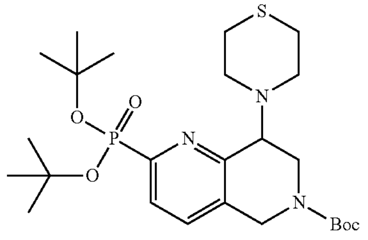 [SMILES: CC(C)(C)OC(=O)N1Cc2ccc(P(=O)(OC(C)(C)C)OC(C)(C)C)nc2C(N2CCSCC2)C1]

MS (ESI) m/z $(M+H)^+$=528.2

Step 3: Preparation of Tert-butyl 2-(di-tert-butoxyphosphoryl)-8-(1-oxidothiomorpholino)-7,8-dihydro-1,6-naphthyridin-6(5H)-carboxylate Tert-butyl 2-(di-tert-butoxyphosphoryl)-8-thiomorpholino-7,8-dihydro-1,6-naphthyridin-6(5H)-carboxylate (90 mg) was weighed and dissolved in acetic acid (2 mL), urea peroxide (242 mg) was added and the reaction was carried out at room temperature for 2 hours, and LCMS showed substantial completion of the reaction. Water (50 mL) was added and extracted with ethyl acetate (10 mL×3 times), the layers were separated, the organic phases were combined, dried over anhydrous sodium sulfate, concentrated to dryness under reduced pressure, and the residue was purified by column chromatography to obtain the title compound (60 mg).

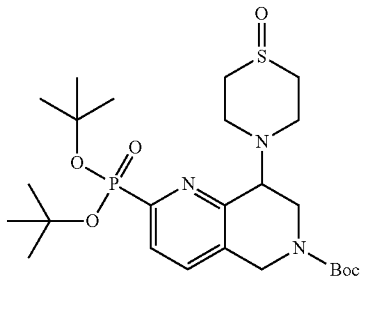 [SMILES: CC(C)(C)OC(=O)N1Cc2ccc(P(=O)(OC(C)(C)C)OC(C)(C)C)nc2C(N2CCS(=O)CC2)C1]

MS (ESI) m/z $(M+H)^+$=544.2

Step 4: Preparation of (8-(1-oxidothiomorpholino)-5,6,7,8-tetrahydro-1,6-naphthyridin-2-yl) Phosphonic Acid Hydrochloride Tert-butyl 2-(di-tert-butoxyphosphoryl)-8-(1-oxidothiomorpholino)-7,8-dihydro-1,6-naphthyridin-6(5H)-carboxylate (60 mg) was weighed and dissolved in dichloromethane (4 mL), concentrated hydrochloric acid (0.1 mL) was added under cooling in ice bath, and the reaction was carried out for 0.5 h in ice bath, TLC showed substantial completion of the reaction. The mixture was concentrated to dryness and separated by pre-HPLC to obtain the title compound (2.94 mg).

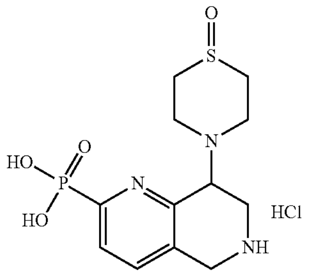 [SMILES: O=S1CCN(C2CNCc3ccc(P(=O)(O)O)nc32)CC1 ; Cl]

MS (ESI) m/z $(M+H)^+$=332.0.

$^1$H NMR (400 MHZ, Deuterium Oxide) δ 7.96 (m, 1H), 7.88 (m, 1H), 5.09 (dd, J=10.8, 6.0 Hz, 1H), 4.61-4.49 (m, 2H), 4.20 (dd, J=12.7, 6.0 Hz, 1H), 3.88 (m, 2H), 3.68-3.58 (m, 2H), 3.37-3.23 (m, 3H), 3.18-3.02 (m, 2H).

Example 11: Preparation of (7-isobutyl-5,6,7,8-tetrahydro-1,6-naphthyridin-2-yl) Phosphonic Acid Hydrochloride

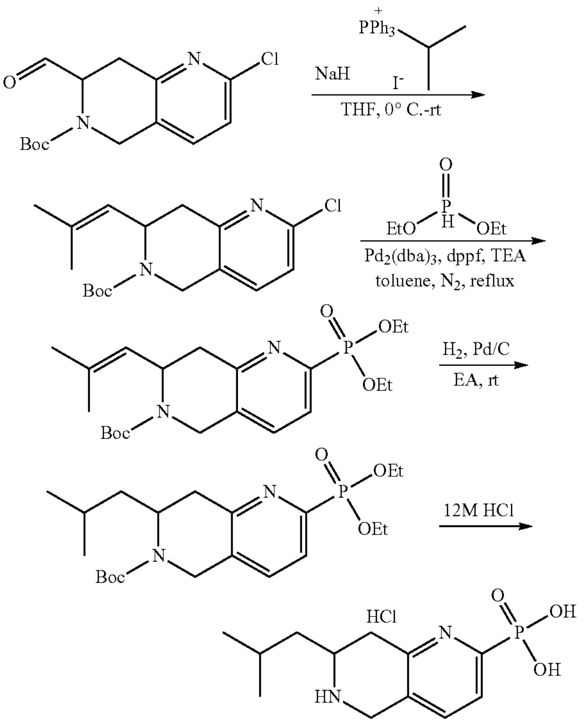

Step 1: Preparation of 2-chloro-7-(2-methylprop-1-en-1-yl)-7,8-dihydro-1,6-naphthyridin-6(5H)-carboxylate tert-butyl Isopropyltriphenylphosphonium iodide (2.918 g) was weighed and dissolved in N,N-dimethylformamide (10 mL), sodium hydride (0.27 g) was added, purged with nitrogen 3 times, reaction was carried out at 0° C. for 20 minutes, and tert-butyl 2-chloro-7-formyl-7,8-dihydro-1,6-naphthyridin-6(5H)-carboxylate (1 g) was added. The reaction was carried out for 3 hours. After the completion of the reaction as monitored by LC-MS, the system was quenched with saturated ammonium chloride solution, extracted 3 times with ethyl acetate, the organic phase was dried, concentrated to dryness, and the residue was purified by column chromatography to obtain the title compound (280 mg).

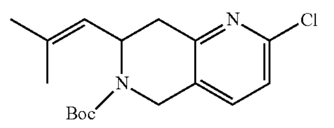 [SMILES: CC(C)=CC1Cc2nc(Cl)ccc2CN1C(=O)OC(C)(C)C]

MS (ESI) m/z $(M+H)^+$=323.1.

Step 2: Preparation of Tert-butyl 2-(diethoxyphosphoryl)-7-(2-methylprop-1-en-1-yl)-7,8-dihydro-1,6-naphthyridin-6(5H)-carboxylate Tert-butyl 2-chloro-7-(2-methylprop-1-en-1-yl)-7,8-dihydro-1,6-naphthyridin-6(5H)-carboxylate (280 mg) was weighed into a dry reaction flask, dissolved in toluene (10 mL), tris(dibenzylideneacetone) dipalladium (124.5 mg), 1,1'-ferrocenediyl-bis(diphenylphosphine) (192.7 mg), triethylamine (0.0.24 mL) and diethyl phosphonate (240 mg) were added, purged with nitrogen 3 times, heated to 110° C. and reacted for 4 hours. LC-MS monitoring showed that the reaction was complete, and the reaction mixture was concentrated to dryness. The residue was purified by column chromatography to obtain the title compound (300 mg).

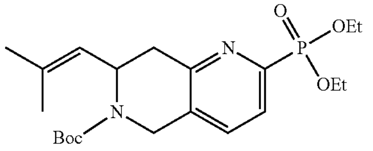 [SMILES: CCOP(=O)(OCC)c1ccc2c(n1)CC(C=C(C)C)N(C(=O)OC(C)(C)C)C2]

MS (ESI) m/z $(M+H)^+$=425.2.

Step 3: Preparation of Tert-butyl 2-(diethoxyphosphoryl)-7-isobutyl-7,8-dihydro-1,6-naphthyridin-6 (5H)-carboxylate Tert-butyl 2-(diethoxyphosphoryl)-7-(2-methylprop-1-en-1-yl)-7,8-dihydro-1,6-naphthyridin-6(5H)-carboxylate (300 mg) was weighed and dissolved in methanol (15 mL). Hydrogen was introduced into the autoclave, heated to 40° C. and stirred overnight, and LCMS monitoring showed that the reaction was complete. Filtered through Celite and the solvent was evaporated under reduced pressure. The residue was purified by column chromatography to obtain the title compound (90 mg).

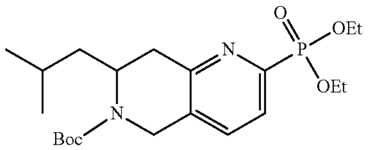 [SMILES: CCOP(=O)(OCC)c1ccc2c(n1)CC(CC(C)C)N(C(=O)OC(C)(C)C)C2]

MS (EST) m/z $(M+H)^+$=427.

Step 4: Preparation of (7-isobutyl-5,6,7,8-tetrahydro-1,6-naphthyridin-2-yl) Phosphonic Acid Hydrochloride Tert-butyl 2-(diethoxyphosphoryl)-7-isobutyl-7,8-dihydro-1,6-naphthyridin-6(5H)-carboxylate (90 mg) was weighed and dissolved in 12M hydrochloric acid solution (5 mL), heated to 100° C. and stirred for 3 hours. LCMS monitoring showed that the reaction was complete. The solvent was removed by evaporation under reduced pressure, and the residue was purified by pre-HPLC to obtain the title compound (50 mg).

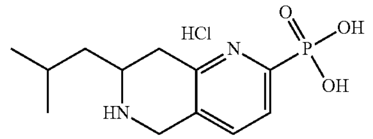 [SMILES: CC(C)CC1Cc2nc(P(=O)(O)O)ccc2CN1 ; Cl]

MS (ESI) m/z $(M+H)^+$=271.1.

$^1$H NMR (400 MHz, Deuterium Oxide) δ 7.71 (dd, J=7.9, 3.7 Hz, 1H), 7.64 (t, J=7.0 Hz, 1H), 4.39 (s, 2H), 3.70 (q, J=10.7, 7.9 Hz, 1H), 3.32 (dd, J=18.4, 4.7 Hz, 1H), 2.94 (dd, J=18.1, 10.7 Hz, 1H), 1.75 (dt, J=13.4, 6.8 Hz, 1H), 1.59 (t, J=7.2 Hz, 2H), 0.85 (dd, J=12.3, 6.4 Hz, 6H).

Example 12: Preparation of (7-propyl-5,6,7,8-tetrahydro-1,6-naphthyridin-2-yl) Phosphonic Acid Hydrochloride

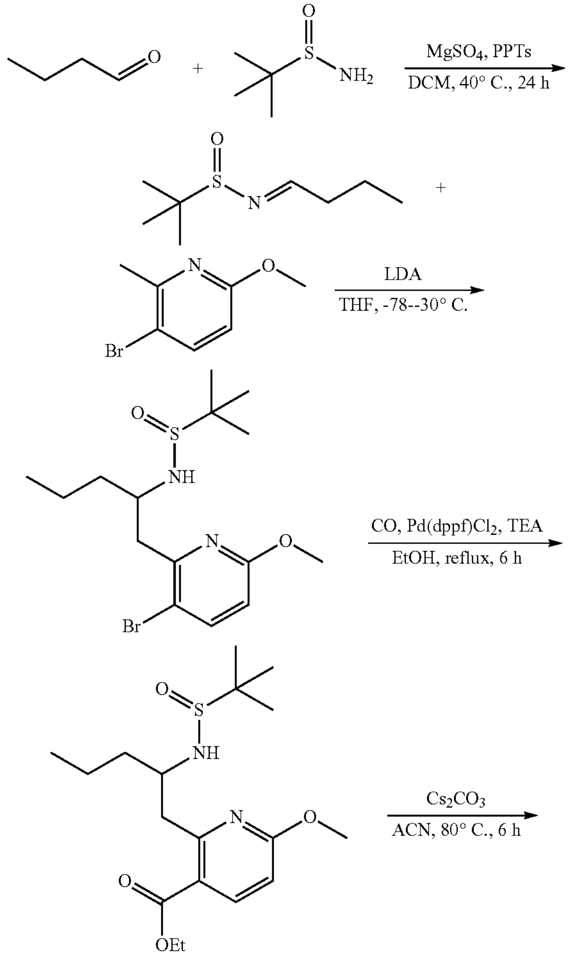

-continued

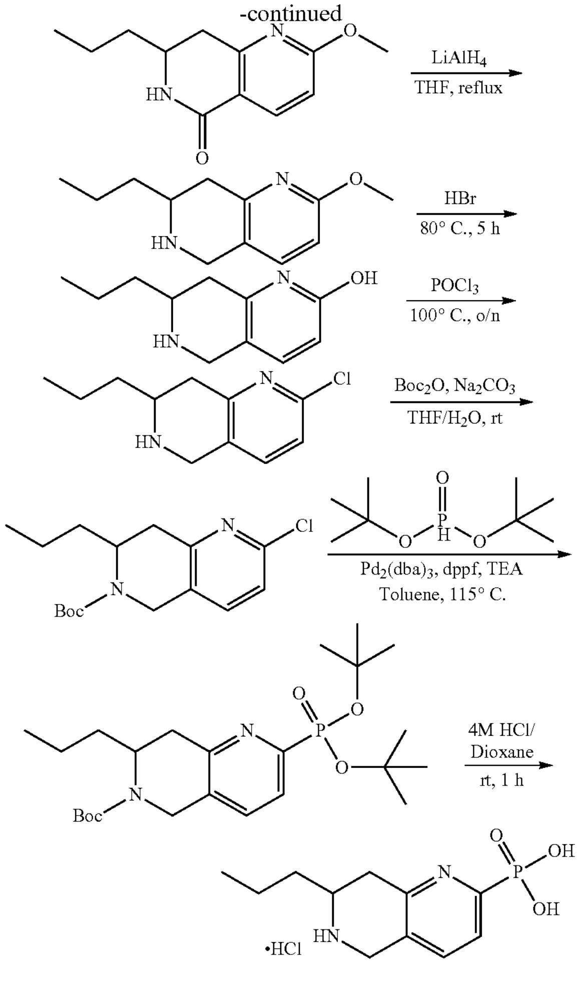

Step 1: Preparation of 2-methyl-N-(4-butylidene)propane-2-sulfinamide

Butyraldehyde (10 g) was weighed and dissolved in methylene chloride (100 mL), and 2-methylpropane-2-sulfinamide (20 g), anhydrous magnesium sulfate (83.3 g) and pyridinium 4-methylbenzenesulfonate (1.74 g) were added successively. The mixture was heated to 40° C. for 24 hours and the reaction was monitored by LC-MS for completion. The reaction mixture was cooled to room temperature, filtered under suction, the filter cake was washed with dichloromethane, the filtrate was concentrated to dryness, and the residue was purified by column chromatography to obtain the title compound (22.4 g).

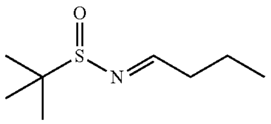

MS (ESI) m/z (M+H)$^+$=176.1

Step 2: Preparation of N-(1-(3-bromo-6-methoxy-pyridin-2-yl)-5-butan-2-yl)-2-methylpropane-2-sulfinamide 3-Bromo-6-methoxy-2-methylpyridine (10 g) was weighed into a dry reaction flask, anhydrous tetrahydrofuran (80 mL) was injected under nitrogen atmosphere, and the temperature was lowered to −78° C. A solution of lithium diisopropylamide in tetrahydrofuran (27.2 mL, 2.0M) was added dropwise and the reaction was carried out at −78° C. for 40 min. A solution of 2-methyl-N-(4-butylidene)-propane-2-sulfinamide (9.53 g) in tetrahydrofuran (20 mL) was added dropwise, reacted at −30° C. for 30 minutes, and warmed to room temperature slowly. LCMS monitoring showed that the reaction was complete. The reaction was quenched with saturated ammonium chloride solution, water and ethyl acetate were added, the layers were separated and extracted, the organic phase was concentrated to dryness, and the residue was purified by column chromatography to obtain the title compound (6.4 g).

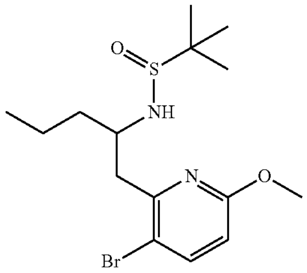 [SMILES: CCCC(Cc1nc(OC)ccc1Br)NS(=O)C(C)(C)C]

MS (ESI) m/z (M+H)$^+$=377.1.

Step 3: Preparation of Ethyl 2-(2-((tert-butylsulfinyl)amino)-5-butyl)-6-methoxynicotinate N-(1-(3-bromo-6-methoxypyridin-2-yl)-5-butan-2-yl)-2-methylpropane-2-sulfinamide (6.4 g) was weighed and dissolved in ethanol (80 mL), and [1,1'-bis(diphenylphosphino) ferrocene] dichloropalladium (2.48 g) and N,N-diisopropylethylamine (5.6 mL) were added. After the completion of addition, the system was purged with carbon monoxide and stirred under a carbon monoxide atmosphere at 100° C. for 24 hours. LCMS monitoring showed that the reaction was complete. The solvent was evaporated under reduced pressure and the residue was purified by column chromatography to obtain the title compound (4 g).

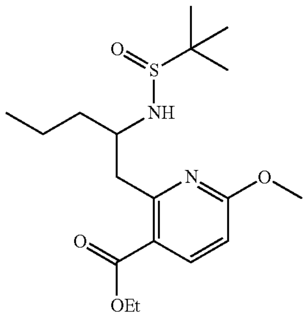 [SMILES: CCCC(Cc1nc(OC)ccc1C(=O)OCC)NS(=O)C(C)(C)C]

MS (ESI) m/z (M+H)$^+$=371.1.

Step 4: Preparation of 2-methoxy-7-(3-propyl)-7,8-dihydro-1,6-naphthyridin-5(6H)-one Ethyl 2-(2-((tert-butylsulfinyl)amino)-5-butyl)-6-methoxynicotinate (4 g) was weighed and dissolved in acetonitrile (100 mL) and cesium carbonate (17.6 g) was added. The temperature was raised to 80° C. and stirred overnight, and the reaction was monitored by LC-MS for completion. The reaction was cooled to room temperature, filtered under suction, the filter cake was washed with dichloromethane, the filtrate was concentrated to dryness, and the residue was purified by column chromatography to obtain the title compound (2.55 g).

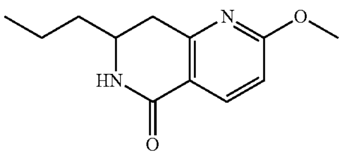 [SMILES: CCCC1Cc2nc(OC)ccc2C(=O)N1]

MS (ESI) m/z $(M+H)^+$=221.1.

Step 5: Preparation of 2-methoxy-7-(3-propyl)-5,6,7,8-tetrahydro-1,6-naphthyridine 2-Methoxy-7-(3-propyl)-7,8-dihydro-1,6-naphthyridin-5(6H)-one (2.55 g) was weighed, dissolved in tetrahydrofuran (100 mL), added with lithium aluminum hydride (2.6 g) under ice bath cooling, stirred at 70° C. for 8 hours and monitored by LC-MS for completion of the reaction. under ice bath cooling, water (2.6 mL), sodium hydroxide solution (15%, 2.6 mL) and water (7.8 mL) were added dropwise successively. After the completion of addition, the mixture was stirred at room temperature for 20 minutes, dried over anhydrous magnesium sulfate, filtered under suction, the filter cake was washed with dichloromethane, and filtrate was concentrated to dryness under reduced pressure. The residue was purified by column chromatography to obtain the title compound (1.9 g).

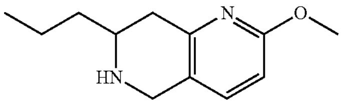

MS (ESI) m/z $(M+H)^+$=211.1.

Step 6: Preparation of 7-(3-propyl)-5,6,7,8-tetrahydro-1,6-naphthyridin-2-ol

2-Methoxy-7-(3-propyl)-5,6,7,8-tetrahydro-1,6-naphthyridine (1.9 g) was weighed, a solution of hydrobromic acid in acetic acid (5 mL) was added, the mixture was stirred at 80° C. for 5 hours, and the reaction was monitored by LC-MS for completion. The solvent was removed under reduced pressure, ethyl acetate was added and slurried, filtered and dried to obtain the crude title compound (1.5 g).

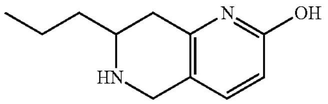

MS (EST) m/z $(M+H)^+$=193.1.

Step 7: Preparation of 2-chloro-7-(3-propyl)-5,6,7,8-tetrahydro-1,6-naphthyridine To 7-(3-Propyl)-5,6,7,8-tetrahydro-1,6-naphthyridin-2-ol (0.5 g) was added phosphorus oxychloride (10 mL), and the mixture was heated to 100° C. and stirred for 4 hours. The reaction was monitored by LC-MS for completion. The solvent was removed under reduced pressure and ice water and dichloromethane were added to afford the crude title compound.

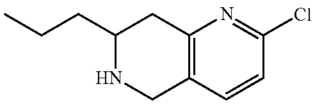

MS (ESI) m/z $(M+H)^+$=211.1.

Step 8: Preparation of Tert-butyl 2-chloro-7-(3-propyl)-7,8-dihydro-1,6-naphthyridin-6-(5H)-carboxylate The pH of the work-up system of Step 7 was adjusted to 8-9 with sodium carbonate solution, and di-tert-butyl dicarbonate (1.29 mL) was added. After stirring at room temperature for 1 hour, the reaction was complete as monitored by LC-MS. Concentrated to dryness under reduced pressure and the residue was purified by column chromatography to obtain the title compound (0.5 g).

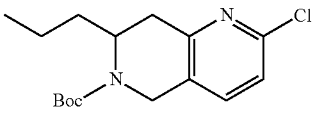 [SMILES: CCCC1Cc2nc(Cl)ccc2CN1C(=O)OC(C)(C)C]

MS (ESI) m/z $(M+H)^+$=311.1.

Step 9: Preparation of Tert-butyl 2-(di-tert-butoxyphosphoryl)-7-propyl-7,8-dihydro-1,6-naphthyridin-6(5H)-carboxylate Tert-butyl 2-chloro-7-(3-propyl)-7,8-dihydro-1,6-naphthyridin-6-(5H)-carboxylate (93 mg) was weighed into a dry reaction flask, dissolved in toluene (10 mL), and tris(dibenzylideneacetone)dipalladium (55 mg), 1,1'-bis(diphenylphosphino)ferrocene (67 mg), triethylamine (61 mg), di-tert-butyl phosphonate (120 mg) were added, and the system was purged with nitrogen 3 times and heated to 115° C. The reaction was carried out overnight. The reaction was complete as monitored by LC-MS, and the reaction mixture was concentrated to dryness under reduced pressure. The residue was purified by column chromatography to obtain the title compound (105 mg).

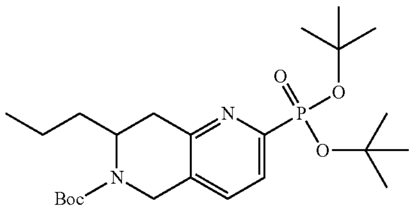 [SMILES: CCCC1Cc2nc(P(=O)(OC(C)(C)C)OC(C)(C)C)ccc2CN1C(=O)OC(C)(C)C]

MS (ESI) m/z $(M+H)^+$=469.2.

Step 10: Preparation of (7-propyl-5,6,7,8-tetrahydro-1,6-naphthyridin-2-yl)phosphonic Acid Hydrochloride Tert-butyl 2-(di-tert-butoxyphosphoryl)-7-propyl-7,8-dihydro-1,6-naphthyridin-6(5H)-carboxylate (105 mg) was weighed and dissolved in dichloromethane (4 mL), 4M HCl in 1.4-dioxane (4 mL) was added dropwise, stirred at room temperature for 1 hour, LC-MS monitoring showed that the reaction was complete. The solvent was evaporated under reduced pressure, and the residue was purified by pre-HPLC to obtain the title compound (8 mg).

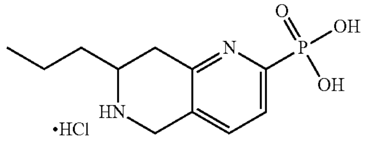 [SMILES: CCCC1Cc2nc(P(=O)(O)O)ccc2CN1 ; Cl]

MS (ESI) m/z $(M+H)^+$=257.0.

$^1$H NMR (400 MHZ, Deuterium Oxide) δ 7.75 (dd, J=8.0, 3.8 Hz, 1H), 7.68 (dd, J=7.9, 6.2 Hz, 1H), 4.43 (s, 2H), 3.67 (ddd, J=10.9, 5.3, 2.1 Hz, 1H), 3.34 (dd, J=18.2, 4.8 Hz, 1H), 3.01 (dd, J=18.2, 10.8 Hz, 1H), 1.74 (dtd, J=14.7, 8.5, 6.7 Hz, 2H), 1.52-1.35 (m, 2H), 0.88 (t, J=7.3 Hz, 3H).

Example 13: Preparation of (7-phenylethyl-5,6,7,8-tetrahydro-1,6-naphthyridin-2-yl) Phosphonic Acid Hydrochloride

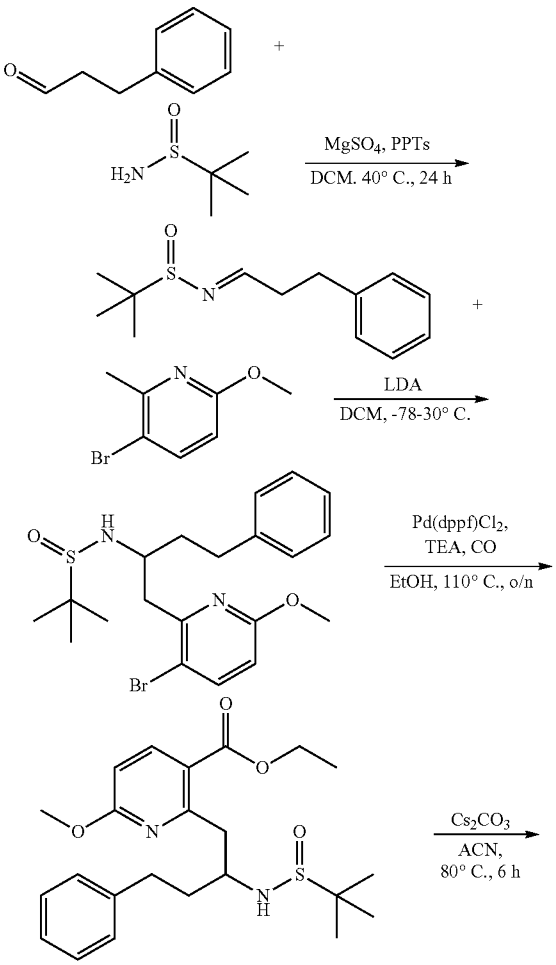

-continued

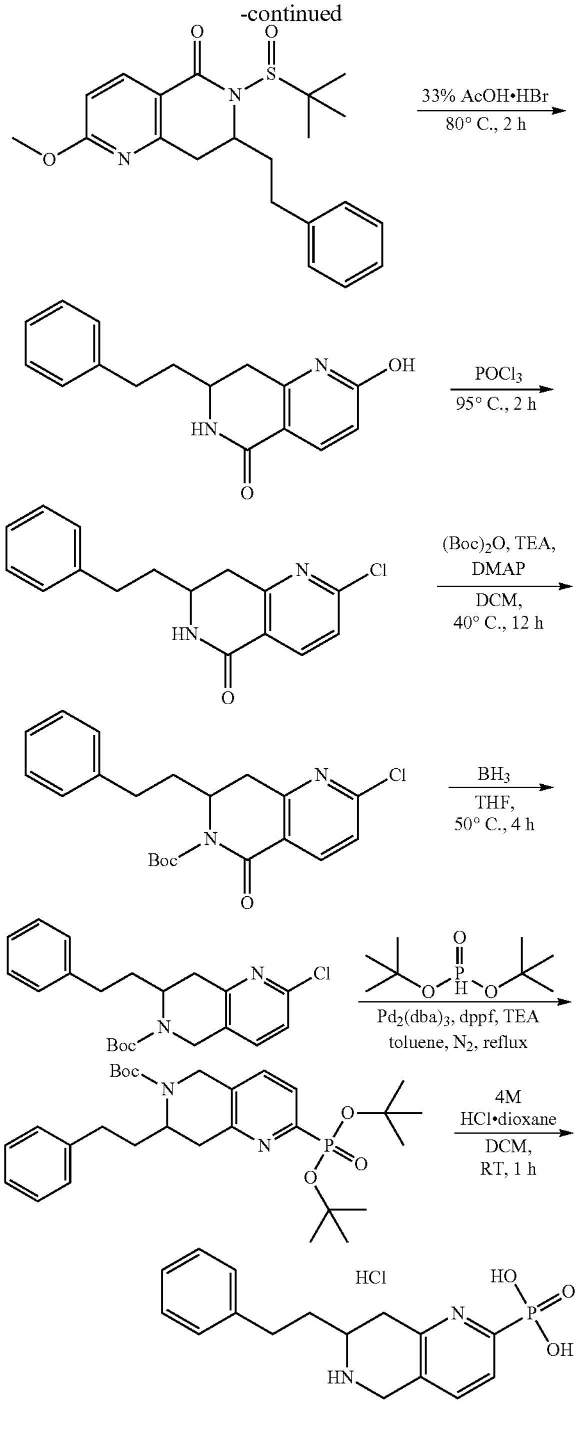

Step 1: Preparation of 2-methyl-N-(3-phenylpropylidene)propane-2-sulfinamide 3-Phenylpropanal (10.73 g) was weighed and dissolved in methylene chloride (120 mL), magnesium sulfate (41.2 g), pyridinium 4-methylbenzenesulfonate (1.0 g), and 2-methylpropane-2-sulfinamide (10.7 g) were added. After the completion of addition, the system was purged with nitrogen 3 times, and the reaction was refluxed overnight. After the reaction was complete as monitored by LC-MS, the system was filtered with suction, washed with ethyl acetate for 3 times, the organic phase was dried, concentrated to dryness, and the residue was purified by column chromatography to obtain the title compound (12.44 g).

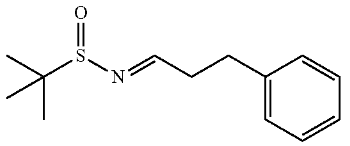 [SMILES: CC(C)(C)S(=O)/N=C/CCc1ccccc1]

MS (ESI) m/z $(M+H)^+$=338.1.

Step 2: Preparation of N-(1-(3-bromo-6-methoxypyridin-2-yl)-4-phenylbutan-2-yl)-2-methylpropane-2-sulfinamide Tetrahydrofuran (25 mL) was added into a dry reaction flask, purged with nitrogen 3 times, 2M lithium diisopropylamide (12.4 mL) was added and the temperature was lowered to −78° C. A solution of 3-bromo-6-methoxy-2-methylpyridine (5 g) in tetrahydrofuran (5 mL) was added and stirred at −78 for 1 hour. A solution of 2-methyl-N-(3-phenylpropylidene)propane-2-sulfinamide (6.45 g) in tetrahydrofuran (15 ml) was added and the mixture was stirred for 2 hours, with the temperature slowly raised from −78° C. to −30° C. LC-MS monitoring showed that the reaction was complete, and the system was quenched with saturated ammonium chloride solution, extracted 3 times with ethyl acetate, the organic phase was dried, concentrated to dryness, and the residue was purified by column chromatography to obtain the title compound (6.4 g).

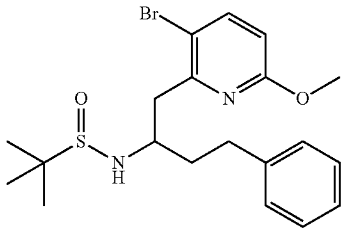 [SMILES: COc1ccc(Br)c(CC(CCc2ccccc2)NS(=O)C(C)(C)C)n1]

MS (ESI) m/z $(M+H)^+$=439.1

Step 3: Preparation of Ethyl 2-(2-((tert-butylsulfinyl)amino)-4-phenylbutyl)-6-methoxynicotinate N-(1-(3-bromo-6-methoxypyridin-2-yl)-4-phenylbutan-2-yl)-2-methylpropane-2-sulfinamide (2 g) was weighed into a dry reaction flask, dissolved in ethanol (10 mL), and 1,1'-ferrocenediyl-bis(diphenylphosphino)palladium dichloride (0.67 g) and triethylamine (1.2 mL) were added, and the mixture was purged with nitrogen 3 times and heated to 110° C. The reaction was carried out overnight. LC-MS monitoring showed that the reaction was complete. The reaction system was concentrated to dryness and the residue was purified by column chromatography to obtain the title compound (1 g).

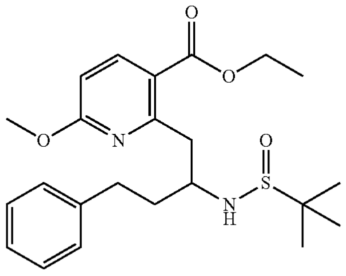 [SMILES: CCOC(=O)c1ccc(OC)nc1CC(CCc1ccccc1)NS(=O)C(C)(C)C]

MS (ESI) m/z $(M+H)^+$=433.2.

Step 4: Preparation of 6-(tert-butylsulfinyl)-2-methoxy-7-phenylethyl-7,8-dihydro-1,6-naphthyridin-5(6H)-one Ethyl 2-(2-((tert-butylsulfinyl)amino)-4-phenylbutyl)-6-methoxynicotinate (1 g) was weighed into a dry reaction flask, dissolved in acetonitrile (10 mL), cesium carbonate (124.5 mg) was added, and the reaction was heated to 80° C. The reaction was carried out for 6 hours. LC-MS monitoring showed that the reaction was complete. The system was filtered through Celite and the filtrate was concentrated to dryness. The residue was purified by column chromatography to obtain the title compound (0.6 g).

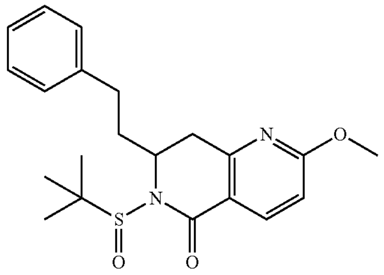 [SMILES: COc1ccc2c(n1)CC(CCc1ccccc1)N(S(=O)C(C)(C)C)C2=O]

MS (ESI) m/z $(M+H)^+$=387.1.

Step 5: Preparation of 2-hydroxy-7-phenylethyl-7,8-dihydro-1,6-naphthyridin-5(6H)-one 6-(Tert-butylsulfinyl)-2-methoxy-7-phenylethyl-7,8-dihydro-1,6-naphthyridin-5(6H)-one (600 mg) was weighed and dissolved in 33% hydrogen bromide in acetic acid (10 mL), heated to 80° C. and stirred for 2 hours. LC-MS monitoring showed that the reaction was complete. The solvent was evaporated under reduced pressure to give the crude title compound (1.2 g).

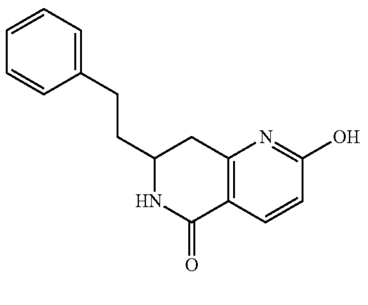 [SMILES: O=C1NC(CCc2ccccc2)Cc2nc(O)ccc21]

MS (ESI) m/z $(M+H)^+$=269.1.

Step 6: Preparation of 2-chloro-7-phenylethyl-7,8-dihydro-1,6-naphthyridin-5(6H)-one 2-Hydroxy-7-phenylethyl-7,8-dihydro-1,6-naphthyridin-5(6H)-one (1.2 g) was weighed and dissolved in phosphorus oxychloride (10 mL), heated to 95° C. and stirred for 2 hours. LCMS monitoring showed that the reaction was complete, and the solvent was removed under reduced pressure. Diluted with ethyl acetate and water was added, and the pH was adjusted to 7-8 with sodium carbonate, extracted with ethyl acetate for 3 times. The organic phase was concentrated and the residue was purified by silica gel column chromatography to obtain the title compound (200 mg).

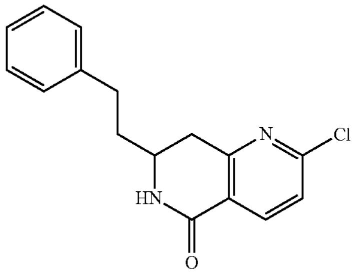 [SMILES: O=C1NC(CCc2ccccc2)Cc2nc(Cl)ccc21]

MS (ESI) m/z $(M+H)^+$=287.1.

Step 7: Preparation of 2-chloro-5-oxo-7-phenylethyl-7,8-dihydro-1,6-naphthyridin-6(5H)-carboxylate tert-butyl 2-Chloro-7-phenylethyl-7,8-dihydro-1,6-naphthyridin-5(6H)-one (185 mg) was weighed and dissolved in dichloromethane (10 mL), di-tert-butyl dicarbonate (423 mg), 4-dimethylaminopyridine (31.5 mg) and triethylamine (391 mg) were added, the mixture was warmed up to 40° C. and stirred overnight. LC-MS monitoring showed that the reaction was complete, and the solvent was removed under reduced pressure. Purification and separation on silica gel column gave the title compound (230 mg).

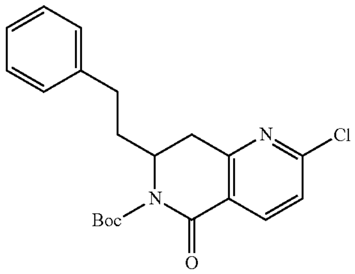 [SMILES: CC(C)(C)OC(=O)N1C(=O)c2ccc(Cl)nc2CC1CCc1ccccc1]

MS (ESI) m/z $(M+H)^+$=387.1.

Step 8 Preparation of Tert-butyl 2-chloro-7-phenylethyl-7,8-dihydro-1,6-naphthyridin-6(5H)-carboxylate Tert-butyl 2-chloro-5-oxo-7-phenylethyl-7,8-dihydro-1,6-naphthyridin-6(5H)-carboxylate (230 mg) was weighed and dissolved in tetrahydrofuran (6 mL), and 2.5 M borane dimethylsulfide complex (6 mL) was added. Heated to 50° C. for 4 hours, LC-MS monitoring showed that the reaction was complete, and the solvent was removed under reduced pressure. Purification and separation on silica gel column gave the title compound (120 mg).

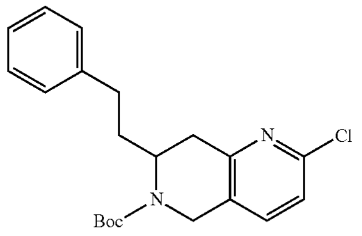 [SMILES: CC(C)(C)OC(=O)N1Cc2ccc(Cl)nc2CC1CCc1ccccc1]

MS (EST) m/z $(M+H)^+$=373.1

Step 9: Preparation of Tert-butyl 2-(di-tert-butoxyphosphoryl)-7-phenylethyl-7,8-dihydro-1,6-naphthyridin-6(5H)-carboxylate Tert-butyl 2-chloro-7-phenylethyl-7,8-dihydro-1,6-naphthyridin-6(5H)-carboxylate (60 mg) was weighed into a dry reaction flask, dissolved in toluene (10 mL), tris(dibenzylideneacetone)dipalladium (30 mg), 1,1'-ferrocenediyl-bis(diphenylphosphine) (35.7 mg), triethylamine (32 mg), di-tert-butyl phosphonate (63 mg) were added, and the system was purged with nitrogen 3 times and heated to 120° C. The reaction was carried out overnight. LC-MS monitoring showed that the reaction was complete, the system was concentrated to dryness and the residue was purified by column chromatography to obtain the title compound (20 mg).

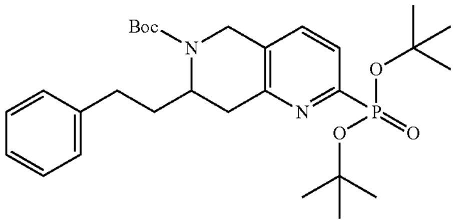 [SMILES: CC(C)(C)OC(=O)N1Cc2ccc(P(=O)(OC(C)(C)C)OC(C)(C)C)nc2CC1CCc1ccccc1]

MS (ESI) m/z $(M+H)^+$=531.2.

Step 10: Preparation of (7-phenylethyl-5,6,7,8-tetrahydro-1,6-naphthyridin-2-yl)phosphonic Acid Hydrochloride Tert-butyl 2-(di-tert-butoxyphosphoryl)-7-phenylethyl-7,8-dihydro-1,6-naphthyridin-6(5H)-carboxylate (20 mg) was weighed, dissolved in dichloromethane (3 mL), 4M HCl in 1,4-dioxane (3 mL) was added dropwise, stirred at room temperature for 1 hour, LC-MS monitoring showed that the reaction was complete. The solvent was evaporated under reduced pressure, and the residue was purified by pre-HPLC to obtain the title compound (5 mg).

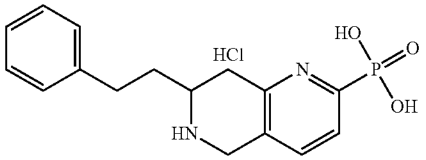 [SMILES: O=P(O)(O)c1ccc2c(n1)CC(CCc1ccccc1)NC2 ; Cl]

MS (ESI) m/z $(M+H)^+$=319.1.

$^1$H NMR (400 MHz, Deuterium Oxide) δ 7.88-7.63 (m, 3H), 7.37-7.17 (m, 4H), 4.51-4.29 (m, 2H), 3.61 (q, J=7.4, 5.0 Hz, 1H), 3.39 (dd, J=18.1, 4.8 Hz, 1H), 3.07 (dd, J=18.1, 10.9 Hz, 1H), 2.88-2.67 (m, 2H), 2.20-2.08 (m, 1H), 2.02 (dt, J=14.1, 7.9 Hz, 1H).

Example 14: Preparation of (7,7-diethyl-5,6,7,8-tetrahydro-naphthyridin-2-yl) Phosphonic Acid Hydrochloride

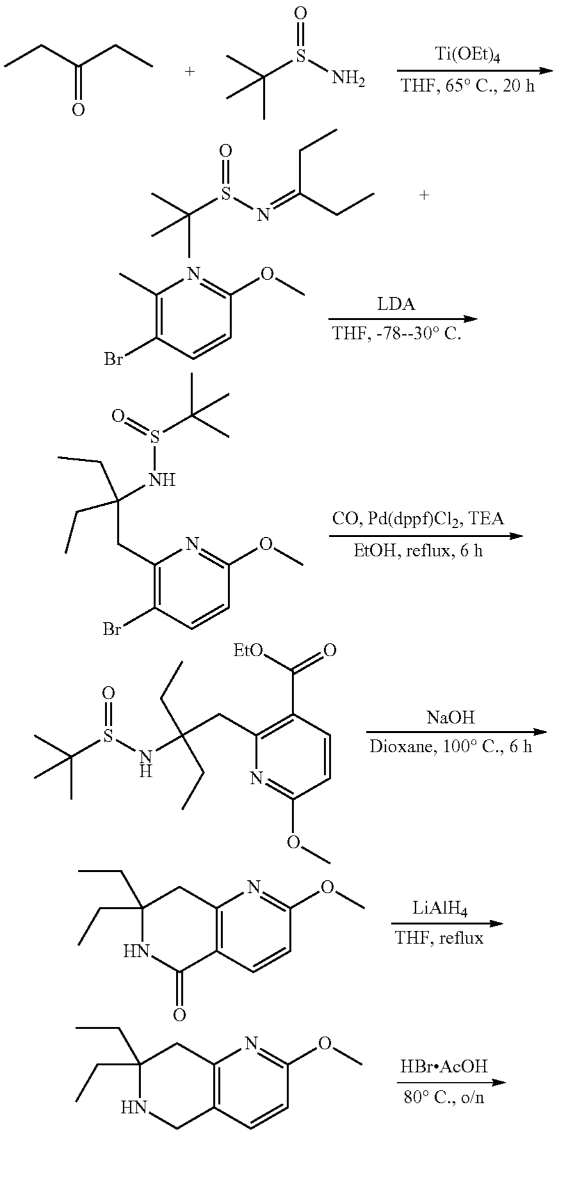

-continued

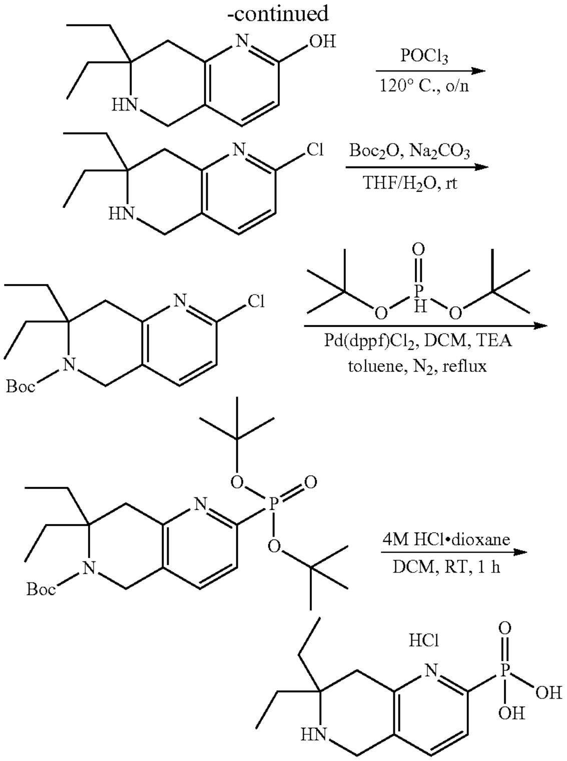

Step 1: Preparation of 2-methyl-N-(pentane-3-ylidene)propane-2-sulfinamide

Pentane-3-one (10.73 g) was weighed and dissolved in tetrahydrofuran (300 mL), tetraethyl titanate (46 g) and 2-methylpropane-2-sulfinamide (12 g) were added. After the completion of addition, the system was purged with nitrogen 3 times, and the mixture was heated at 65° C. for 20 hours. LC-MS monitoring showed that the reaction was complete. Water (30 mL) was added to the system to precipitate a large amount of solid. Filtered with suction, the organic phase was dried and concentrated to dryness, and the residue was purified by column chromatography to obtain the title compound (10.8 g).

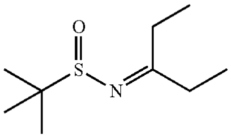

MS (ESI) m/z $(M+H)^+$=190.1.

Step 2: Preparation of N-(3-((3-bromo-6-methoxy-pyridin-2-yl)methyl)pent-3-yl)-2-methylpropane-2-sulfinamide Tetrahydrofuran (50 mL) was added into a dry reaction flask, purged with nitrogen 3 times, 2M lithium diisopropylamide (25 mL) was added and the temperature was lowered to −78° C. A solution of 3-bromo-6-methoxy-2-methylpyridine (9.4 g) in tetrahydrofuran (50 mL) was added and stirred at −78° C. for 1 hr. A solution of 2-methyl-N-(pentane-3-ylidene)propane-2-sulfinamide (8 g) in tetrahydrofuran (50 mL) was added and the mixture was stirred at −78° C. for 2 hours, with the temperature slowly raised from −78° C. to −30° C. LC-MS monitoring showed that the reaction was complete, and the system was quenched with saturated ammonium chloride solution, extracted 3 times with ethyl acetate, the organic phase was dried, concentrated to dryness, and the residue was purified by column chromatography to obtain the title compound (11.3 g).

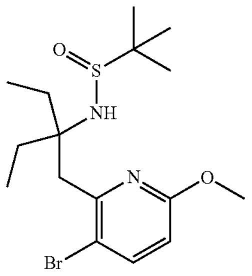 [SMILES: CCC(CC)(Cc1nc(OC)ccc1Br)NS(=O)C(C)(C)C]

MS (ESI) m/z $(M+H)^+$=391.1.

Step 3: Preparation of Ethyl 2-(2-((tert-butylsulfinyl)amino)-2-ethylbutyl)-6-methoxynicotinate N-(3-((3-bromo-6-methoxypyridin-2-yl)methyl)pent-3-yl)-2-methylpropane-2-sulfinamide (11.3 g) was weighed into a dry reaction flask, dissolved in ethanol (10 mL), and 1,1'-ferrocenediyl-bis(diphenylphosphino)palladium dichloride dichloromethane complex (4.73 g) and N,N-diisopropylethylamine (9.6 mL) were added, and the system was purged with nitrogen 3 times and heated to 100° C. The reaction was carried out overnight. LC-MS monitoring showed that the reaction was complete. The reaction system was concentrated to dryness and the residue was purified by column chromatography to obtain the title compound (9.3 g).

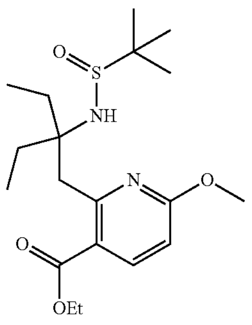 [SMILES: CCOC(=O)c1ccc(OC)nc1CC(CC)(CC)NS(=O)C(C)(C)C]

MS (ESI) m/z $(M+H)^+$=385.2.

Step 4: Preparation of 7,7-diethyl-2-methoxy-7,8-dihydro-1,6-naphthyridin-5(6H)-one Ethyl 2-(2-((tert-butylsulfinyl)amino)-2-ethylbutyl)-6-methoxynicotinate (9.3 g) was weighed into a dry reaction flask, dissolved in acetonitrile (10 mL), sodium hydroxide (4.8 g) was added, and the reaction was heated to 100° C. and reacted for 6 hours. LC-MS monitoring showed that the reaction was complete. The system was filtered through Celite and the filtrate was concentrated to dryness. The residue was purified by column chromatography to obtain the title compound (4.6 g).

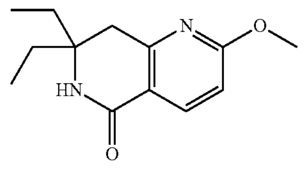 [SMILES: CCC1(CC)Cc2nc(OC)ccc2C(=O)N1]

MS (ESI) m/z $(M+H)^+$=235.1.

Step 5: Preparation of 7,7-diethyl-2-methoxy-5,6,7,8-tetrahydro-1,6-naphthyridine 7,7-Diethyl-2-methoxy-7,8-dihydro-1,6-naphthyridin-5(6H)-one (3 g) was weighed and dissolved in tetrahydrofuran (100 mL), lithium aluminium hydride (1.9 g) was added in portions while cooling on ice. The mixture was heated to reflux and stirred overnight. LC-MS monitoring showed that the reaction was complete, and the solvent was evaporated under reduced pressure. Purification and separation on silica gel column gave the title compound (2.8 g).

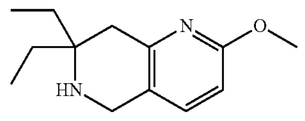 [SMILES: CCC1(CC)Cc2nc(OC)ccc2CN1]

MS (EST) m/z $(M+H)^+$=221.1.

Step 6: Preparation of 7,7-diethyl-5,6,7,8-tetrahydro-1,6-naphthyridin-2-ol 7,7-Diethyl-2-methoxy-5,6,7,8-tetrahydro-1,6-naphthyridine (2.8 g) was weighed and dissolved in 33% hydrogen bromide in acetic acid (20 mL), heated to 80° C. and stirred overnight. LC-MS monitoring showed that the reaction was complete. The solvent was evaporated under reduced pressure. The crude was slurried with acetonitrile to obtain the title compound (4.3 g).

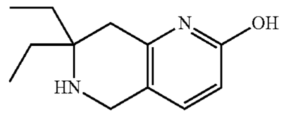

MS (ESI) m/z $(M+H)^+$=207.1.

Step 7: Preparation of 2-chloro-7,7-diethyl-5,6,7,8-tetrahydro-1,6-naphthyridine 7,7-Diethyl-5,6.7,8-tetrahydro-1,6-naphthyridin-2-ol (2.8 g) was weighed and dissolved in phosphorus oxychloride (40 mL). The mixture was heated to 120° C. and stirred overnight. LC-MS monitoring showed that the reaction was complete. The solvent was removed under reduced pressure. Diluted with dichloromethane, water was added and the pH was adjusted to 9-10 with sodium carbonate. The obtained crude title compound was used for the next step without further purification.

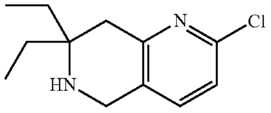

MS (ESI) m/z $(M+H)^+=225.1$.

Step 8: Preparation of tert-butyl 2-chloro-7,7-diethyl-7,8-dihydro-1,6-naphthyridin-6(5H)-carboxylate To the reaction work-up system of the previous step was added di-tert-butyl dicarbonate (4.67 mL), and the reaction mixture was stirred overnight at room temperature. The reaction was complete as monitored by LC-MS, and the reaction mixture was extracted with dichloromethane for 3 times. The organic phase was dried and concentrated. Purification and separation on silica gel column gave the title compound (1.5 g).

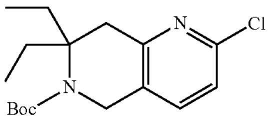 [SMILES: CCC1(CC)Cc2nc(Cl)ccc2CN1C(=O)OC(C)(C)C]

MS (ESI) m/z $(M+H)^+=325.1$

Step 9: Preparation of Tert-butyl 2-(di-tert-butoxyphosphoryl)-7,7-diethyl-7,8-dihydro-1,6-naphthyridin-6(5H)-carboxylate Tert-butyl 2-chloro-7,7-diethyl-7,8-dihydro-1,6-naphthyridin-6(5H)-carboxylate (200 mg) was weighed into a dry reaction flask, dissolved in toluene (10 mL), and 1,1'-ferrocenediyl-bis(diphenylphosphino)palladium dichloride dichloromethane complex (100 mg), triethylamine (0.17mL) and di-tert-butyl phosphonate (360 mg) were added, and the system was purged with nitrogen 3 times and heated to 120° C. The reaction was carried out overnight. The reaction was complete as monitored by LC-MS, and the reaction mixture was concentrated to dryness. The residue was purified by column chromatography to obtain the title compound (80 mg).

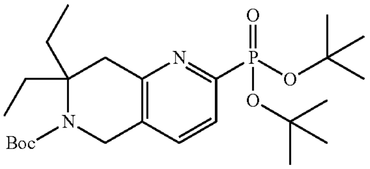 [SMILES: CCC1(CC)Cc2nc(P(=O)(OC(C)(C)C)OC(C)(C)C)ccc2CN1C(=O)OC(C)(C)C]

MS (ESI) m/z $(M+H)^+=483.2$.

Step 10: Preparation of (7,7-diethyl-5,6,7,8-tetrahydro-naphthyridin-2-yl) Phosphonic Acid Hydrochloride Tert-butyl 2-(di-tert-butoxyphosphoryl)-7,7-diethyl-7,8-dihydro-1,6-naphthyridin-6(5H)-carboxylate (80 mg) was weighed and dissolved in dichloromethane (4 mL), 4M HCl in 1,4-dioxane (4 mL) was added dropwise, stirred at room temperature for 1 hour, LC-MS monitoring showed that the reaction was complete. The solvent was evaporated under reduced pressure, and the residue was purified by pre-HPLC to obtain the title compound (13 mg).

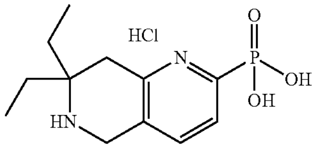 [SMILES: CCC1(CC)Cc2nc(P(=O)(O)O)ccc2CN1 ; Cl]

MS (EST) m/z $(M+H)^+=271.1$.

$^1H$ NMR (400 MHZ, Deuterium Oxide) δ 7.88-7.57 (m, 2H), 4.39 (s, 2H), 3.11 (s, 2H), 1.84-1.42 (m, 4H), 0.90 (t, J=7.5 Hz, 6H).

Preparation 1: Tert-butyl 2-Chloro-8-hydroxy-7,8-dihydro-1,6-naphthyridin-6(5H)-carboxylate

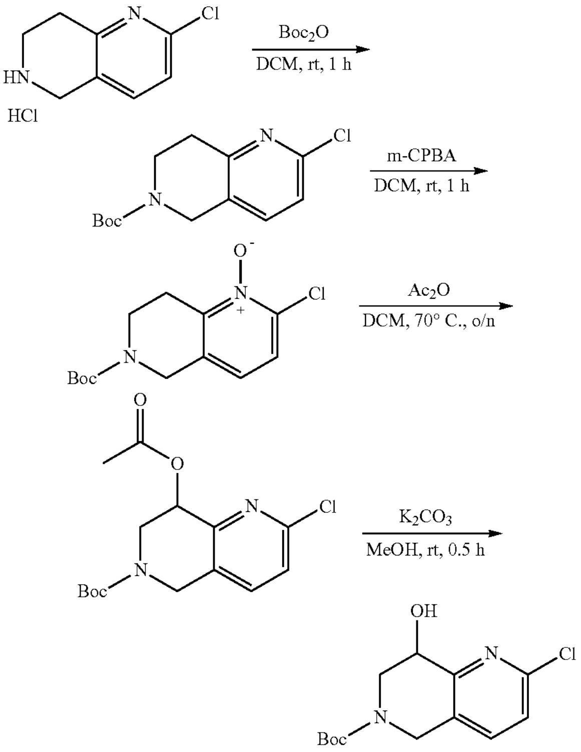

Step 1: Preparation of Tert-butyl 2-chloro-7,8-dihydro-1,6-naphthyridin-6(5H)-carboxylate

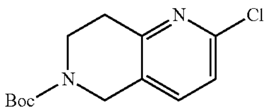 [SMILES: CC(C)(C)OC(=O)N1CCc2nc(Cl)ccc2C1]

2-Chloro-5,6,7,8-tetrahydro-1,6-naphthyridine hydrochloride (5 g) was dissolved in dichloromethane (50 ml), triethylamine (10 ml) was added, and di-tert-butyl dicarbonate (6.7 ml) was slowly added dropwise. After the completion of addition, the reaction was carried out at room temperature for 3 hours, and LC-MS showed that the reaction was complete. The mixture was concentrated to give a crude oil which was separated by chromatographic column to obtain the title compound (6 g).

MS (ESI) m/z $(M+H)^+$=269.1.

Step 2: preparation of 6-(tert-butoxycarbonyl)-2-chloro-5,6,7,8-tetrahydro-1,6-naphthyridine 1-oxide

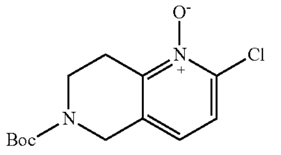

Tert-butyl 2-chloro-7,8-dihydro-1,6-naphthyridin-6(5H)-carboxylate (9 g, 33.58 mmol) was weighed and dissolved in dichloromethane (100 ml), and m-chloroperoxybenzoic acid (11.7 g) was added in portions under cooling with an ice-bath. The reaction was carried out overnight at room temperature and LC-MS showed completion of the reaction. Dichloromethane and water were added, the layers were separated and the aqueous layer was extracted, and the organic phase was concentrated to dryness. The resulting crude product was purified by column chromatography to obtain the title compound (7.0 g).

MS (ESI) m/z $(M+H)^+$=285.1.

Step 3: Preparation of Tert-butyl 8-acetoxy-2-chloro-7,8-dihydro-1,6-naphthyridin-6(5H)-carboxylate

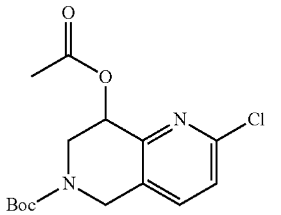 [SMILES: CC(=O)OC1CN(C(=O)OC(C)(C)C)Cc2ccc(Cl)nc21]

6-(Tert-butyloxycarbonyl)-2-chloro-5,6,7,8-tetrahydro-1,6-naphthyridine 1-oxide (7 g) was weighed and dissolved in acetic anhydride (80 mL), purged with nitrogen 3 times, and heated to 70° C. to react overnight. LC-MS showed that the reaction was complete. Concentrated under reduced pressure to remove a large amount of acetic anhydride, and ethyl acetate and water were added. Extracted with ethyl acetate for 3 times, and washed with saturated sodium bicarbonate solution for 2 times. The organic phase was dried and concentrated, and the residue was separated and purified by chromatographic column to obtain the title compound (5 g).

MS (ESI) m/z $(M+H)^+$=327.1.

Step 4: Preparation of Tert-butyl 2-chloro-8-hydroxy-7,8-dihydro-1,6-naphthyridin-6(5H)-carboxylate

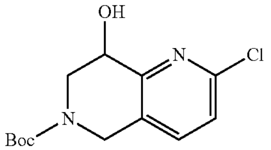 [SMILES: CC(C)(C)OC(=O)N1Cc2ccc(Cl)nc2C(O)C1]

Tert-butyl 8-acetoxy-2-chloro-7,8-dihydro-1,6-naphthyridin-6(SH)-carboxylate (3 g) was weighed and dissolved in methanol (30 ml), and potassium carbonate (635 mg) was added. After the completion of addition, the reaction was carried out at room temperature for 0.5 hour, LC-MS showed that the reaction was complete. Ethyl acetate and water were added. extracted with ethyl acetate for 3 times. The organic phase was dried and concentrated to give an oily crude product, which was separated and purified by column chromatography to obtain the title compound (1.9 g).

MS (ESI) m/z $(M+H)^+$=285.1.

Preparation 2: 6-(Tert-butyl) 7-methyl 2-chloro-7,8-dihydro-1,6-naphthyridin-6,7(5H)-dicarboxylate

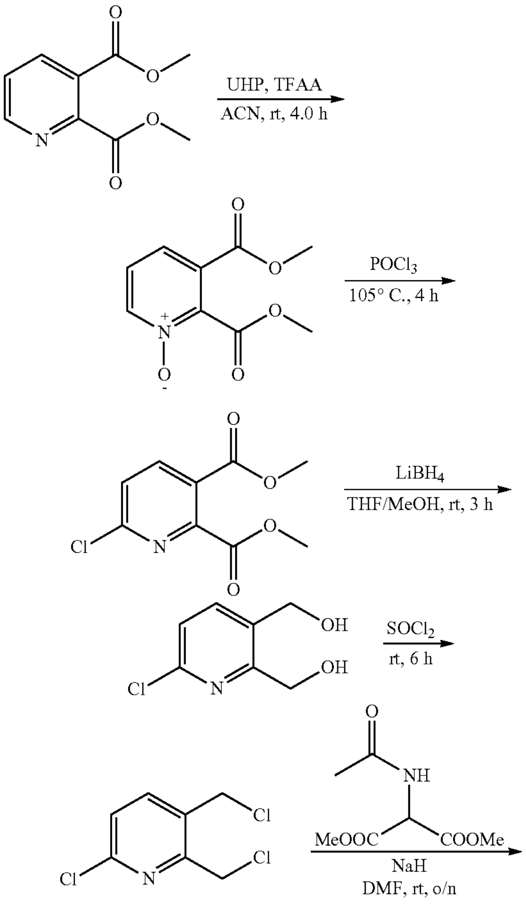

-continued

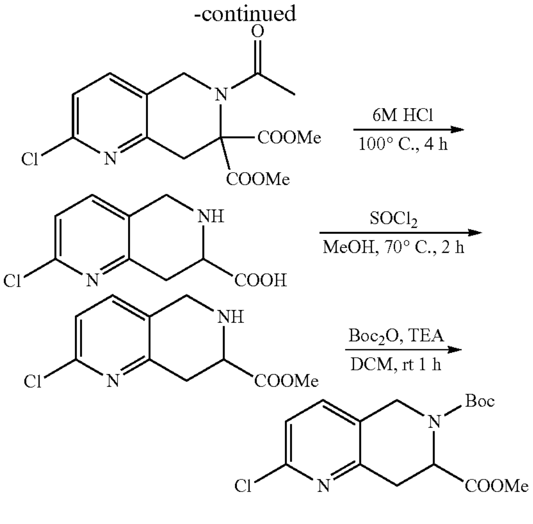

Step 1: Preparation of 2,3-bis(methoxycarbonyl)pyridine 1-oxide

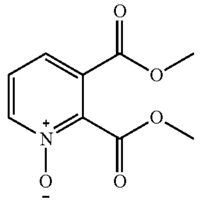

Dimethyl pyridin-2,3-dicarboxylate (4.90 g) was weighed and dissolved in acetonitrile (60 mL), carbamide peroxide (4.71 g) was added under ice bath cooling, and trifluoroacetic anhydride (10.5 g) was slowly added dropwise. After the completion of addition, the system became a clear solution, and the temperature was raised to room temperature and reacted for 4 hours. TLC showed substantial completion of the reaction. The reaction was quenched by adding sodium metabisulfite aqueous solution. Dichloromethane and water were added, the layers were separated and the aqueous layer was extracted with mixed solvent (DCM/MeOH). The organic phase was dried over anhydrous sodium sulfate, filtered with suction, and the filtrate was concentrated to dryness to obtain the title compound (5.15 g).

MS (EST) m/z $(M+H)^+$=212.1.

Step 2: preparation of Dimethyl 6-chloropyridin-2,3-dicarboxylate

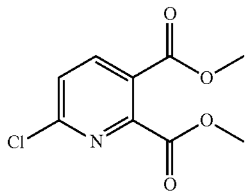

2,3-Bis(methoxycarbonyl)pyridine 1-oxide (5.15 g) was weighed, phosphorus oxychloride (30 mL) was added under ice bath cooling, the mixture was heated to 105° C. and reacted for 4 hours, and TLC showed completion of the reaction. The mixture was concentrated under reduced pressure, diluted with ethyl acetate, added dropwise to crushed ice, sodium carbonate aqueous solution was added to adjust pH=10, extracted with ethyl acetate, and the organic phase was washed with sodium chloride aqueous solution. The organic phase was concentrated to dryness and the crude product was purified by column chromatography to obtain the title compound (3.52 g).

MS (ESI) m/z $(M+H)^+$=230.1.

Step 3: Preparation of (6-chloropyridin-2,3-diyl)dimethanol

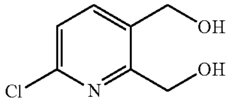 [SMILES: OCc1ccc(Cl)nc1CO]

Dimethyl 6-chloropyridin-2,3-dicarboxylate (3.50 g) was weighed and dissolved in tetrahydrofuran (72 mL) and methanol (1.5 mL), and lithium borohydride (0.84 g) was added in portions under ice bath cooling. The mixture was allowed to warm to room temperature and reacted for 3 hours. TLC showed most of the starting material was consumed. The reaction system was poured into a sodium bicarbonate aqueous solution, ethyl acetate was added, the layers were separated and extracted, the organic phase was dried over anhydrous sodium sulfate, filtered with suction, and the filtrate was concentrated to dryness to obtain the title compound (2.63 g).

MS (EST) m/z $(M+H)^+$=174.1.

Step 4: Preparation of 6-chloro-2,3-bis(chloromethyl)pyridine

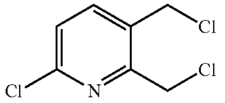 [SMILES: ClCc1ccc(Cl)nc1CCl]

(6-Chloropyridin-2,3-diyl)dimethanol (2.63 g) was weighed, thionyl chloride (40 mL) was added under ice-bath cooling, and then reacted at room temperature for 3 hours. Due to the presence of some monochlorinated intermediate, the temperature was raised to 35° C. and reacted for 3 hours, and TLC showed that the reaction was complete. The mixture was concentrated under reduced pressure, diluted with ethyl acetate, added dropwise to crushed ice, sodium carbonate aqueous solution was added to adjust pH=10, extracted with ethyl acetate, and the organic phase was washed with sodium chloride aqueous solution. The organic phase was concentrated to dryness and the crude product was purified by column chromatography to obtain the title compound (2.1 g).

MS (ESI) m/z $(M+H)^+$=210.1.

Step 5: Preparation of Dimethyl 6-acetyl-2-chloro-5,8-dihydro-1,6-naphthyridin-7,7(6H)-dicarboxylate

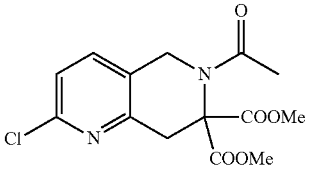 [SMILES: COC(=O)C1(C(=O)OC)Cc2nc(Cl)ccc2CN1C(C)=O]

6-Chloro-2,3-bis(chloromethyl)pyridine (2.10 g) was weighed and dissolved in N,N-dimethylformamide (15 mL), and dimethyl acetylaminomalonate (2.17 g) and sodium hydride (0.40 g) were added successively under ice bath cooling. The reaction was carried out at room temperature for 1 hour, and sodium hydride (0.40 g) was added under ice bath cooling, and then reacted at room temperature overnight. TLC showed the reaction was complete. Ethyl acetate and water were added, the layers were separated and extracted. The organic phase was concentrated to dryness and the crude product was purified by column chromatography to obtain the title compound (1.74 g).

MS (ESI) m/z $(M+H)^+$=327.1.

Step 6: Preparation of 2-chloro-5,6,7,8-tetrahydro-1,6-naphthyridin-7-carboxylic Acid Hydrochloride

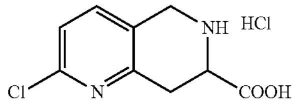 [SMILES: O=C(O)C1Cc2nc(Cl)ccc2CN1 ; Cl]

Dimethyl 6-acetyl-2-chloro-5,8-dihydro-1,6-naphthyridin-7,7(6H)-dicarboxylate (1.74 g) was weighed, added with 6M hydrochloric acid (15 mL), and reacted under sealed condition at 100° C. for 4 hours, and TLC showed completion of the reaction. The mixture was concentrated to dryness under reduced pressure to obtain the title compound (1.16 g).

MS (ESI) m/z $(M+H)^+$=213.1.

Step 7: Preparation of Methyl 2-chloro-5,6,7,8-tetrahydro-1,6-naphthyridin-7-carboxylate hydrochloride

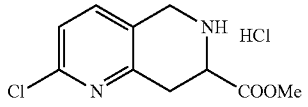 [SMILES: COC(=O)C1Cc2nc(Cl)ccc2CN1 ; Cl]

2-Chloro-5,6,7,8-tetrahydro-1,6-naphthyridin-7-carboxylic acid hydrochloride (1.16 g) was weighed and dissolved in methanol (20 mL), and thionyl chloride (1.67 g) was slowly added dropwise under ice bath cooling. The reaction was refluxed for 2 hours at 70° C. and TLC showed completion of the reaction. The mixture was concentrated to dryness under reduced pressure to obtain the title compound (1.23 g).

MS (ESI) m/z $(M+H)^+$=227.1.

Step 8: Preparation of 6-(tert-butyl) 7-methyl 2-chloro-7,8-dihydro-1,6-naphthyridin-6,7(5H)-dicarboxylate

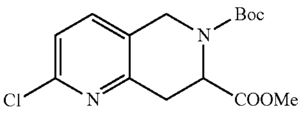 [SMILES: COC(=O)C1Cc2nc(Cl)ccc2CN1C(=O)OC(C)(C)C]

Methyl 2-chloro-5,6,7,8-tetrahydro-1,6-naphthyridin-7-carboxylate hydrochloride (1.23 g) was weighed and dissolved in dichloromethane (25 mL), and triethylamine (1.89 g) and di-tert-butyl dicarbonate (1.53 g) were added successively. The reaction was allowed to react at room temperature for 2 hours and TLC showed completion of the reaction. Dichloromethane and water were added, the layers were separated and extracted, and the organic phase was concentrated to dryness. The resulting crude product was purified by column chromatography to obtain the title compound (1.19 g).

MS (ESI) m/z $(M+H)^+$=327.1.

$^1$H NMR (400 MHZ, Chloroform-d) δ 7.42 (dd, J=12.5, 8.0 Hz, 1H), 7.21 (d, J=8.1 Hz, 1H), 5.34 (d, J=6.7 Hz, 0.5H), 5.07 (dd, J=7.2, 2.9 Hz, 0.5H), 4.79 (dd, J=22.4, 17.0 Hz, 1H), 4.52 (dd, J=31.0, 17.1 Hz, 1H), 3.68 (d, J=7.7 Hz, 3H), 3.55-3.38 (m, 1H), 3.38-3.20 (m, 1H), 1.52 (d, J=17.9 Hz, 9H)

Preparation 3: Tert-butyl 2-chloro-7-formyl-7,8-dihydro-1,6-naphthyridin-6(5H)-carboxylate

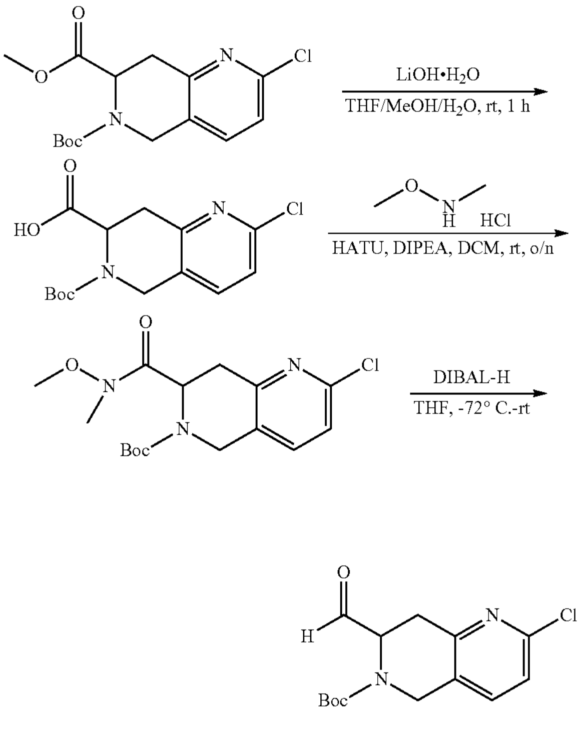

Step 1: Preparation of 6-(tert-butoxycarbonyl)-2-chloro-5,6,7,8-tetrahydro-1,6-naphthyridin-7-carboxylic acid

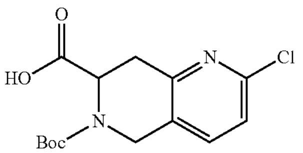 [SMILES: CC(C)(C)OC(=O)N1Cc2ccc(Cl)nc2CC1C(=O)O]

6-(Tert-butyl) 7-methyl 2-chloro-7,8-dihydro-1,6-naphthyridin-6,7(5H)-dicarboxylate (0.4 g) was dissolved in a mixture of tetrahydrofuran (3 mL)/methanol (3 mL)/water (3 mL) at room temperature, lithium hydroxide hydrate (0.1 g) was added, the reaction was stirred for 1 hour, and LCMS showed that the reaction was complete. The pH was adjusted to 4-5 with dilute hydrochloric acid (1M) under ice bath cooling. Partition between ethyl acetate and water, and the aqueous layer was extracted with ethyl acetate. The organic phases were combined, dried over anhydrous sodium sulfate, filtered, and the solvent was removed under reduced pressure to obtain the title compound (0.369 g).

MS (ESI) m/z $(M+H)^+$=313.1.

Step 2: Preparation of Tert-butyl 2-chloro-7-(methoxy(methyl)carbamoyl)-7,8-dihydro-1,6-naphthyridin-6(5H)-carboxylate

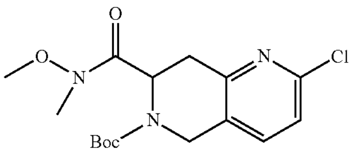 [SMILES: CON(C)C(=O)C1Cc2nc(Cl)ccc2CN1C(=O)OC(C)(C)C]

6-(Tert-Butoxycarbonyl)-2-chloro-5,6,7,8-tetrahydro-1,6-naphthyridin-7-carboxylic acid (0.374 g) was dissolved in dichloromethane (20 mL) at room temperature, and N,N-diisopropylethylamine (1.25 mL), 2-(7-azabenzotriazol-1-yl)-N,N,N',N'-tetramethyluronium hexafluorophosphate (0.494 g), and methoxymethylamine hydrochloride (0.235 g) were added successively and stirred overnight, and TLC showed completion of the reaction. Dichloromethane and water were added, the layers were separated and extracted with dichloromethane, washed with saturated sodium chloride solution, the organic phases were combined, dried over anhydrous sodium sulfate, filtered, and the solvent was evaporated under reduced pressure. The resulting crude product was purified by silica gel column chromatography to obtain the title compound (0.379 g).

MS (ESI) m/z $(M+H)^+$=356.1.

Step 3: Preparation of Tert-butyl 2-chloro-7-formyl-7,8-dihydro-1,6-naphthyridin-6(5H)-carboxylate

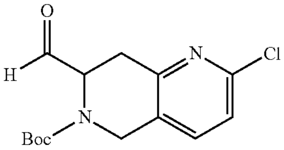 [SMILES: CC(C)(C)OC(=O)N1Cc2ccc(Cl)nc2CC1C=O]

Tert-butyl 2-chloro-7-(methoxy(methyl)carbamoyl)-7,8-dihydro-1,6-naphthyridin-6(5H)-carboxylate (0.378 g) was dissolved anhydrous tetrahydrofuran (20 mL), purged with nitrogen and the system was cooled to −72° C. Diisobutylaluminum hydride solution (1M, 3.21 mL) was added and the system was slowly warmed up to room temperature and stirred for 3 hours. LCMS showed the reaction was complete. The reaction system was placed in an ice bath and quenched by adding water dropwise for 10 minutes. Saturated potassium sodium tartrate solution (20 mL) was added and stirred for 20 minutes, extracted with ethyl acetate, the organic phases were combined, dried over anhydrous sodium sulfate, filtered, the solvent was evaporated under reduced pressure, and the resulting crude product was purified by silica gel column chromatography to obtain the title compound (0.206 g).

MS (ESD) m/$(M+H)^+$=297.0.

The following compounds were prepared using conventional commercially available starting materials and reagents, referring to the preparation methods of the foregoing examples in combination with conventional separation and purification methods in the field:

| Exp. | Structure | MS and $^1$H NMR data | Preparation method |
|---|---|---|---|
| 15 | 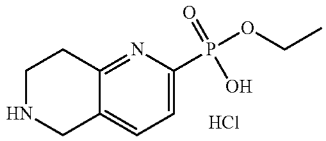 [SMILES: CCOP(=O)(O)c1ccc2c(n1)CCNC2 ; Cl] HCl | MS (ESI) m/z (M + H)$^+$ = 243.1. $^1$H NMR (400 MHz, Deuterium Oxide) δ 7.90 (dd, J = 8.0, 3.6 Hz, 1H), 7.78 (t, J = 7.3 Hz, 1H), 4.45 (s, 2H), 3.79 (p, J = 7.3 Hz, 2H), 3.59 (t, J = 6.4 Hz, 2H), 3.27 (t, J = 6.4 Hz, 2H), 1.09 (t, J = 7.0 Hz, 3H). | Referring to Example 1 |
| 16 | 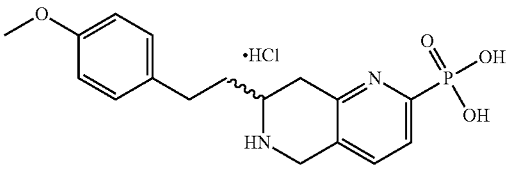 [SMILES: COc1ccc(CCC2Cc3nc(P(=O)(O)O)ccc3CN2)cc1 ; Cl] •HCl | MS (ESI) m/z (M + H)$^+$ = 349.0. $^1$H NMR (400 MHz, Deuterium Oxide) δ 7.64 (qd, J = 8.0, 5.0 Hz, 2H), 7.17-7.11 (m, 2H), 6.86-6.79 (m, 2H), 4.42-4.27 (m, 2H), 3.66 (s, 3H), 3.53 (dp, J = 13.1, 4.8 Hz, 1H), 3.31 (dd, J = 18.1, 4.8 Hz, 1H), 3.00 (dd, J = 18.1, 10.8 Hz, 1H), 2.76-2.58 (m, 2H), 2.12-1.89 (m, 2H). | Referring to Example 12 |

-continued

| Exp. | Structure | MS and $^1$H NMR data | Preparation method |
|---|---|---|---|
| 17 | 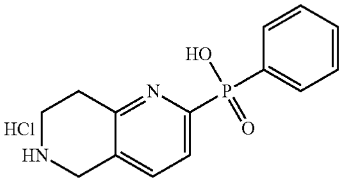 [SMILES: Cl ; O=P(O)(c1ccccc1)c1ccc2c(n1)CCNC2] | MS (ESI) m/z $(M + H)^+$ = 275.0. $^1$H NMR (400 MHz, Deuterium Oxide) δ 7.76 (qd, J = 8.0, 4.4 Hz, 2H), 7.68-7.56 (m, 2H), 7.51-7.40 (m, 1H), 7.37 (ddd, J = 8.3, 6.5, 3.2 Hz, 2H), 4.39 (s, 2H), 3.53 (t, J = 6.4 Hz, 2H), 3.16 (t, J = 6.4 Hz, 2H). | Referring to Example 1 |
| 18 | 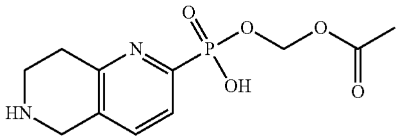 [SMILES: CC(=O)OCOP(=O)(O)c1ccc2c(n1)CCNC2] | MS (ESI) m/z $(M + H)^+$ = 287.0. $^1$H NMR (400 MHz, Deuterium Oxide) δ 7.69-7.63 (m, 2H), 5.44 (d, J = 13.5 Hz, 2H), 4.40 (s, 2H), 3.59 (t, J = 6.5 Hz, 2H), 3.18 (t, J = 6.5 Hz, 2H), 1.75 (s, 3H). | Referring to Example 1 |
| 19 | 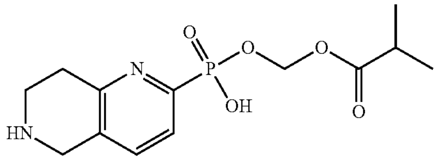 [SMILES: CC(C)C(=O)OCOP(=O)(O)c1ccc2c(n1)CCNC2] | MS (ESI) m/z $(M + H)^+$ = 315.0. $^1$H NMR (400 MHz, Deuterium Oxide) δ 7.73-7.63 (m, 2H), 5.50 (d, J = 13.7 Hz, 2H), 4.42 (s, 2H), 3.59 (t, J = 6.4 Hz, 2H), 3.19 (t, J = 6.4 Hz, 2H), 2.26 (p, J = 7.0 Hz, 1H), 0.83 (d, J = 7.1 Hz, 6H). | Referring to Example 1 |
| 20 | 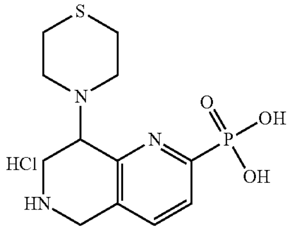 [SMILES: Cl ; O=P(O)(O)c1ccc2c(n1)C(N1CCSCC1)CNC2] | MS (ESI) m/z $(M + H)^+$ = 316.0. $^1$H NMR (400 MHz, Deuterium Oxide) δ 7.85-7.74 (m, 2H), 5.10 (dd, J = 11.1, 6.2 Hz, 1H), 4.57-4.43 (m, 2H), 4.20 (dd, J = 12.7, 6.2 Hz, 1H), 3.85 (dd, J = 12.7. 11.1 Hz, 1H), 3.52 (d, J = 56.6 Hz, 4H), 3.01 (s, 4H) | Referring to Example 7 |
| 21 | 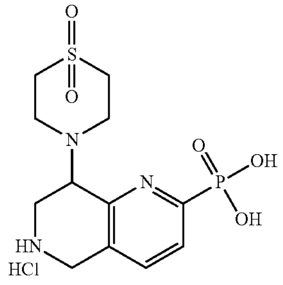 | MS (ESI) m/z $(M + H)^+$ = 348.0. $^1$H NMR (400 MHz, Deuterium Oxide) δ 8.22 (dd, J = 8.1, 3.0 Hz, 1H), 8.08-7.97 (m, 1H), 4.55 (s, 2H), 3.89 (dd, J = 12.9, 5.5 Hz, 1H), 3.63 (dd, J = 12.9, 9.6 Hz, 1H), 3.28 (m, 4H), 3.25-3.09 (m, 5H). | Referring to Example 7 |
| 22 | 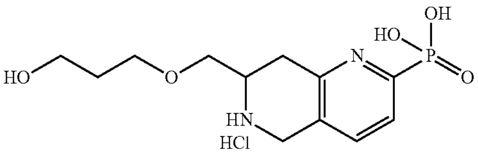 [SMILES: O=P(O)(O)c1ccc2c(n1)CC(COCCCO)NC2 ; Cl] | MS (ESI) m/z $(M + H)^+$ = 303.1. $^1$H NMR (400 MHz, Deuterium Oxide) δ 7.71 (dd, J = 8.0, 3.6 Hz, 1H), 7.65 (t, J = 7.1 Hz, 1H), 4.36 (s, 2H), 3.84-3.74 (m, 2H), 3.67-3.51 (m, 5H), 3.19 (d, J = 17.0 Hz, 1H), 3.13-3.03 (m, 1H), 1.74 (p, J = 6.3 Hz, 2H). | Referring to Example 11 |
| 23 | 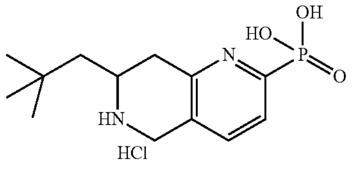 [SMILES: CC(C)(C)CC1Cc2nc(P(=O)(O)O)ccc2CN1 ; Cl] | MS (ESI) m/z $(M + H)^+$ = 285.0. $^1$H NMR (400 MHz, Deuterium Oxide) δ 7.74 (dd, J = 8.0, 3.8 Hz, 1H), 7.67 (dd, J = 7.9, 6.2 Hz, 1H), 4.43 (s, 2H), 3.75 (ddt, J = 9.6, 6.6, 3.4 Hz, 1H), 3.45 (dd, J = 18.2, 4.8 Hz, 1H), 3.06 (dd, J = 18.2, 10.3 Hz, 1H), 1.74-1.60 (m, 2H), 0.92 (s, 9H). | Referring to Example 12 |
| 24 | 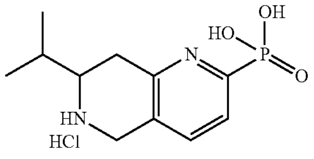 [SMILES: CC(C)C1Cc2nc(P(=O)(O)O)ccc2CN1 ; Cl] | MS (ESI) m/z $(M + H)^+$ = 257.0. $^1$H NMR (400 MHz, Deuterium Oxide) δ 8.24 (dd, J = 8.1, 2.8 Hz, 1H), 7.99 (t, J = 7.6 Hz, 1H), 4.64-4.52 (m, 2H), 3.59 (dt, J = 11.8, 5.0 Hz, 1H), 3.48 (dd, J = 18.6, 4.5 Hz, 1H), 3.26 (dd, J = 18.5, 11.9 Hz, 1H), 2.20-2.10 (m, 1H), 1.11-0.92 (m, 6H). | Referring to Example 12 |

-continued

| Exp. | Structure | MS and $^1$H NMR data | Preparation method |
|---|---|---|---|
| 25 | 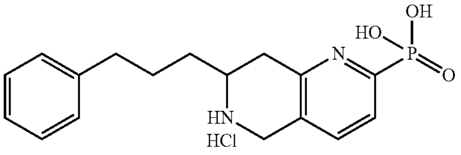 [SMILES: O=P(O)(O)c1ccc2c(n1)CC(CCCc1ccccc1)NC2 ; Cl] | MS (ESI) m/z $(M + H)^+$ = 333.0. $^1$H NMR (400 MHz, Deuterium Oxide) δ 7.78-7.66 (m, 2H), 7.40-7.07 (m, 5H), 4.40 (s, 2H), 3.70-3.61 (m, 1H), 3.32 (dd, J = 18.2, 4.8 Hz, 1H), 2.99 (dd, J = 18.2. 10.7 Hz, 1H), 2.63 (d, J = 7.3 Hz, 2H), 1.87-1.61 (m, 4H). | Referring to Example 12 |
| 26 | 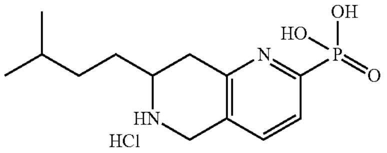 [SMILES: CC(C)CCC1Cc2nc(P(=O)(O)O)ccc2CN1 ; Cl] | MS (ESI) m/z $(M + H)^+$ = 285.1. $^1$H NMR (400 MHz, Deuterium Oxide) δ 7.76 (dd, J = 8.1, 3.9 Hz, 1H), 7.70 (dd, J = 7.9, 6.2 Hz, 1H), 4.44 (s, 2H), 3.72-3.61 (m, 1H), 3.35 (dd, J = 18.2, 4.8 Hz, 1H), 3.03 (dd, J = 18.2, 10.8 Hz, 1H), 1.88-1.69 (m, 2H), 1.54 (dt, J = 13.3, 6.7 Hz, 1H), 1.31 (q, J = 7.5 Hz, 2H), 0.83 (d, J = 6.6 Hz, 6H). | Referring to Example 12 |
| 27 | 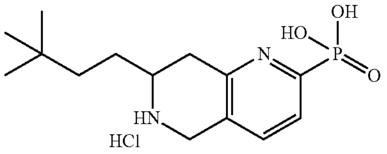 [SMILES: CC(C)(C)CCC1Cc2nc(P(=O)(O)O)ccc2CN1 ; Cl] | MS (ESI) m/z $(M + H)^+$ = 299.2. $^1$H NMR (400 MHz, Deuterium Oxide) δ 7.79 (dd, J = 8.1, 3.8 Hz, 1H), 7.72 (dd, J = 7.9, 6.3 Hz, 1H), 4.45 (s, 2H), 3.71-3.60 (m, 1H), 3.37 (dd, J = 18.3, 4.8 Hz, 1H), 3.05 (dd, J = 18.2, 10.8 Hz, 1H), 1.86-1.69 (m, 2H), 1.32 (ddd, J = 11.3, 7.5, 5.7 Hz, 2H), 0.84 (s, 9H). | Referring to Example 12 |
| 28 | 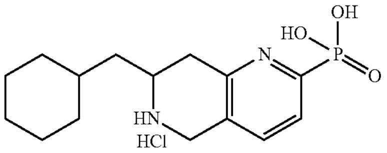 [SMILES: O=P(O)(O)c1ccc2c(n1)CC(CC1CCCCC1)NC2 ; Cl] | MS (ESI) m/z $(M + H)^+$ = 311.0. $^1$H NMR (400 MHz, Deuterium Oxide) δ 7.74 (dd, J = 8.1, 3.8 Hz, 1H), 7.68 (t, J = 7.1 Hz, 1H), 4.41 (s, 2H), 3.77 (s, 1H), 3.35 (dd, J = 18.3, 4.8 Hz, 1H), 2.97 (dd, J = 18.2, 10.6 Hz, 1H), 1.86-1.30 (m, 8H), 1.29-1.01 (m, 3H), 0.90 (p, J = 11.6, 11.1 Hz, 2H). | Referring to Example 12 |
| 29 | 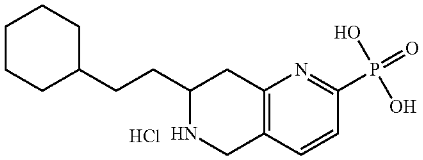 [SMILES: O=P(O)(O)c1ccc2c(n1)CC(CCC1CCCCC1)NC2 ; Cl] | MS (ESI) m/z $(M + H)^+$ = 325.0. $^1$H NMR (400 MHz, Deuterium Oxide) δ 8.23 (dd, J = 8.1, 2.8 Hz, 1H), 7.98 (t, J = 7.6 Hz, 1H), 4.64-4.48 (m, 2H), 3.68 (m, 1H), 3.55 (dd, J = 18.7, 4.7 Hz, 1H), 3.18 (dd, J = 18.7, 10.7 Hz, 1H), 1.92-1.69 (m, 2H), 1.67-1.48 (m, 5H), 1.30 (q, J = 8.0, 7.4 Hz, 2H), 1.22-1.00 (m, 4H), 0.83 (m, 2H). | Referring to Example 12 |
| 30 | 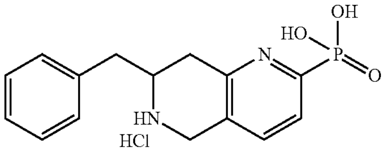 [SMILES: O=P(O)(O)c1ccc2c(n1)CC(Cc1ccccc1)NC2 ; Cl] | MS (ESI) m/z $(M + H)^+$ = 305.1. $^1$H NMR (400 MHz, Deuterium Oxide) δ 8.46 (d, J = 8.0 Hz, 1H), 8.24 (t, J = 7.5 Hz, 1H), 7.27-7.22 (m, 2H), 7.03 (d, J = 8.2 Hz, 1H), 6.64 (dd, J = 6.7, 2.8 Hz, 2H), 4.37 (s, 2H), 3.80 (p, J = 7.0 Hz, 1H), 3.40 (t, J = 7.2 Hz, 1H), 2.92-2.80 (m, 1H), 2.36 (dd, J = 12.8, 6.7 Hz, 1H), 1.17-1.09 (m, 1H). | Referring to Example 12 |
| 31 | 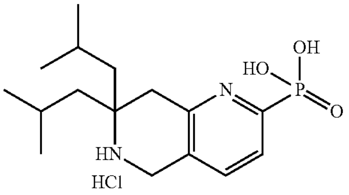 [SMILES: CC(C)CC1(CC(C)C)Cc2nc(P(=O)(O)O)ccc2CN1 ; Cl] | MS (ESI) m/z $(M + H)^+$ = 327.2. $^1$H NMR (400 MHz, Deuterium Oxide) δ 7.79-7.67 (m, 2H), 4.41 (m, 2H), 3.29-3.09 (m, 2H), 1.70 (m), 2H), 1.56 (m, 2H), 1.39 (m, 3H), 1.08 (m, 2H), 0.90 (m, 3H), 0.76 (m, 6H). | Referring to Example 145 |
| 32 | 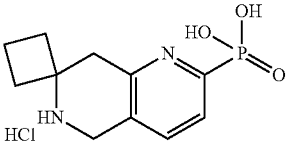 [SMILES: O=P(O)(O)c1ccc2c(n1)CC1(CCC1)NC2 ; Cl] | MS (ESI) m/z $(M + H)^+$ = 255.1. $^1$H NMR (400 MHz, Deuterium Oxide) δ 8.32 (d, J = 7.9 Hz, 1H), 8.04 (t, J = 7.7 Hz, 1H), 4.55 (s, 2H), 3.62 (s, 2H), 2.41 (q, J = 10.1, 9.3 Hz, 2H), 2.15-2.03 (m, 2H), 1.98 (m, 2H). | Referring to Example 14 |
| 33 | 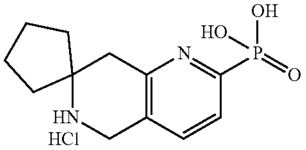 [SMILES: O=P(O)(O)c1ccc2c(n1)CC1(CCCC1)NC2 ; Cl] | MS (ESI) m/z $(M + H)^+$ = 269.1. $^1$H NMR (400 MHz, Deuterium Oxide) δ 7.80 (dd, J = 8.0, 3.8 Hz, 1H), 7.72 (t, J = 7.1 Hz, 1H), 4.46 (s, 2H), 3.20 (s, 2H), 1.91-1.76 (m, 8H). | Referring to Example 14 |

-continued

| Exp. | Structure | MS and $^1$H NMR data | Preparation method |
|---|---|---|---|
| 34 | 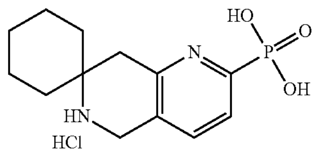 [SMILES: O=P(O)(O)c1ccc2c(n1)CC1(CCCCC1)NC2 ; Cl] | MS (ESI) m/z $(M + H)^+$ = 283.1. $^1$H NMR (400 MHz, Deuterium Oxide) δ 7.71-7.63 (dt, J = 14.0, 7.8 Hz, 2H), 4.36 (s, 2H), 3.16 (s, 2H), 1.76-1.45 (m, 9H), 1.28-1.25 (m, 1H). | Referring to Example 14 |
| 35 | 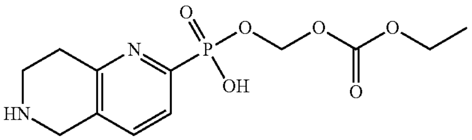 [SMILES: CCOC(=O)OCOP(=O)(O)c1ccc2c(n1)CCNC2] | MS (ESI) m/z $(M + H)^+$ = 317.0. $^1$H NMR (400 MHz, Deuterium Oxide) δ 7.68 (t, J = 5.6 Hz, 2H), 5.50 (d, J = 13.7 Hz, 2H), 4.42 (s, 2H), 4.02 (q, J = 7.1 Hz, 2H), 3.60 (t, J = 6.5 Hz, 2H), 3.20 (t, J = 6.5 Hz, 2H), 1.11 (t, J = 7.1 Hz, 3H). | Referring to Example 1 |

Biological Assay

Experimental Example 1: Plasma Clot Lysis Assay

1. Purpose

To determine the inhibitory effect of the compounds of the invention on the degradation of plasma clots.

2. Experimental Materials and Instruments

| Name(s) | Supplier | Lot number |
|---|---|---|
| Calcium chloride ($CaCl_2$•$2H_2O$) | Shanghai Aladdin Biochemical Technology Co., Ltd | C108383-500g |
| HEPES buffer solution (1M) | Thermo Fisher (Gibco) | 15630-106 |
| Tissue plasminogen activator (tPA) | Sigma-Aldrich | T0831-100UG |
| Human plasma | Provided by healthy volunteers | / |
| dd$H_2O$ | ULUPURE (Sichuan) | UPH-III-20T |
| UV-plate | Corning Inc. (America) | 3635 |
| Tranexamic acid (TXA) | Shanghai Haohong Biopharma Science and Technology Co., Ltd | Lc0701077 |
| Multimode microplate reader | BMG LABTECH | PHERAstar FSX |

3. Experimental Procedure 3.1 Collect fresh healthy human blood, mix I part of anticoagulant (0.109 M trisodium citrate) with 9 parts of blood, centrifuge at 2000×g for 20 min at room temperature, collect the supernatant (plasma), sub-package and store at −80° C. for later use.

3.2 On the day of experiment, the plasma was thawed in a water bath at 37° C., and all reagents except tPA were pre-warmed at 37° C.

3.3 Add 12.5 μL of 80 mM $CaCl_2$ (HEPES buffer, pH 7.4) to a 96-well plate, and then add 25 μL of different concentrations of test compound diluted with normal saline, add an equal volume of normal saline to the negative control well.

3.4 Mix 50 μL of pre-warmed plasma with 12.5 μL of 4 nM tPA (HEPES buffer, pH 7.4), immediately add to a 96-well plate, measure the absorbance at 405 nmevery 2 minutes, continuously for 15 hours 3.5 The absorption value changes with time, rising first and then decreasing. The time corresponding to the median of the absorption value in the descending section-the time corresponding to the median of the absorption value in the ascending section is the plasma clot degradation time (Clot lysis time). Taking the plasma clot lysis time of the negative control well as a reference, calculate the relative value of the plasma clot lysis time in the wells treated with different concentrations of the compound and the plasma clot lysis time of the negative control well to obtain the inhibition rate:

Inhibition rate %=(1−Clot lysis time of negative control well/Clot lysis time of compound treated well)×100%

3.6 Fitting the Dose-Response Curve

Taking the log value of the compound concentration as the X-axis, and the percentage inhibition rate as the Y-axis, and dose-response curves were fitted with the software GraphPad Prism 5 by using log (inhibitor) vs. Response-Variable slope to derive $IC_{50}$ values of compounds inhibiting the degradation of plasma clots.

$$Y=min+(max-min)/(1+10^{\wedge}((LogIC_{50}-X)\times Hillslope)).$$ Formula:

The inhibitory effect of the compounds of the present invention on plasma clot lysis is determined by the above tests, and the calculated $IC_{50}$ values of the compounds of the present invention are all lower than the $IC_{50}$ of tranexamic acid. For example, the compound of Example 1 of the present invention has an IC50 value of 0.9 μM for inhibition of plasma clot lysis, which is much lower than that of the current representative hemostatic drug tranexamic acid ($IC_{50}$ is 4.75 μM under the same test conditions). The relative coagulation activity of the present invention relative to tranexamic acid in vitro ($IC_{50}$ ratio=$IC_{50\ Examples}/IC_{50\ Tranexamic\ acid}$) is shown in the following table:

| Examples | $IC_{50}$ ratio |
|---|---|
| 1 | 0.19 |
| 2 | 0.11 |
| 3 | 0.86 |
| 4 | 0.36 |
| 5 | 1.3 |
| 6 | 0.09 |

-continued

| Examples | $IC_{50}$ ratio |
|---|---|
| 7 | 0.3 |
| 8 | 0.2 |
| 9 | 0.25 |
| 10 | 0.17 |
| 11 | 0.08 |
| 12 | 0.2 |
| 13 | 0.2 |
| 14 | 0.4 |
| 15 | 0.29 |
| 16 | 0.07 |
| 17 | 0.2 |
| 18 | 0.23 |
| 19 | 0.26 |
| 20 | 0.21 |
| 21 | 0.25 |
| 22 | 0.14 |
| 23 | 0.19 |
| 24 | 0.14 |
| 25 | 0.21 |
| 26 | 0.09 |
| 27 | 0.1 |
| 28 | 0.07 |
| 29 | 0.09 |
| 30 | 0.75 |
| 31 | 0.1 |
| 32 | 0.7 |
| 33 | 0.22 |
| 34 | 0.29 |
| 35 | 0.18 |

Experimental data shows that the compounds of the present invention can effectively inhibit the degradation of plasma clots, exhibit excellent coagulation and hemostaticactivity, and their effective dose is far lower than that of the most frequently used hemostatic drugs in clinical practice, and therefore can effectively avoid adverse reactions and complications caused by high-dose administration, and has an excellent clinical application prospect.

Experimental Example 2: Rat PK Assay

1. Purpose

The pharmacokinetic profile of the compounds of the invention in rats was studied by measuring the plasma drug concentration after intravenous administration.

2. Animals

Male Sprague-Dawley rats of SPF grade, 3 rats each group, were obtained from: Shanghai Sippe-Bk Lab Animal Co., Ltd.

3. Pharmaceutical Formulation and Administration

The compound was weighed and dissolved in normal saline to prepare a 0.2 mg/mL solution for intravenous administration.

The day before the experiment, the rats were fasted overnight and fed 4 hours after administration.

On the day of the experiment, the rats were administered according to the scheme in the table below. At each time point after administration, approximately 200 μL of blood was collected from the jugular vein and placed in heparin sodium anticoagulation tubes. Blood samples were placed on ice after collection, and the plasma was separated by centrifugation within 1 hour (centrifugation conditions: 6800 g, 6 minutes, 2-8° C.). The separated plasma was stored in a refrigerator at −80° C. for biological sample analysis.

| Dosage (mg · $kg^{-1}$) | Volume · (mL · $kg^{-1}$) | Route of administration | Dosing scheme | Fasting or not | Sample collection time point |
|---|---|---|---|---|---|
| 1 | 5 | Intravenous injection | Single dose | Yes | Before administration, 5, 15, 30 min, 1, 2, 4, 8, 24 h after administration |

4. Biological Analysis

The compound concentration in rat plasma was determined by the following method:

Instruments and equipment: LC-MS/MS-19 (TQ5500, AB SCIEX, USA).

Internal standard: warfarin.

Chromatographic column: ACQUITY UPLC BEH C18, model 1.7 um 2.1*50 mm, purchased from Shenzhen Novah Chemical Technology Co., Ltd.;

Flow rate: 0.60 ml/min.

Column temperature: 40° C.

Mobile phase A: 0.1% formic acid in water.

Mobile phase B: 0.1% formic acid in acetonitrile.

The elution gradient is shown in Table 3.

TABLE 3

Elution gradient

| Time (min) | Mobile phase A (%) | Mobile phase B (%) |
|---|---|---|
| 0 | 98 | 2 |
| 0.60 | 12 | 88 |
| 1.10 | 12 | 88 |
| 1.11 | 98 | 2 |
| 1.40 | 98 | 2 |

MS detection conditions: electrospray ion source (ESI), positive ion mode, MRM scan.

Take 30 μL of the plasma sample prepared from item "3", add 300 μL MeOH containing 100 ng/ml of internal standard to precipitate protein. The mixture was vortexed for 1 minute and centrifuged at 18000 g for 7 minutes. The supernatant was transferred to a 96-well plate. Inject 4 μL of supernatant into LC-MS/MS for analysis.

The concentration of the compound in rat plasma was determined by the above-mentioned LC-MS/MS analysis method, and pharmacokinetic parameters were calculated by using Phoenix WinNonlin7.0 software according to blood concentration data of different time points.

Some compounds of the present invention were tested using the above experiments, and the measured pharmacokinetic parameters in rats are shown in the table below.

TABLE
In vivo pharmacokinetic data of SD rats intravenously administered with test compounds
| Compound | Structure | $T_{1/2}$ (h) | Cmax (ng/mL) | AUC (h*ng/mL) | CL (mL/h/kg) |
|---|---|---|---|---|---|
| Tranexamic acid | 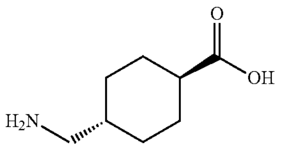 [SMILES: NC[C@H]1CC[C@H](C(=O)O)CC1] | 1.28 | 4408 | 2825 | 347 |
| Example 1 | 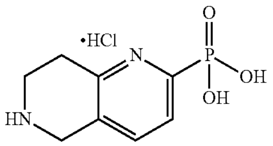 [SMILES: O=P(O)(O)c1ccc2c(n1)CCNC2 ; Cl] | 1.96 | 10150.56 | 13981.88 | 68.51 |
| Example 2 | 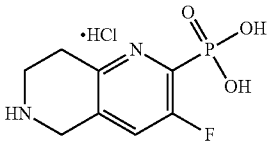 [SMILES: O=P(O)(O)c1nc2c(cc1F)CNCC2 ; Cl] | 4.15 | 10124.92 | 30085.93 | 33.29 |
| Example 8 | 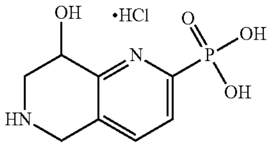 [SMILES: O=P(O)(O)c1ccc2c(n1)C(O)CNC2 ; Cl] | 1.74 | 5990.42 | 6663.83 | 146.41 |
| Example 15 | 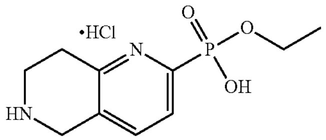 [SMILES: CCOP(=O)(O)c1ccc2c(n1)CCNC2 ; Cl] | 0.77 | 4891.57 | 2830.57 | 350.95 |
| Example 17 | 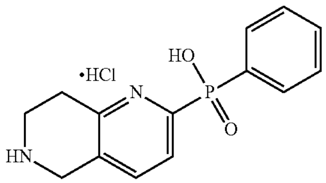 [SMILES: O=P(O)(c1ccccc1)c1ccc2c(n1)CCNC2 ; Cl] | 1.53 | 4094.64 | 2823.18 | 350.02 |
| Example 22 | 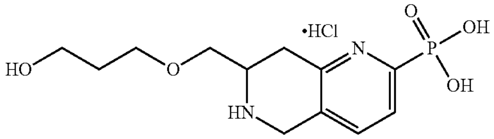 [SMILES: O=P(O)(O)c1ccc2c(n1)CC(COCCCO)NC2 ; Cl] | 3.58 | 6790.36 | 5530.11 | 178.97 |

Experimental Example 3: Human Whole Blood Thromboelastography Assay

1. Purpose

The antifibrinolytic effect of the compounds of the invention in the human whole blood under hyperfibrinolytic state induced by rtPA (recombinant tissue plasma activator) was determined using the Thromboelastogram (TEG).

2. Main Experimental Materials and Instruments

Experimental Materials

| Name of reagent | Supplier | Lot number |
|---|---|---|
| Alteplase for injection | Boehringer Ingelheim Pharma GmbH&Co.KG | 006099 |

Instrument

| Name of the instrument | Manufacturer | Type number |
|---|---|---|
| Thrombelastograghy | Shenzhen Medcaptain Medical Technology Co., Ltd. | PHA-TEG-01 |

Source of human blood: All human blood used in the experiments was provided by healthy volunteers.

3. Experimental Procedure (1) Preparation of test substance solution: Accurately weigh the test substance, and use normal saline to prepare the test substance to the following concentrations (100×test concentration):

Tranexamic acid (μM): 3000, 1000, 300, 100, 30, 10, 0;

Example 6 (μM): 1000, 300, 100, 30, 10, 3, 0.

(2) Preparation of rt-PA (alteplase for injection): the active dry powder of rtPA was formulated to 25 μg/mL using water for injection in the rtPA package.

(3) Reaction system:

Mix 392 μL of sodium citrate anticoagulated whole blood with 4 μL rtPA and 4 μL test substance, reacted at room temperature, and TEG curve was detected for 2 hours to obtain the time parameter of CLT (clot lysis time).

(4) Result calculations

Taking the log value of the compound concentration as the X-axis and the CLT value as the Y-axis, and dose-response curves were fitted using log (inhibitor) vs. Response-Variable slope (GraphPad Prism 8 software).

$$Y = \min + (\max - \min)/(1 + 10\hat{}((\mathrm{Log}IC_{50} - X)\times\mathrm{Hillslope})).$$ Formula The concentration of compound corresponding to doubling the CLT time was calculated.

4. Results of the Experiment

The inhibitory effect of the compounds of the present invention on fibrinolysis of human whole blood was determined by the above test, and the results are as follows:

Compound Concentration for Doubling CLT

| | Human blood | |
|---|---|---|
| Compound | concentration (μM) | CLT doubling (min) |
| Tranexamic acid | 1.78 | 34.66 |
| Example 6 | 0.12 | 37.06 |

Experiments have shown that compared with tranexamic acid, the most active and widely used drug in clinical practice, the compounds of the present invention have significantly higher exposure in animals, lower clearance rate, and longer half-life in animals; in plasma clot lysis assay and thromboelastography (TEG) assay, the compounds of the present invention can effectively inhibit the process of fibrinolysis, prolong the plasma clot lysis time (CLT), exhibit coagulation and hemostatic effect, and the effects are obviously better than that of the positive control. These experiments show that the compounds of the present invention have the advantages of better hemostatic activity, lower effective dose, and longer duration of drug effect, which can avoid various adverse reactions that may occur in clinical high-dose administration, and therefore improve the safety and efficacy of medication for patients. Moreover, the compounds of the present invention are convenient for preparation and large-scale industrial production, and can effectively reduce the cost of medication. The compounds of the present invention have good distribution, metabolism and excretion properties, the possibility of interaction between drugs is low, and can meet the requirements of pharmacokinetic parameters required for therapeutic effect in human body. In addition, the compounds of the present invention have low toxicity, have no effect on the respiratory system, central nervous system and cardiovascular system, and are well tolerated in single and repeated dose toxicity tests, have a sufficient safety window, and have no genotoxicity. The compounds of the present invention have broad clinical application prospects.

The invention claimed is:

1. A compound of formula I or a pharmaceutically acceptable salt, hydrate, stereoisomer, prodrug or a mixture thereof, (I)

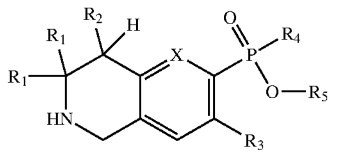

wherein X is N;

each $R_1$ is independently selected from the group consisting of hydrogen, substituted or unsubstituted amino, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, and substituted or unsubstituted aromatic heterocyclic group, or two $R_1$ together with the carbon atom to which they are attached form a carbocyclic ring comprising 3 to 8 carbon atoms;

$R_2$ is selected from the group consisting of hydrogen, hydroxyl, halogen, substituted or unsubstituted amino, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, and substituted or unsubstituted aromatic heterocyclic group;

$R_3$ is selected from the group consisting of hydrogen, halogen, and substituted or unsubstituted alkyl;

$R_4$ is selected from the group consisting of hydrogen, substituted or unsubstituted amino, hydroxyl, substituted or unsubstituted aryl, substituted or unsubstituted alkyl, and substituted or unsubstituted aromatic heterocyclic group; and $R_5$ is selected from the group consisting of hydrogen, substituted or unsubstituted alkyl, haloalkyl, substituted or unsubstituted cycloalkyl, substituted or unsubstituted aliphatic heterocyclic group, substituted or unsubstituted aryl, substituted or unsubstituted aromatic heterocyclic group, alkyl-carbonyl-oxy-alkyl, and alkoxy-carbonyl-oxy-alkyl.

2. The compound according to claim 1 or a pharmaceutically acceptable salt, hydrate, stereoisomer, prodrug or a mixture thereof, having the structure of formula I', Formula I'

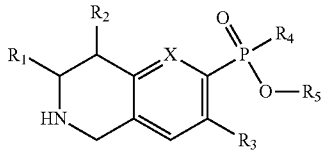

wherein X is N;

$R_1$ is selected from the group consisting of hydrogen, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, and substituted or unsubstituted aromatic heterocyclic group;

$R_2$ is selected from the group consisting of hydrogen, hydroxyl, substituted or unsubstituted amino, substituted or unsubstituted alkyl, substituted or unsubstituted alkoxy, haloalkyl, substituted or unsubstituted cycloalkyl, substituted or unsubstituted aliphatic heterocyclic group, substituted or unsubstituted aryl, and substituted or unsubstituted aromatic heterocyclic group;

$R_3$ is selected from the group consisting of hydrogen, halogen, and substituted or unsubstituted alkyl;

$R_4$ is selected from the group consisting of hydrogen, substituted or unsubstituted amino, hydroxyl, substituted or unsubstituted aryl, substituted or unsubstituted alkyl, and substituted or unsubstituted aromatic heterocyclic group; and $R_5$ is selected from the group consisting of hydrogen, substituted or unsubstituted alkyl, haloalkyl, substituted or unsubstituted cycloalkyl, substituted or unsubstituted aliphatic heterocyclic group, substituted or unsubstituted aryl, and substituted or unsubstituted aromatic heterocyclic group.

3. The compound according to claim 2 or a pharmaceutically acceptable salt, hydrate, stereoisomer, prodrug or a mixture thereof, wherein:

$R_1$ is selected from the group consisting of hydrogen, substituted or unsubstituted $C_1$-$C_6$ alkyl, substituted or unsubstituted $C_1$-$C_6$ alkoxy, $C_1$-$C_4$ haloalkyl, substituted or unsubstituted $C_3$-$C_6$ cycloalkyl, substituted or unsubstituted 4-8 membered aliphatic heterocyclic group, substituted or unsubstituted 6-10 membered aryl, and substituted or unsubstituted 6-10 membered aromatic heterocyclic group;

$R_2$ is selected from the group consisting of hydrogen, hydroxyl, substituted or unsubstituted amino, substituted or unsubstituted $C_1$-$C_6$ alkyl, substituted or unsubstituted $C_1$-$C_6$ alkoxy, $C_1$-$C_4$ haloalkyl, substituted or unsubstituted $C_3$-$C_6$ cycloalkyl, substituted or unsubstituted 4-8 membered aliphatic heterocyclic group, substituted or unsubstituted 6-10 membered aryl, and substituted or unsubstituted 6-10 membered aromatic heterocyclic group;

$R_3$ is selected from the group consisting of hydrogen, fluorine, chlorine, bromine, and substituted or unsubstituted $C_1$-$C_4$ alkyl;

$R_4$ is selected from the group consisting of hydrogen, substituted or unsubstituted amino, hydroxyl, substituted or unsubstituted 6-10 membered aryl, substituted or unsubstituted $C_1$-$C_4$ alkyl, and substituted or unsubstituted 6-10 membered aromatic heterocyclic group; and $R_5$ is selected from the group consisting of hydrogen, substituted or unsubstituted $C_1$-$C_4$ alkyl, substituted or unsubstituted $C_1$-$C_4$ haloalkyl, substituted or unsubstituted $C_3$-$C_6$ cycloalkyl, substituted or unsubstituted 4-8 membered aliphatic heterocyclic group, substituted or unsubstituted 6-10 membered aryl, and substituted or unsubstituted 6-10 membered aromatic heterocyclic.

4. The compound according to claim 1 or a pharmaceutically acceptable salt, hydrate, stereoisomer, prodrug or a mixture thereof, wherein:

said alkyl is selected from methyl, ethyl, propyl, isopropyl, n-butyl and tert-butyl;

said alkoxy is selected from methoxy, ethoxy, n-propoxy and isopropoxy;

said cycloalkyl is selected from cyclopropyl, cyclobutyl, cyclopentyl, cyclopentenyl, cyclohexyl and cyclohexenyl;

said aliphatic heterocyclic group is selected from oxetanyl, pyrrolidinyl, tetrahydrofuranyl and morpholinyl;

said aryl is selected from phenyl and naphthyl; and said aromatic heterocyclic group is selected from pyridyl, pyrimidyl, imidazolyl, pyrazolyl, thiazolyl, oxazolyl, isoxazolyl and 1,2,4-oxadiazolyl.

5. The compound of claim 1 or a pharmaceutically acceptable salt, hydrate, stereoisomer, prodrug or a mixture thereof, wherein each $R_1$ is independently selected from the group consisting of hydrogen, substituted or unsubstituted $C_1$-$C_6$ alkyl, and substituted or unsubstituted $C_1$-$C_6$ alkoxy; wherein the substituted $C_1$-$C_6$ alkyl or substituted $C_1$-$C_6$ alkoxy is substituted with one or more groups selected from hydroxyl, phenyl, $C_1$-$C_4$ alkoxy, phenyl substituted with $C_1$-$C_4$ alkoxy, and cyclohexyl; or two $R_1$ together with the carbon atom to which they are attached form a cyclobutyl, cyclopentyl, or cyclohexyl ring.

6. The compound according to claim 2 or a pharmaceutically acceptable salt, hydrate, stereoisomer, prodrug or a mixture thereof, wherein each $R_1$ is independently selected from the group consisting of hydrogen, $—CH_2OH$, isobutyl, tert-butyl, $—O(CH_2)_2OH$, $—O(CH_2)_3OH$, $—(CH_2)_4OH$, $—CH_2$-$O(CH_2)_3OH$, phenylethyl, propyl, isopentyl, 3,3- dimethylbutyl, cyclohexylmethyl, cyclohexylethyl, phenylpropyl, and 4-methoxyphenylethyl.

7. The compound according to claim 1 or a pharmaceutically acceptable salt, hydrate, stereoisomer, prodrug or a mixture thereof, wherein $R_2$ is selected from the group consisting of hydrogen, halogen, hydroxyl, hydroxy-substituted $C_1$-$C_6$ alkoxy, and 6-membered aliphatic heterocyclic group containing 1 to 3 heteroatoms selected from N, O and S, wherein the S heteroatom is optionally oxidized.

8. The compound according to claim 7 or a pharmaceutically acceptable salt, hydrate, stereoisomer, prodrug or a mixture thereof, wherein $R_2$ is selected from the group consisting of hydrogen, hydroxyl, $—OCH_2CH_2OH$

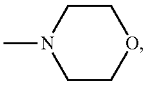 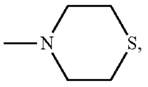 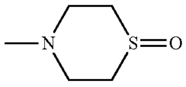 and

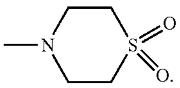

9. The compound according to claim 1 or a pharmaceutically acceptable salt, hydrate, stereoisomer, prodrug or a mixture thereof, wherein $R_3$ is selected from hydrogen of and fluorine.

10. The compound according to claim 1 or a pharmaceutically acceptable salt, hydrate, stereoisomer, prodrug or a mixture thereof, wherein $R_4$ is selected from the group consisting of hydroxyl, phenyl, $C_1$-$C_6$ alkyl and phenyl substituted $C_1$-$C_6$ alkyl.

11. The compound according to claim 1 or a pharmaceutically acceptable salt, hydrate, stereoisomer, prodrug or a mixture thereof, wherein $R_5$ is selected from the group consisting of hydrogen, substituted or unsubstituted $C_1$-$C_4$ alkyl, $C_1$-$C_4$ alkylcarbonyloxy-$C_1$-$C_4$ alkyl and $C_1$-$C_4$ alkoxycarbonyloxy $C_1$-$C_4$ alkyl.

12. The compound of formula I according to claim 1, selected from the group consisting of:

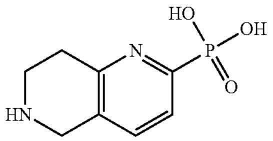

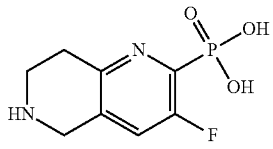

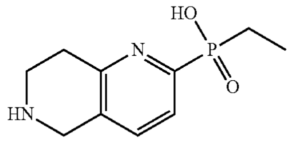

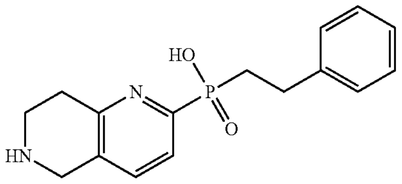

-continued

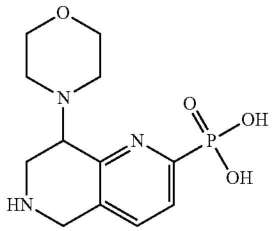

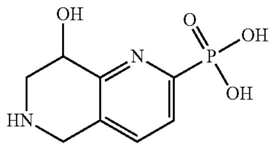

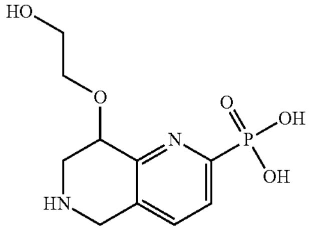

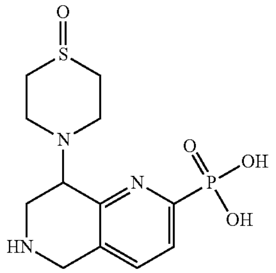

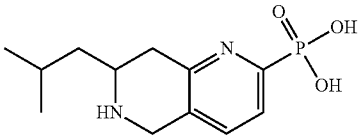

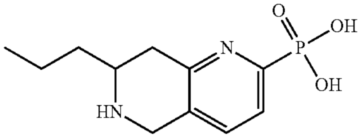

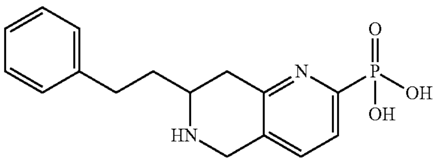

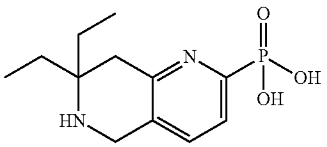

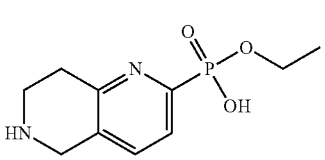

-continued

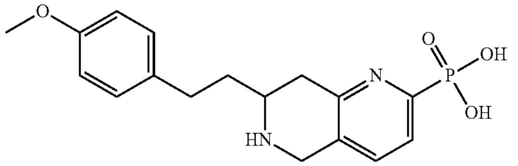

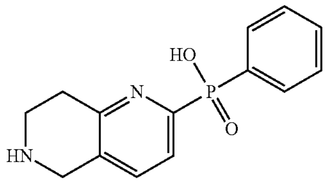

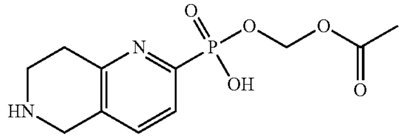

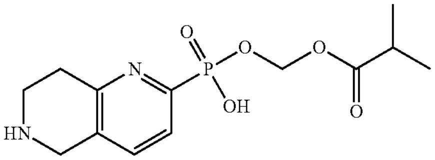

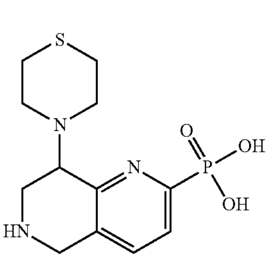

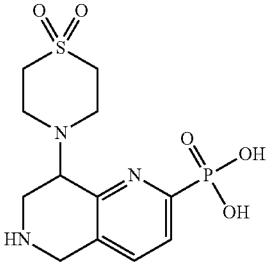

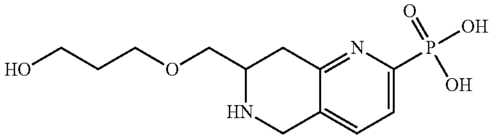

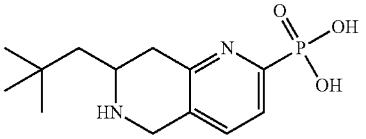

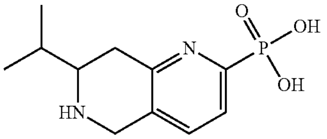

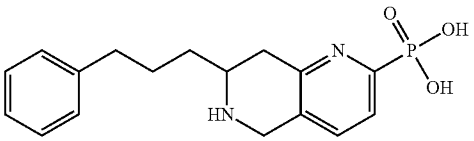

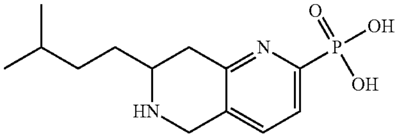

-continued

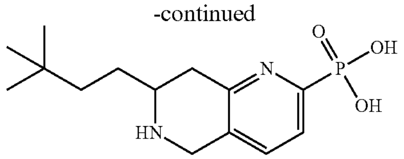

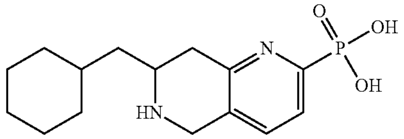

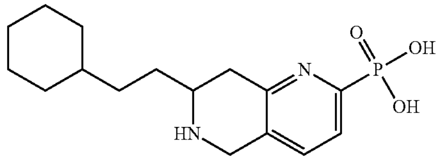

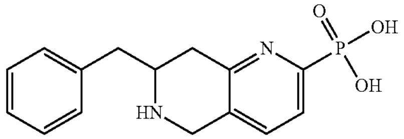

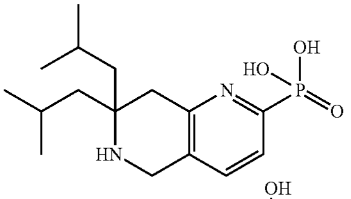

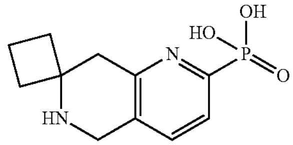

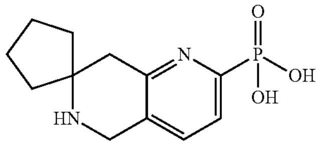

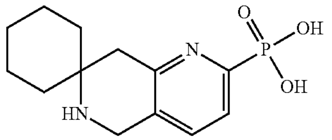

and

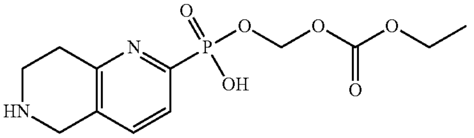

.

13. A pharmaceutical composition comprising at least one compound of claim 1 or a pharmaceutically acceptable salt, hydrate, stereoisomer, prodrug or a mixture thereof, and at least one pharmaceutically acceptable excipient.

14. A method of treating or alleviating bleeding diseases or conditions, comprising administering the compound of claim 1 or a pharmaceutically acceptable salt, hydrate, stereoisomer, prodrug or a mixture thereof to a subject in need thereof.

15. The method of claim 14, wherein the administration of the compound or a pharmaceutically acceptable salt, hydrate, stereoisomer, prodrug or a mixture thereof to the subject exhibits coagulation and hemostatic effect.

16. The method of claim 14, wherein the bleeding disease or condition is caused by hyperfibrinolysis, surgical and post-operative bleeding.

17. The compound of claim 2 or a pharmaceutically acceptable salt, hydrate, stereoisomer, prodrug or a mixture thereof, wherein $R_1$ is selected from the group consisting of hydrogen, substituted or unsubstituted $C_1$-$C_6$ alkyl, and substituted or unsubstituted $C_1$-$C_6$ alkoxy; wherein the substituted $C_1$-$C_6$ alkyl or substituted $C_1$-$C_6$ alkoxy is substituted with one or more groups selected from hydroxyl, phenyl, $C_1$-$C_4$ alkoxy, phenyl substituted with $C_1$-$C_4$ alkoxy, and cyclohexyl.

18. The compound according to claim 7 or a pharmaceutically acceptable salt, hydrate, stereoisomer, prodrug or a mixture thereof, wherein $R_2$ is hydrogen.

19. The compound according to claim 10 or a pharmaceutically acceptable salt, hydrate, stereoisomer, prodrug or a mixture thereof, wherein $R_4$ is selected from the group consisting of hydroxyl, phenyl, ethyl and phenylethyl.

20. The compound according to claim 2 or a pharmaceutically acceptable salt, hydrate, stereoisomer, prodrug or a mixture thereof, wherein $R_2$ is selected from the group consisting of hydrogen, hydroxyl, hydroxy-substituted $C_1$-$C_6$ alkoxy, and 6-membered aliphatic heterocyclic group containing 1 to 3 heteroatoms selected from N, O and S, wherein the S heteroatom is optionally oxidized.

21. The compound according to claim 20 or a pharmaceutically acceptable salt, hydrate, stereoisomer, prodrug or a mixture thereof, wherein $R_2$ is selected from the group consisting of hydrogen, hydroxyl, $—OCH_2CH_2OH$,

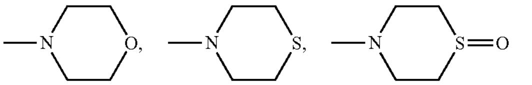

and

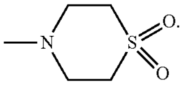

22. The compound according to claim 20 or a pharmaceutically acceptable salt, hydrate, stereoisomer, prodrug or a mixture thereof, wherein $R_2$ is hydrogen.

23. The compound according to claim 2 or a pharmaceutically acceptable salt, hydrate, stereoisomer, prodrug or a mixture thereof, wherein $R_4$ is selected from the group consisting of hydroxyl, phenyl, $C_1$-$C_6$ alkyl and phenyl substituted $C_1$-$C_6$ alkyl.

24. The compound according to claim 23 or a pharmaceutically acceptable salt, hydrate, stereoisomer, prodrug or a mixture thereof, wherein $R_4$ is selected from the group consisting of hydroxyl, phenyl, ethyl and phenylethyl.

25. The compound according to claim 2 or a pharmaceutically acceptable salt, hydrate, stereoisomer, prodrug or a mixture thereof, wherein $R_5$ is selected from the group consisting of hydrogen, and substituted or unsubstituted $C_1$-$C_4$ alkyl.

26. The compound according to claim 25 or a pharmaceutically acceptable salt, hydrate, stereoisomer, prodrug or a mixture thereof, wherein $R_5$ is selected from the group consisting of hydrogen, and ethyl.

27. The compound according to claim 11 or a pharmaceutically acceptable salt, hydrate, stereoisomer, prodrug or a mixture thereof, wherein $R_5$ is selected from the group consisting of hydrogen, ethyl, methylcarbonyloxymethyl, isopropylcarbonyloxymethyl and methoxycarbonyloxymethyl.

28. A pharmaceutical composition comprising at least one compound of claim 2 or a pharmaceutically acceptable salt, hydrate, stereoisomer, prodrug or a mixture thereof, and at least one pharmaceutically acceptable excipient.

* * * * *